(12) United States Patent
Barrall et al.

(10) Patent No.: US 10,906,945 B2
(45) Date of Patent: Feb. 2, 2021

(54) MODIFIED ALPHA HEMOLYSIN POLYPEPTIDES AND METHODS OF USE

(71) Applicant: ELECTRONIC BIOSCIENCES, INC., San Diego, CA (US)

(72) Inventors: Geoffrey A. Barrall, San Jose, CA (US); Eric N. Ervin, Holladay, UT (US); Prithwish Pal, San Diego, CA (US)

(73) Assignee: ELECTRONIC BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 16/034,115

(22) Filed: Jul. 12, 2018

(65) Prior Publication Data
US 2018/0312551 A1 Nov. 1, 2018

Related U.S. Application Data

(62) Division of application No. 14/653,246, filed as application No. PCT/US2013/076698 on Dec. 19, 2013, now Pat. No. 10,047,129.

(60) Provisional application No. 61/740,322, filed on Dec. 20, 2012.

(51) Int. Cl.
*C07K 14/31* (2006.01)
*C12Q 1/6869* (2018.01)

(52) U.S. Cl.
CPC ............ *C07K 14/31* (2013.01); *C12Q 1/6869* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 6,916,665 B2 * | 7/2005 | Bayley | C07K 14/31 435/5 |
| 6,936,433 B2 | 8/2005 | Akeson et al. | |
| 7,608,276 B2 | 10/2009 | Masignani et al. | |
| 7,731,826 B2 | 6/2010 | Hibbs et al. | |
| 7,777,505 B2 | 8/2010 | White et al. | |
| 8,124,191 B2 | 2/2012 | Ervin et al. | |
| 8,324,914 B2 | 12/2012 | Chen | |
| 8,962,242 B2 | 2/2015 | Chen | |
| 2004/0191845 A1 | 9/2004 | Bayley | |
| 2007/0281329 A1 | 12/2007 | Akeson et al. | |
| 2009/0136958 A1 | 5/2009 | Gershow | |
| 2009/0167288 A1 | 7/2009 | Reid et al. | |
| 2009/0222216 A1 | 9/2009 | Hibbs et al. | |
| 2010/0035260 A1 | 2/2010 | Olasagasti | |
| 2010/0203024 A1 | 8/2010 | Terman et al. | |
| 2012/0255862 A1 | 10/2012 | Dunnam et al. | |
| 2014/0216933 A1 | 8/2014 | Barrall et al. | |
| 2014/0248608 A1 | 9/2014 | Barrall et al. | |
| 2015/0329600 A1 | 11/2015 | Barral et al. | |
| 2018/0312551 A1 | 11/2018 | Barrall et al. | |
| 2019/0178838 A1 | 6/2019 | Barrall et al. | |

FOREIGN PATENT DOCUMENTS

| | | | |
|---|---|---|---|
| WO | WO 08/102120 | 8/2008 | |
| WO | WO-2008102120 A1 * | 8/2008 | ....... G01N 33/48728 |
| WO | WO 09/077734 | 6/2009 | |
| WO | WO 10/034018 | 3/2010 | |
| WO | WO 10/055307 | 5/2010 | |
| WO | WO 10/081875 | 7/2010 | |
| WO | WO 12/178093 | 12/2012 | |
| WO | WO 12/178097 | 12/2012 | |
| WO | WO 14/100481 | 6/2014 | |

OTHER PUBLICATIONS

Mohammad 2008 (Controlling a single protein in a nanopore through electrostatic traps; J. Am. Chem. Soc. 130: 4081-4088) (Year: 2008).*
Mulero et al. 2010 (Nanopore-based devices for Bioanalytical Applications; JALA Technology Review; 243-252) (Year: 2010).*
Ayub and Bayley, "Individual RNA base recognition in immobilized oligonucleotides using a protein nanopore" Nano Lett (2012) 12(11):5637-5643.
Barrall et al., "Quartz Nanopore Membranes for Low Noise Measurements of Ion Channel Conductance" Biophysical Journal (2010) 98(3) supp. 1:598a.
Chu et al., "Real-Time Monitoring of DNA Polymerase Function and Stepwise Single-Nucleotide DNA Strand Translocation through a Protein Nanopore" Angewandte Chemie (Int. Ed. In English) (2010) 122(52):10304-10307.
Clarke et al., "Continuous base identification for single-molecule nanopore DNA sequencing" Nature Nanotechnology (2009) 4:265-270.
Ervin et al., "Mapping the Sensing Zone of Alpha-Hemolysin Using Immobilized DNA Containing a Single Abasic Residue" Biophysical Journal (2011) 100(3):167a.
GenBank Accession No. M90536.1, *Staphylococcus aureus* alpha-hemolysin gene, 3' end, Apr. 26, 1993.
Kasianowicz et al., "Genetically Engineered Metal Ion Binding Sites on the Outside of a Channel's Transmembrane β-Barral" Biophysical Journal (1999) 76:837-845.
Lathrop et al., "Monitoring the Escape of DNA from a Nanopore Using an Alternating Current Signal" Journal of the American Chemical Society (2010) 132(6):1878-1885.
Li-Qun et al., "Reversal of charge selectivity in transmembrane protein pores by using noncovalent molecular adapters" PNAS USA (2000) 97(8):3959-3964.
Lubensky et al., "Driven Polymer Translocation Through a Narrow Pore" Biophys. J. (1999) 77(4):1824-1838.

(Continued)

*Primary Examiner* — Mary Maille Lyons
(74) *Attorney, Agent, or Firm* — Grant IP, Inc.

(57) ABSTRACT

Provided herein are alpha hemolysin polypeptides comprising modified amino acid sequences that can reduce the rate of translocation of a polymer. Also provided herein are apparatuses and devices comprising modified hemolysin polypeptides. Also provided herein are methods of using modified alpha hemolysin proteins for use in characterizing and/or sequencing a polymer or for use as molecular sensors.

18 Claims, 13 Drawing Sheets
Specification includes a Sequence Listing.

(56) References Cited

OTHER PUBLICATIONS

Maglia et al., "Enhanced translocation of single DNA molecules through alpha-hemolysin nanopores by manipulation of internal charge" PNAS USA (2008) 105(50):19720-19725.
Purnell et al., "Nucleotide Identification and Orientation Discrimination of DNA Homopolymers Immobilized in a Protein Nanopore" Nano Letters (2008) 8(9):3029-34.
Sigworth, "Design of the Patch Clamp" Single-channel recording, Sakmann and Neher, eds., pp. 3-35, New York: Plenum Press (1995).
Smeets et al., "Noise in solid-state nanopores" PNAS USA (2008) 105(2):417-421.
Stoddart et al., "Single-nucleotide discrimination in immobilized DNA oligonucleotides with a biological nanopore" PNAS USA (2009) 106:7702-7707.
Stoddart et al., "Nucleobase recognition in ssDNA at the central constriction of the alpha-hemolysin pore" Nano Lett. (2010) 10(9):3633-3637.
Timp et al., "Nanopore Sequencing: Electrical Measurements of the Code of Life" IEEE Transactions on Nanotechnology (2010) 9(3):281-294.
Walker and Bayley, "Key residues for membrane binding, oligomerization, and pore forming activity of staphylococcal alpha-hemolysin identified by cysteine scanning mutagenesis and targeted chemical modification" Journal of Biological Chemistry (1995) 270(39):23065-23071.
Zhang et al., "Bench-Top Method for Fabricating Glass-Sealed Nanodisk Electrodes, Glass Nanopore Electrodes, and Glass Nanopore Membranes of Controlled Size" Anal. Chem. (2007) 79(13):4778-4787.
International Search Report and Written Opinion dated Nov. 2, 2012 in International Application No. PCT/US2012/043864, filed on Jun. 22, 2012 and published as WO 2012/178097 on Dec. 27, 2012.
International Preliminary Report on Patentability dated Jan. 9, 2014 in International Application No. PCT/US2012/043864, filed on Jun. 22, 2012 and published as WO 2012/178097 on Dec. 27, 2012.
International Search Report and Written Opinion dated Sep. 21, 2012 in International Application No. PCT/US2012/043859, filed on Jun. 22, 2012 and published as WO 2012/178093 on Dec. 27, 2012.
International Preliminary Report on Patentability dated Jan. 9, 2014 in International Application No. PCT/US2012/043859, filed on Jun. 22, 2012 and published as WO 2012/178093 on Dec. 27, 2012.
International Search Report and Written Opinion dated May 21, 2014 in International Application No. PCT/US2013/076698, filed on Dec. 19, 2013 and published as WO 2014/100481 on Jun. 26, 2014.
Extended European Search Report dated Nov. 4, 2014 in EP Application No. 12802702.6, filed on Jun. 22, 2012 and published as EP 2 724 148 on Apr. 30, 2014.
Extended European Search Report dated Nov. 4, 2014 in EP Application No. 12802737.2, filed on Jun. 22, 2012 and published as EP 2 724 150 on Apr. 30, 2014.
International Preliminary Report on Patentability dated Jul. 5, 2015 in International Application No. PCT/US2013/076698, filed on Dec. 19, 2013 and published as WO 2014/100481 on Jun. 26, 2014.
Office Action dated Nov. 25, 2015 in U.S. Appl. No. 14/128,588, filed May 9, 2014 and published as U.S. 2014-0248608 on Sep. 4, 2014.
Office Action dated Dec. 16, 2016 in U.S. Appl. No. 14/128,587, filed Apr. 4, 2014 and published as U.S. 2014-0216933 on Aug. 7, 2014.
Office Action dated May 12, 2017 in U.S. Appl. No. 14/128,587, filed Apr. 4, 2014 and published as U.S. 2014-0216933 on Aug. 7, 2014.
Office Action dated Mar. 19, 2018 in U.S. Appl. No. 14/128,587, filed Apr. 4, 2014 and published as U.S. 2014-0216933 on Aug. 7, 2014.
Office Action dated Oct. 16, 2018 in U.S. Appl. No. 14/128,587, filed Apr. 4, 2014 and published as U.S. 2014-0216933 on Aug. 7, 2014.
Office Action dated May 11, 2017 in U.S. Appl. No. 14/653,246, filed Jun. 17, 2015 and published as U.S. 2015-0329600 on Nov. 19, 2015.
Office Action dated Sep. 27, 2017 in U.S. Appl. No. 14/653,246, filed Jun. 17, 2015 and published as U.S. 2015-0329600 on Nov. 19, 2015.
Office Action dated Apr. 6, 2018 in U.S. Appl. No. 14/653,246, filed Jun. 17, 2015 and published as U.S. 2015-0329600 on Nov. 19, 2015.
Ervin, et al., "Creating a Single Sensing Zone within an Alpha-Hemolysin Pore Via Site Directed Mutagenesis", Bionanoscience, Mar. 1, 2014. pp. 78-84.

\* cited by examiner

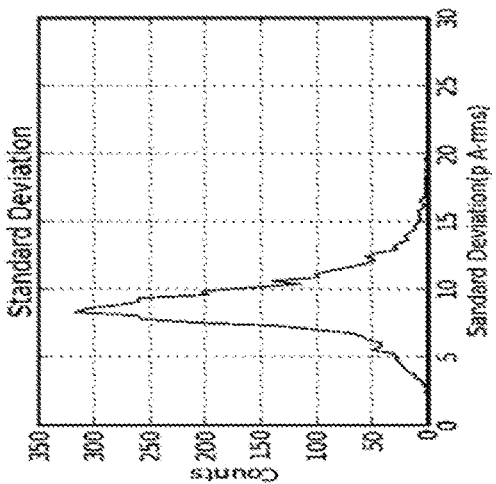
FIG. 1A
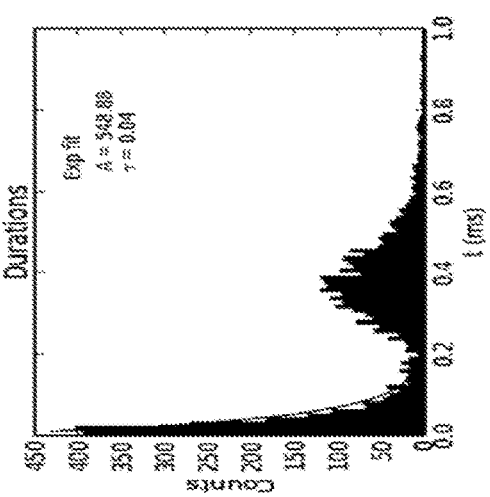
FIG. 1B
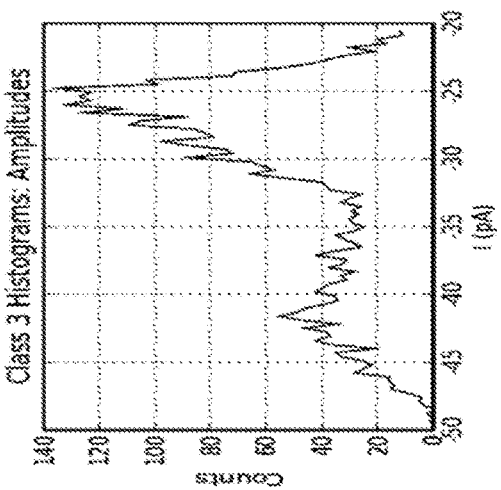
FIG. 1C
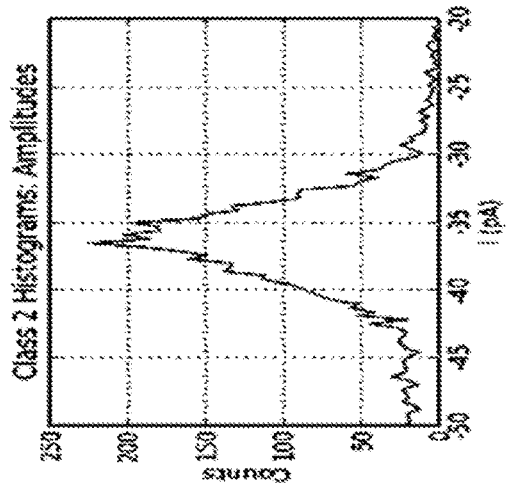
FIG. 1D
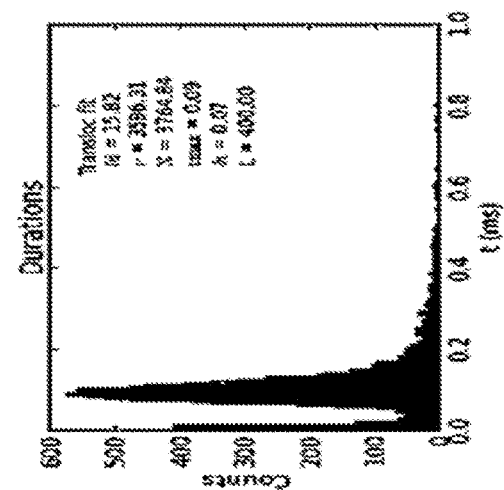
FIG. 1E
FIG. 1F

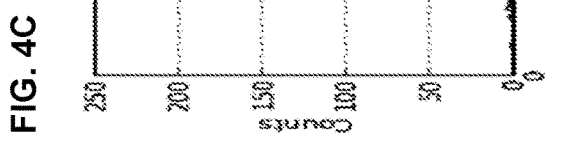
FIG. 4A
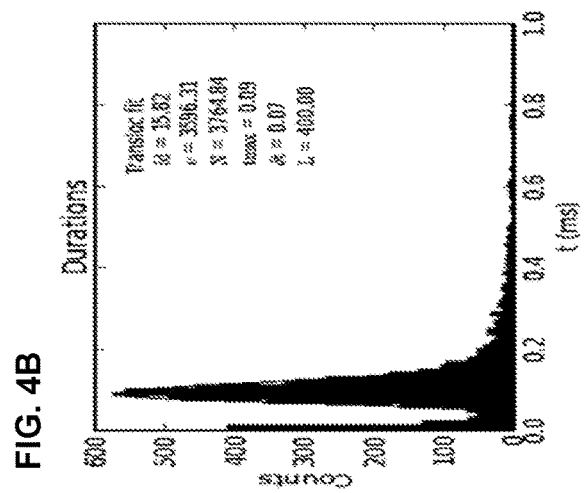
FIG. 4B
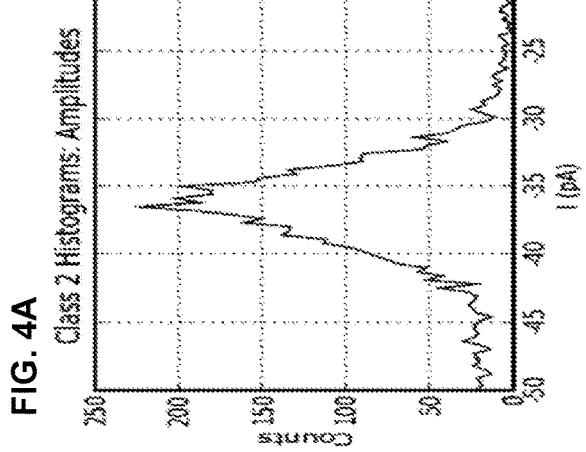
FIG. 4C
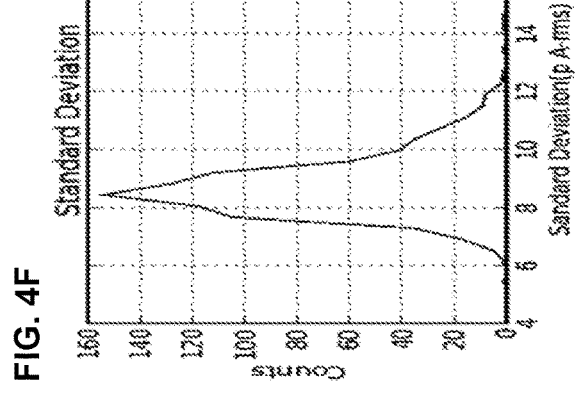
FIG. 4D
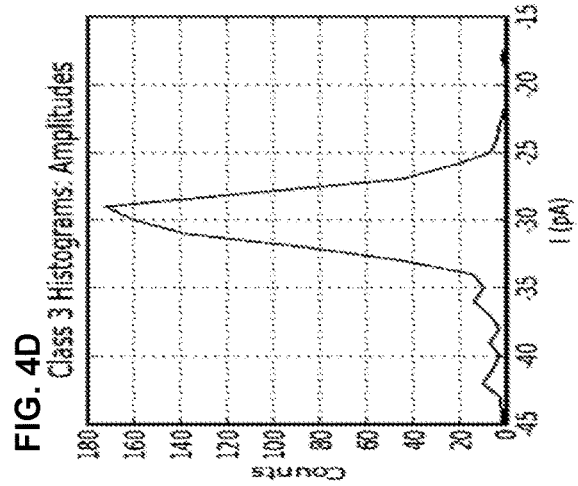
FIG. 4E
FIG. 4F

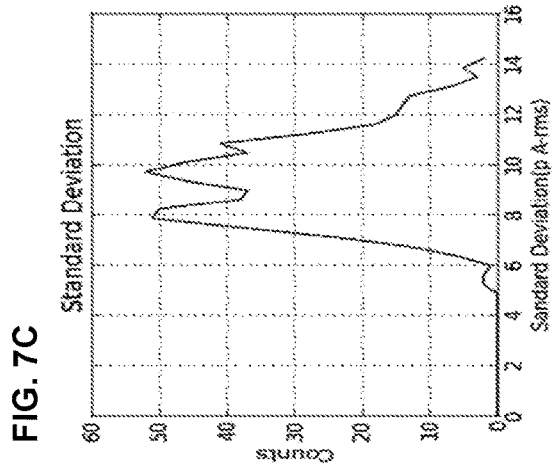
FIG. 7A
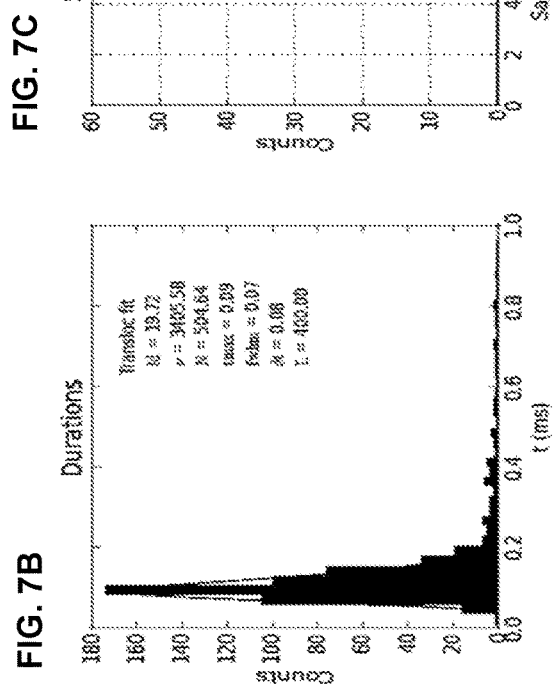
FIG. 7B
FIG. 7C
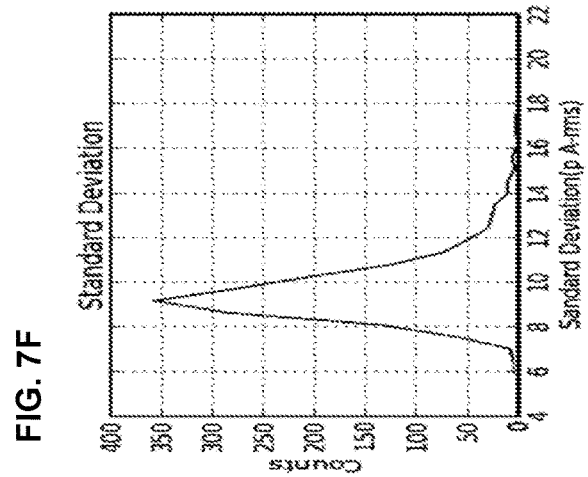
FIG. 7D
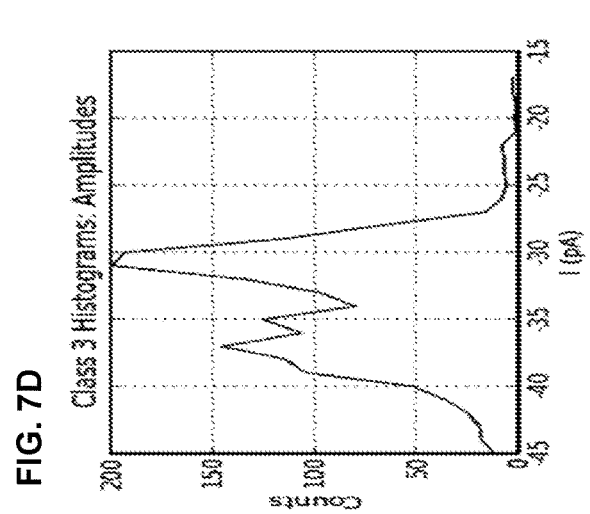
FIG. 7E
FIG. 7F

MODIFIED ALPHA HEMOLYSIN POLYPEPTIDES AND METHODS OF USE

RELATED PATENT APPLICATIONS

This patent application is a divisional of patent application Ser. No. 14/653,246, filed on Jun. 17, 2015, entitled MODIFIED ALPHA HEMOLYSIN POLYPEPTIDES AND METHODS OF USE, naming Geoffrey A. Barrall, Eric N. Ervin and Prithwish Pal as inventors, which is a 35 U.S.C. 371 U.S. national phase patent application of PCT/US2013/076698, filed on Dec. 19, 2013, entitled MODIFIED ALPHA HEMOLYSIN POLYPEPTIDES AND METHODS OF USE, naming Geoffrey A. Barrall, Eric N. Ervin and Prithwish Pal as inventors, which claims the benefit of U.S. provisional patent application No. 61/740,322 filed on Dec. 20, 2012, entitled MODIFIED ALPHA HEMOLYSIN PROTEIN PORES AND METHODS OF USE, naming Geoffrey A. Barrall, Eric N. Ervin and Prithwish Pal as inventors. The entire content of the foregoing applications are incorporated herein by reference, including all text, tables and drawings.

STATEMENT OF GOVERNMENT SUPPORT

This invention was made with government support under Grant Nos. 1R01HG005095 and 2R44HG004466 awarded by the National Institutes of Health, specifically the National Human Genome Research institute. The government has certain rights in the invention.

SEQUENCE LISTING

The instant application contains a Sequence Listing which has been submitted electronically in ASCII format and is hereby incorporated by reference in its entirety. Said ASCII copy, created on Jan. 29, 2014, is named EBS-1007-PC_SL.txt and is 9,124 bytes in size.

FIELD

The technology herein relates, in part, to modified alpha hemolysin polypeptides that transport polymers across a membrane.

BACKGROUND

Hemolysins are members of a family of protein toxins that are produced by a wide variety of organisms. Some hemolysins, for example alpha hemolysins, can disrupt the integrity of a cell membrane (e.g., a host cell membrane) by forming a pore or channel in the membrane. Pores or channels that are formed in a membrane by pore forming proteins can be used to transport certain polymers (e.g., polypeptides or polynucleotides) from one side of a membrane to the other.

SUMMARY

Provided herein, in certain aspects, is a polypeptide comprising a modified alpha hemolysin amino acid sequence comprising one or more amino acid substitutions at one or more positions corresponding to positions 1-109 and 149-293 of the amino acid sequence of SEQ ID NO: 1, where each of the one or more amino acid substitutions independently is to (i) a non-native hydrophobic amino acid, or (ii) a non-native aromatic amino acid, or (iii) a non-native aromatic and hydrophobic amino acid. A modified alpha hemolysin polypeptide, the latter of which is also referred to as a modified alpha hemolysin protein pore herein, generally comprises, consists essentially of or consists of a modified alpha hemolysin amino acid sequence. An amino acid sequence of a wild-type (i.e., native, unmodified) alpha hemolysin polypeptide from *Staphylococcus aureus* is provided herein as SEQ ID NO: 1. In certain aspects a modified alpha hemolysin amino acid sequence comprises an amino acid modification at one or more positions corresponding to positions 1, 2, 3, 4, 5, 6, 7, 8, 9, 10, 11, 12, 13, 14, 15, 16, 97, 99, 101, 103, 105, 107, 109, 149, 151, 153, 155, 157, 159, 161, 163, 165, 167, 169, 225, 227, 229, 231 or 233 of SEQ ID NO: 1. In certain aspects the one or more positions correspond to positions 105, 107, 109, 149, 151 or 153 of SEQ ID NO: 1. In certain aspects the one or more positions correspond to positions 107, 109, 149 or 151 of SEQ ID NO: 1. In certain aspects the one or more positions correspond to positions 109 or 149 of SEQ ID NO: 1.

In certain aspects the modified alpha hemolysin amino acid sequence also comprises one or more substitutions located within a beta barrel of the alpha hemolysin polypeptide, where the one or more positions for the one or more substitutions in the beta barrel sometimes are chosen from one or more positions corresponding to positions 111, 113, 115, 117, 119, 121, 123, 125, 127, 129, 131, 133, 135, 137, 139, 141, 143, 145 and 147 of SEQ ID NO: 1. In certain aspects the modified alpha hemolysin amino acid sequence comprises at least two, at least three, at least four or at least five amino acid substitutions located in the beta barrel.

In certain aspects, a modified alpha hemolysin polypeptide is configured to translocate a polymer at least 20% slower than a reference alpha hemolysin polypeptide or at least 20% slower than a reference alpha hemolysin protein comprising one or more amino acid substitutions located in a beta barrel.

Also provided herein is a method of sequencing a polymer with a modified alpha hemolysin polypeptide comprising (a) contacting a polymer with a modified alpha hemolysin polypeptide, wherein the modified alpha hemolysin polypeptide comprises an amino acid sequence of a reference alpha hemolysin polypeptide comprising one or more amino acid substitutions, and (b) determining the sequence of the polymer according to one or more electrical changes across or through the modified alpha hemolysin polypeptide. A modified alpha hemolysin polypeptide described herein can be utilized in this method.

Also provided herein is a method of increasing a translocation time of a polymer through an alpha hemolysin polypeptide, comprising (a) contacting a polymer with a modified alpha hemolysin polypeptide, wherein the modified alpha hemolysin polypeptide comprises an amino acid sequence of a reference alpha hemolysin polypeptide comprising one or more amino acid substitutions, and (b) determining a first translocation time of the polymer through the modified alpha hemolysin polypeptide, wherein the first translocation time of the polymer through the modified alpha hemolysin polypeptide is at least 20% longer than a second translocation time of the polymer through the reference alpha hemolysin polypeptide. A modified alpha hemolysin polypeptide described herein can be utilized in this method.

Also provided herein is a method of translocating a polymer through a modified alpha hemolysin polypeptide, comprising (a) substituting one or more amino acids of a reference alpha hemolysin polypeptide, where a modified alpha hemolysin polypeptide is generated, and (b) contacting the modified alpha hemolysin polypeptide with a polymer, wherein the polymer translocates through the modified alpha hemolysin polypeptide. A modified alpha hemolysin polypeptide described herein can be utilized in this method.

Also provided herein in certain aspects is a nanopore device comprising a modified alpha hemolysin polypeptide, such as a modified alpha hemolysin polypeptide described herein.

Certain embodiments are described further in the following description, examples, claims and drawings.

BRIEF DESCRIPTION OF THE DRAWINGS

The drawings illustrate certain aspects and embodiments of the technology and are not limiting. For clarity and ease of illustration, the drawings are not made to scale and, in some instances, various aspects may be shown exaggerated or enlarged to facilitate an understanding of particular embodiments and aspects.

FIGS. 1-13 below each show three histograms for the data taken with a modified alpha hemolysin polypeptide (i.e., modified alpha hemolysin protein pore (e.g., Figures D-F) and the corresponding unmodified alpha hemolysin polypeptide without the at least one native amino acid substituted with the non-native amino acid (e.g., Figures A-C).

FIGS. 1A-F show histograms of translocations statistics for polyC100 translocating through alpha hemolysin polypeptide 4S SDKMS (e.g., without the at least one native amino acid substituted with the non-native amino acid) (FIGS. 1A-1C; 2D density translocation statistics: Tmax=102 μsec and open channel=−238/+254 pA) and a modified alpha hemolysin polypeptide YY-4S SDKMS (FIGS. 1D-1F; 2D density translocation statistics: Tmax C100-3'=362 μsec and open channel=−232/+251 pA). FIGS. 1A and 1D show amplitude histograms, FIGS. 1B and 1E show duration histograms and FIGS. 1C and 1F show standard deviation histograms for the indicated alpha hemolysin proteins.

FIGS. 2A and 2D show amplitude histograms, FIGS. 2B and 2E show duration histograms and FIGS. 2C and 2F show standard deviation histograms for the indicated alpha hemolysin proteins.

FIGS. 3A and 3D show amplitude histograms, FIGS. 3B and 3E show duration histograms and FIGS. 3C and 3F show standard deviation histograms for the indicated alpha hemolysin proteins.

FIGS. 4A-F show histograms of translocations statistics for polyC100 translocating through alpha hemolysin polypeptide 4S SDKMS (e.g., without the at least one native amino acid substituted with the non-native amino acid) (FIGS. 4A-4C; 2D density translocation statistics: Tmax=102 μsec and open channel=−238/+254 pA) and a modified alpha hemolysin polypeptide YW-4S SDKMS (FIGS. 4D-4F; 2D density translocation statistics: Tmax=1135 μsec and open channel=−234/+250 pA). FIGS. 4A and 4D show amplitude histograms, FIGS. 4B and 4E show duration histograms and FIGS. 4C and 4F show standard deviation histograms for the indicated alpha hemolysin proteins.

FIGS. 5A and 5D show amplitude histograms, FIGS. 5B and 5E show duration histograms and FIGS. 5C and 5F show standard deviation histograms for the indicated alpha hemolysin proteins.

FIGS. 6A and 6D show amplitude histograms, FIGS. 6B and 6E show duration histograms and FIGS. 6C and 6F show standard deviation histograms for the indicated alpha hemolysin proteins.

FIGS. 7A-F show histograms of translocations statistics for polyC100 translocating through alpha hemolysin polypeptide 4S L1351 D127K (e.g., without the at least one native amino acid substituted with the non-native amino acid) (FIGS. 7A-7C; 2D density translocation statistics: Tmax C100=100 μsec and open channel=−232/+272 pA) and a modified alpha hemolysin polypeptide YY-4S L1351 D127K (FIGS. 7D-7F; 2D density translocation statistics: Tmax 0100-3'=420 μsec and open channel=−232/+272 pA). FIGS. 7A and 7D show amplitude histograms, FIGS. 7B and 7E show duration histograms and FIGS. 7C and 7F show standard deviation histograms for the indicated alpha hemolysin proteins.

FIGS. 8A and 8D show amplitude histograms, FIGS. 8B and 8E show duration histograms and FIGS. 8C and 8F show standard deviation histograms for the indicated alpha hemolysin proteins.

FIGS. 9A and 9D show amplitude histograms, FIGS. 9B and 9E show duration histograms and FIGS. 9C and 9F show standard deviation histograms for the indicated alpha hemolysin proteins.

FIGS. 10A and 10D show amplitude histograms, FIGS. 10B and 10E show duration histograms and FIGS. 10C and 10F show standard deviation histograms for the indicated alpha hemolysin proteins.

FIGS. 11A and 11D show amplitude histograms, FIGS. 11B and 11E show duration histograms and FIGS. 11C and 11F show standard deviation histograms for the indicated alpha hemolysin proteins.

FIGS. 12A and 12D show amplitude histograms, FIGS. 12B and 12E show duration histograms and FIGS. 12C and 12F show standard deviation histograms for the indicated alpha hemolysin proteins.

FIGS. 13A and 13D show amplitude histograms, FIGS. 13B and 13E show duration histograms and FIGS. 13C and 13F show standard deviation histograms for the indicated alpha hemolysin proteins.

DETAILED DESCRIPTION

Hemolysins and Alpha Hemolysin

Figure 2C:
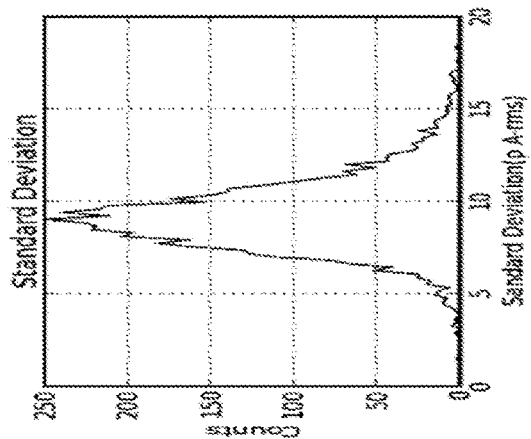
FIGS. 2A-F show histograms of translocations statistics for polyC100 translocating through alpha hemolysin polypeptide 4S SDKMS (e.g., without the at least one native amino acid substituted with the non-native amino acid) (FIGS. 2A-2C; 2D density translocation statistics: Tmax=102 μsec and open channel=−238/+254 pA) and a modified alpha hemolysin polypeptide 4Y-4S SDKMS (FIGS. 2D-2F; 2D density translocation statistics: Tmax=398 μsec and open channel=−231/+241 pA).
Figure 2B:
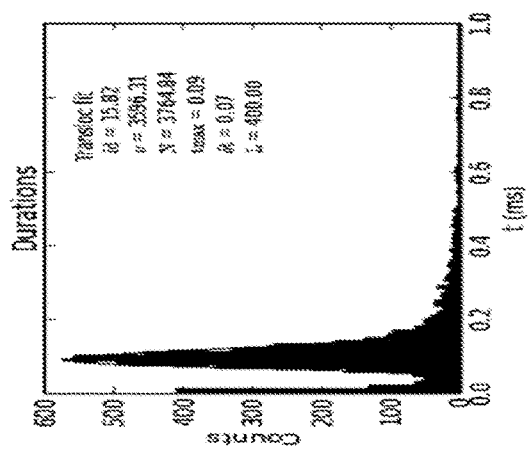
Figure 2A:
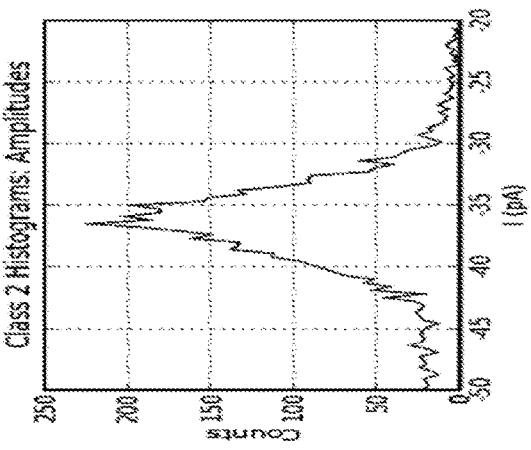
Figure 2F:
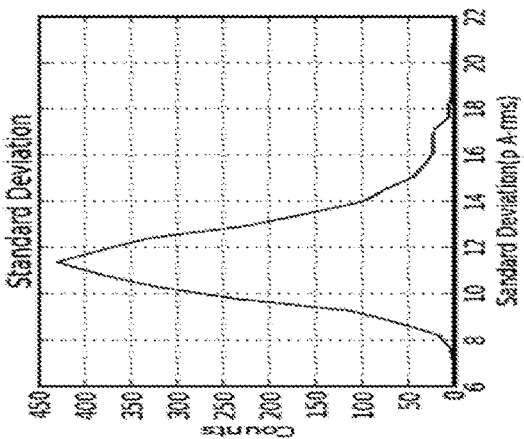
Figure 2E:
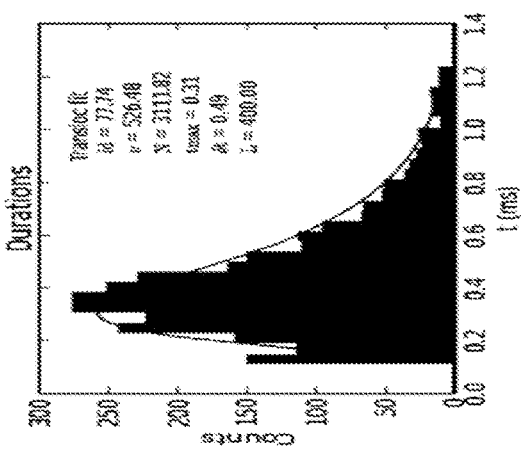
Figure 2D:
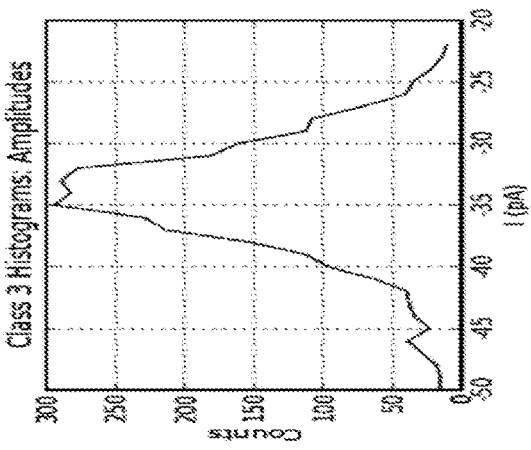
Figure 3A:
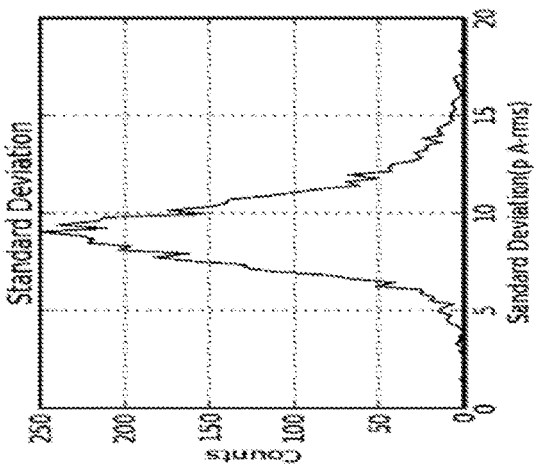
FIGS. 3A-F show histograms of translocations statistics for polyC100 translocating through alpha hemolysin polypeptide 4S+SDKMS (e.g., without the at least one native amino acid substituted with the non-native amino acid) (FIGS. 3A-3C; 2D density translocation statistics: Tmax=102 μsec and open channel=−238/+254 pA) and a modified alpha hemolysin polypeptide V149W-4S SDKMS (FIGS. 3D-3F; 2D density translocation statistics: Tmax=271 μsec and open channel=−231/+254 pA).
Figure 3B:
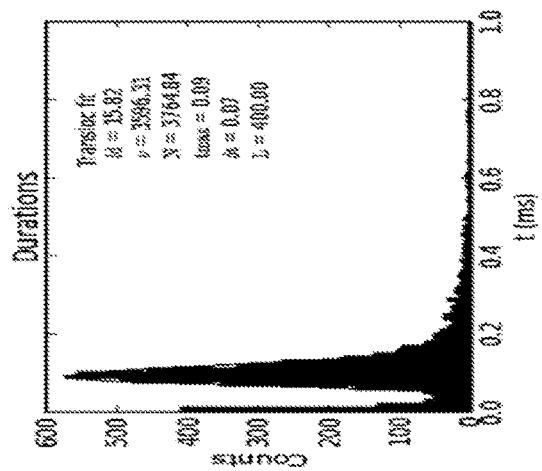
Figure 3C:
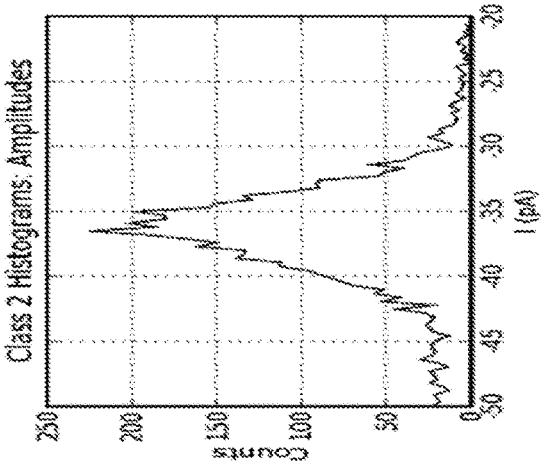
Figure 3D:
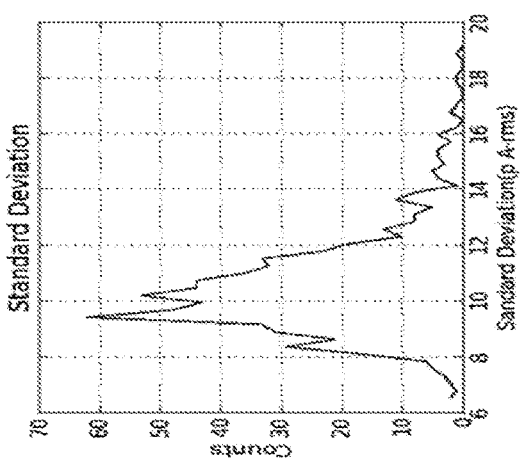
Figure 3E:
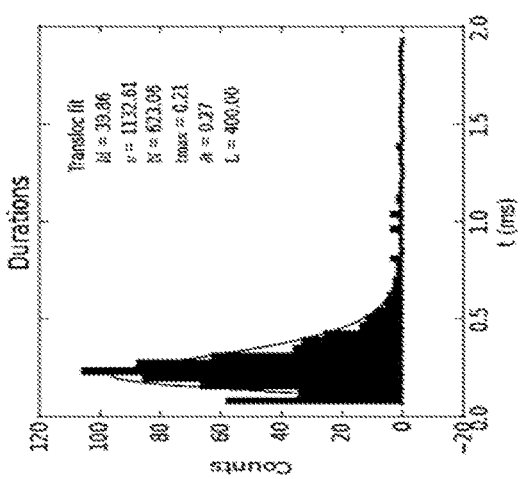
Figure 3F:
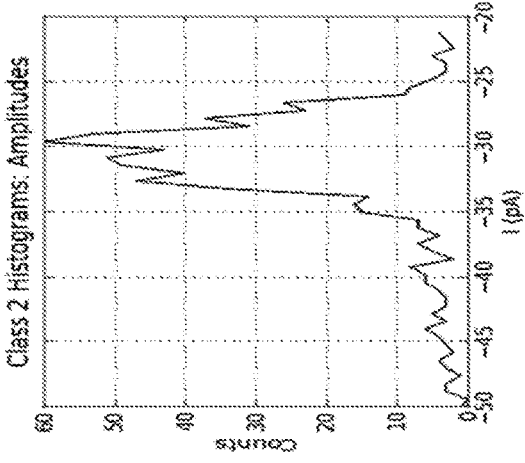
Figure 5A:
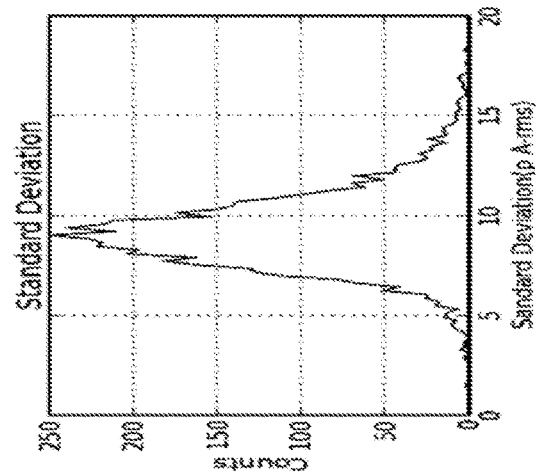
FIGS. 5A-F show histograms of translocations statistics for polyC100 translocating through alpha hemolysin polypeptide 4S+SDKMS (e.g., without the at least one native amino acid substituted with the non-native amino acid) (FIGS. 5A-5C; 2D density translocation statistics: Tmax=102 μsec and open channel=−238/+254 pA) and a modified alpha hemolysin polypeptide WY-4S SDKMS (FIGS. 5D-5F; 2D density translocation statistics: Tmax=919 μsec and open channel=−235/+251 pA).
Figure 5B:
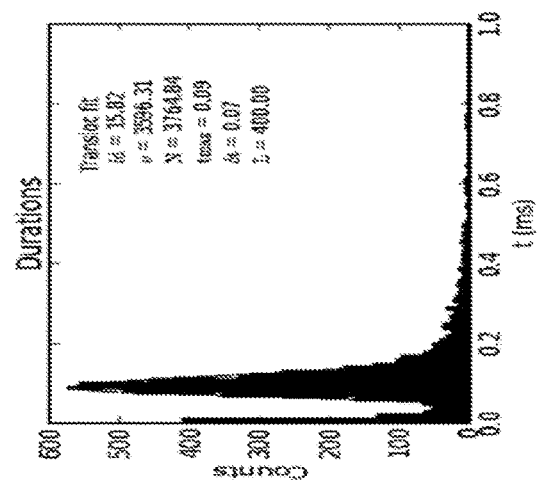
Figure 5C:
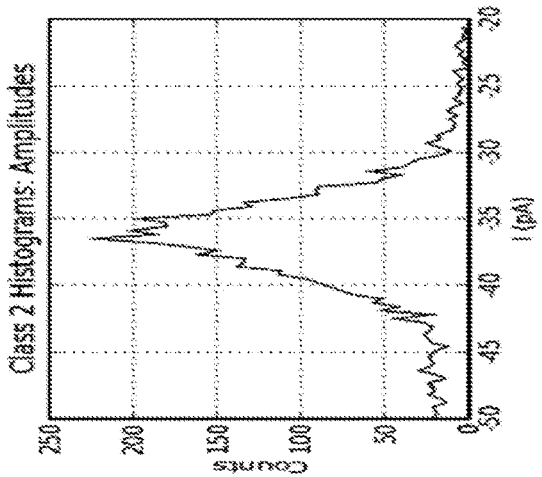
Figure 5D:
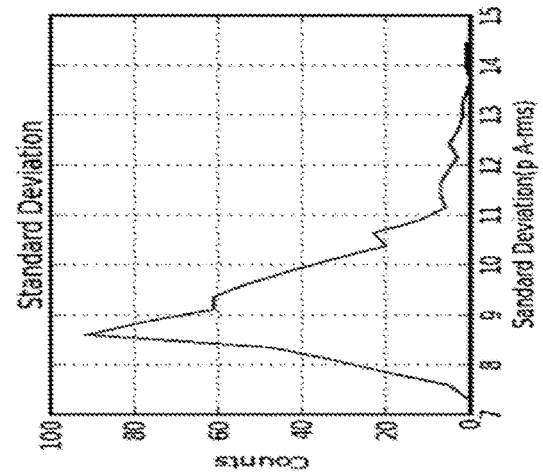
Figure 5E:
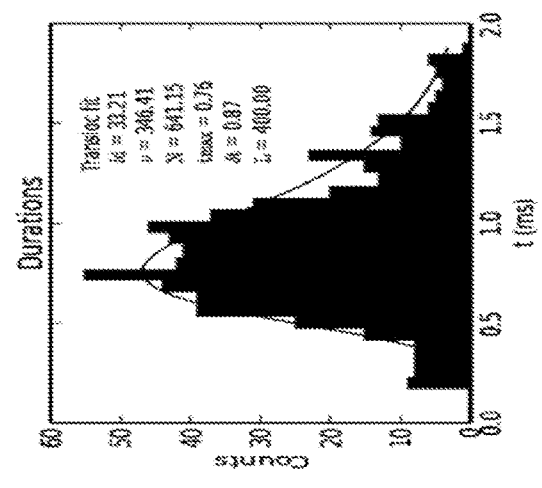
Figure 5F:
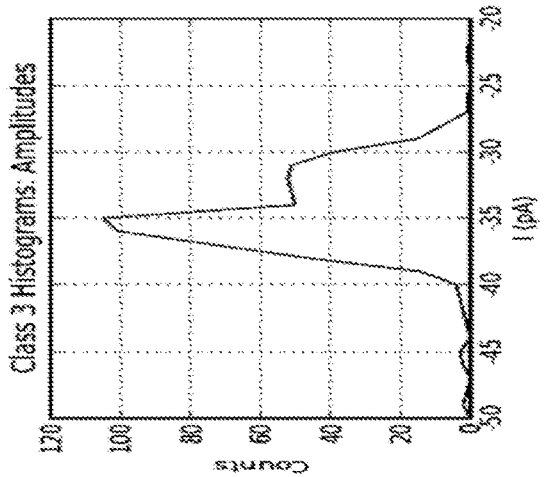
Figure 6A:
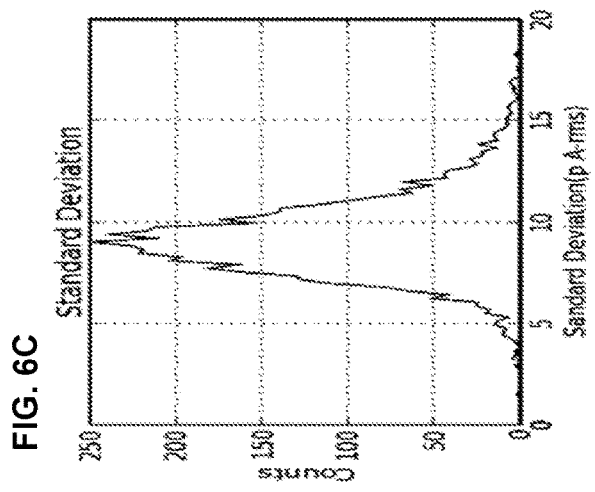
FIGS. 6A-F show histograms of translocations statistics for polyC100 translocating through alpha hemolysin polypeptide 4S+SDKMS (e.g., without the at least one native amino acid substituted with the non-native amino acid) (FIGS. 6A-6C; 2D density translocation statistics: Tmax=102 μsec and open channel=−238/+254 pA) and a modified alpha hemolysin polypeptide 107W T109W-4S SDKMS (FIGS. 6D-6F; 2D density translocation statistics: Tmax=249 μsec and open channel=−243/+259 pA).
Figure 6B:
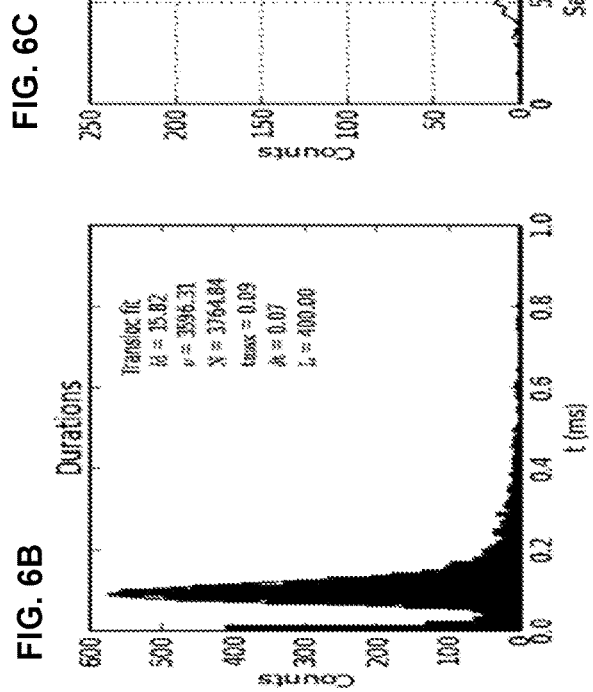
Figure 6C:
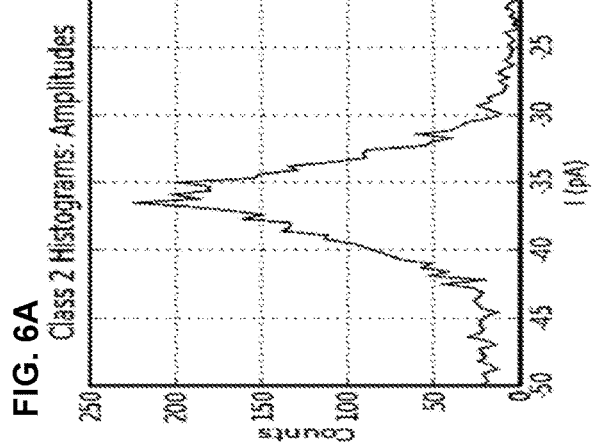
Figure 6D:
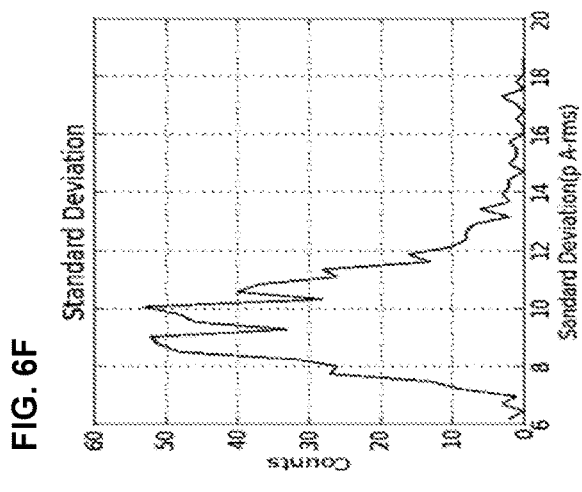
Figure 6E:
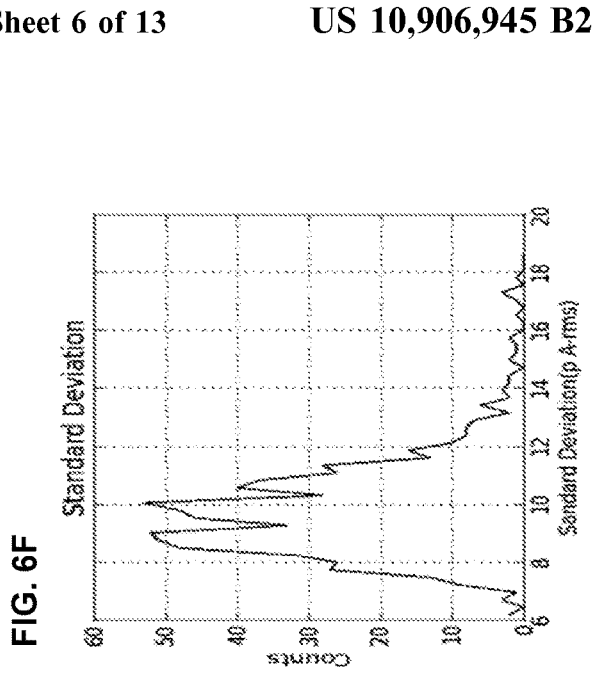
Figure 6F:
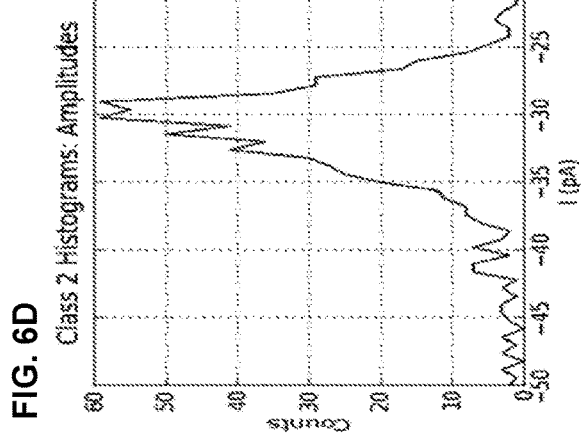
Figure 8C:
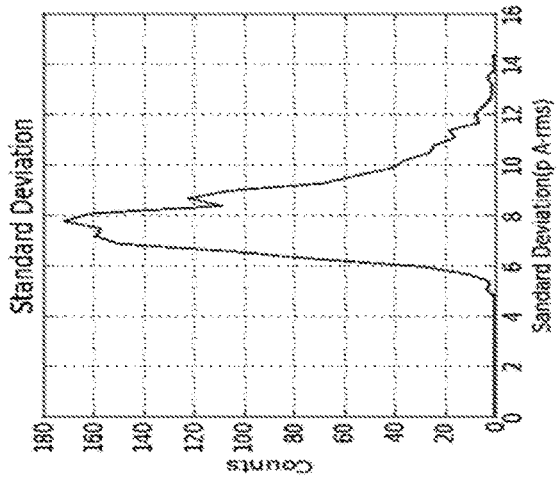
FIGS. 8A-F show histograms of translocations statistics for polyA100 translocating through alpha hemolysin polypeptide 4S L1351 T125Q D127K (e.g., without the at least one native amino acid substituted with the non-native amino acid) (FIGS. 8A-8C; 2D density translocation statistics: Tmax=278 μsec and open channel=−242/+275 pA) and a modified alpha hemolysin polypeptide YY-4S L1351 T125Q D127K (FIGS. 8D-8F; 2D density translocation statistics: Tmax=589 μsec and open channel=−230/+269 pA).
Figure 8B:
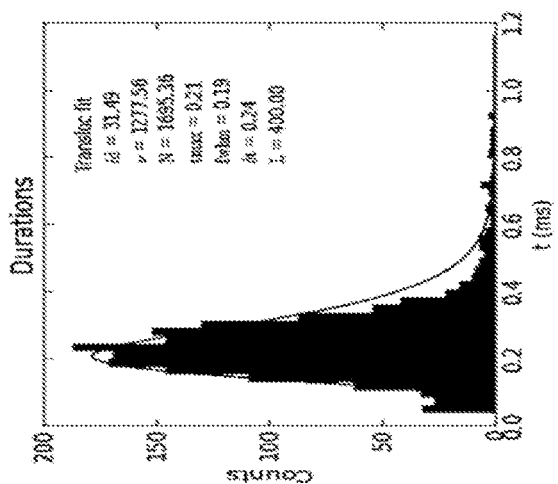
Figure 8A:
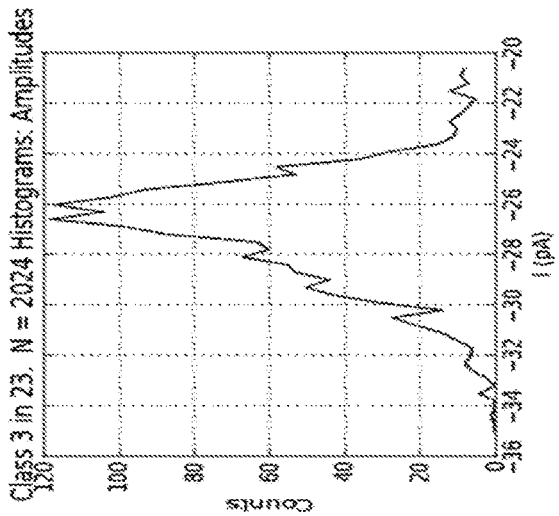
Figure 8F:
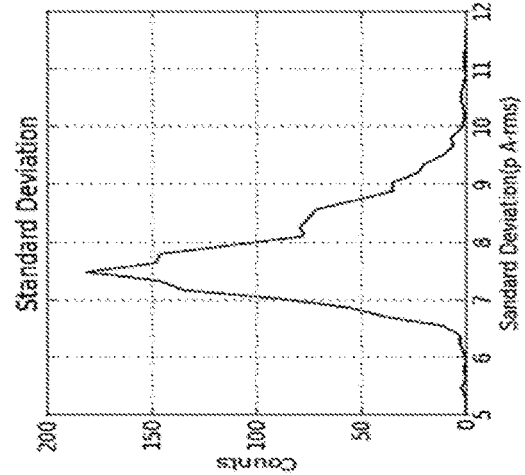
Figure 8E:
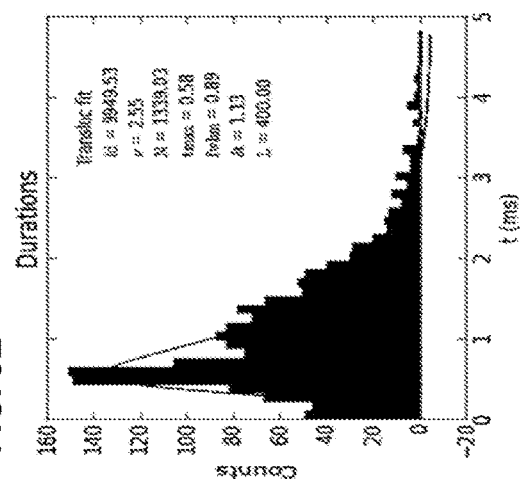
Figure 8D:
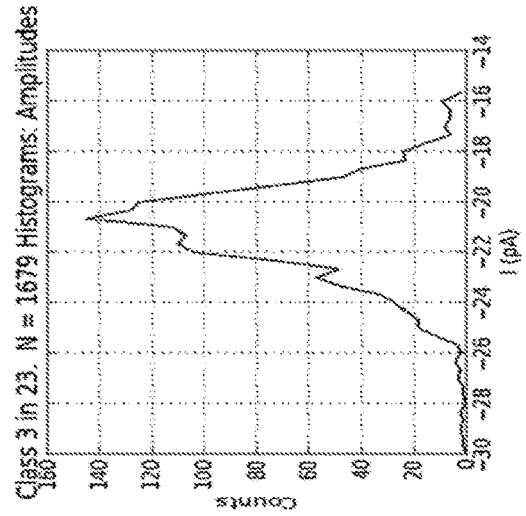
Figure 9A:
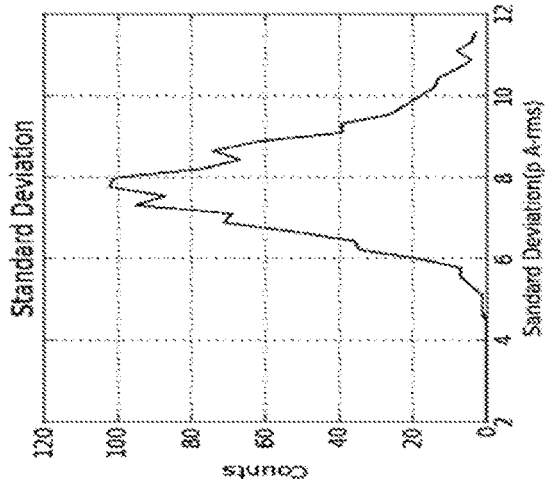
FIGS. 9A-F show histograms of translocations statistics for polyA100 translocating through alpha hemolysin polypeptide 4S L1351 T125S D127K (e.g., without the at least one native amino acid substituted with the non-native amino acid) (FIGS. 9A-9C; 2D density translocation statistics: Tmax=156 μsec and open channel=−234/+276 pA) and a modified alpha hemolysin polypeptide YY-4S L1351 T125S D127K (FIGS. 9D-9F; 2D density translocation statistics: Tmax=1170 μsec and open channel=−232/+278 pA).
Figure 9B:
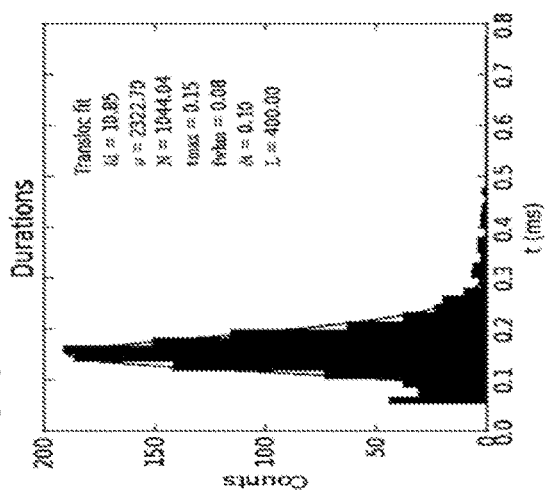
Figure 9C:
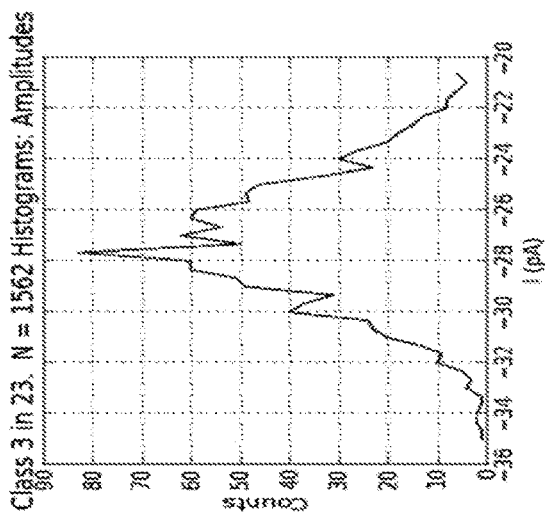
Figure 9D:
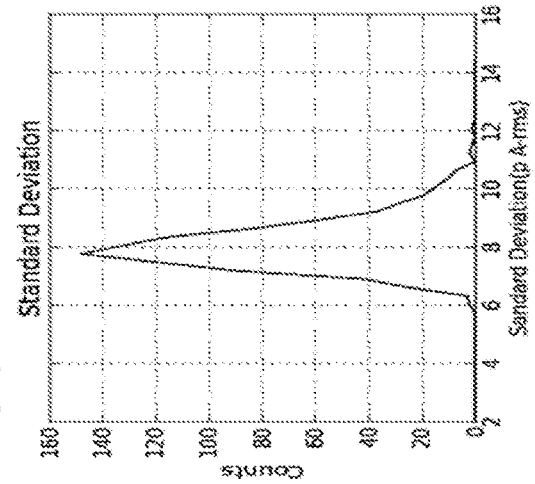
Figure 9E:
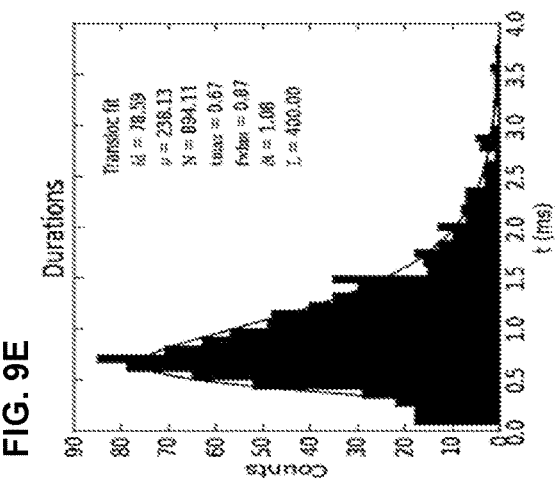
Figure 9F:
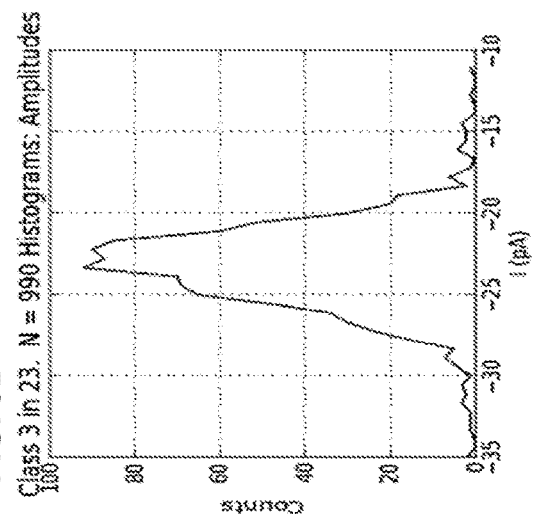
Figure 10A:
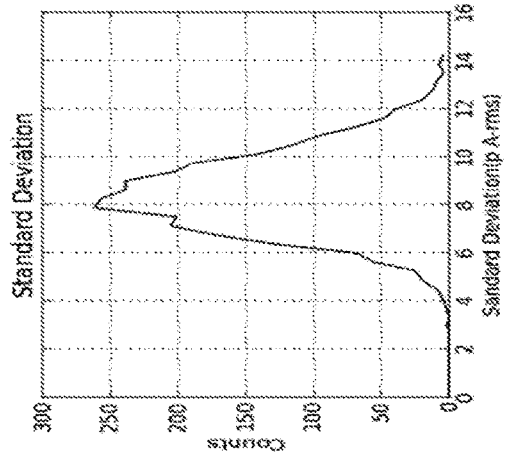
FIGS. 10A-F show histograms of translocations statistics for polyC100 translocating through alpha hemolysin polypeptide 4S L1351 T125S D127K (e.g., without the at least one native amino acid substituted with the non-native amino acid) (FIGS. 10A-10C; 2D density translocation statistics: Tmax=58 μsec and open channel=−235/+281 pA) and a modified alpha hemolysin polypeptide YY-4S L1351 T125S D127K (FIGS. 10D-10F; 2D density translocation statistics: Tmax=275 μsec and open channel=−241/+279 pA).
Figure 10B:
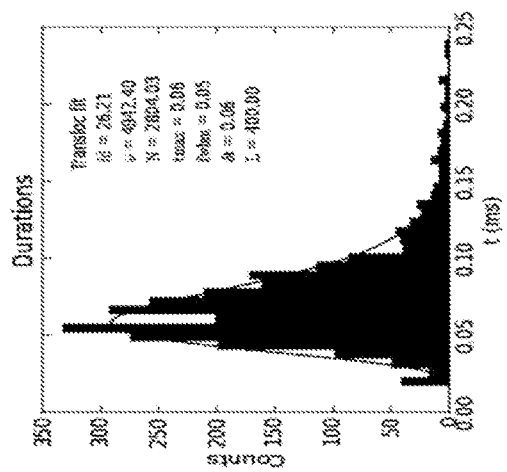
Figure 10C:
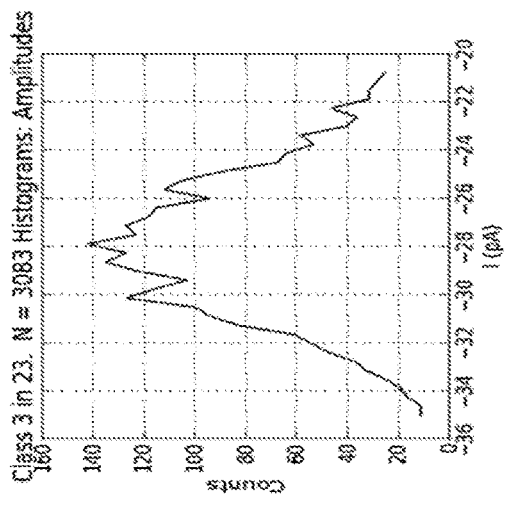
Figure 10D:
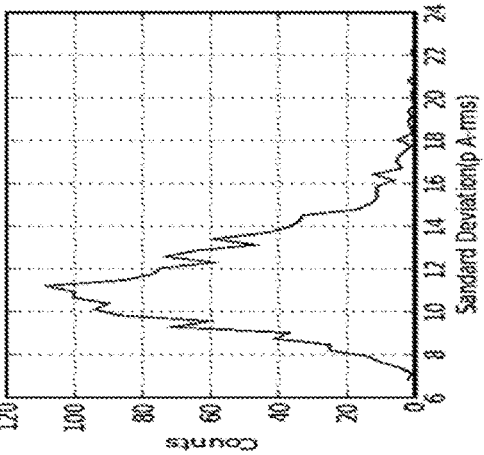
Figure 10E:
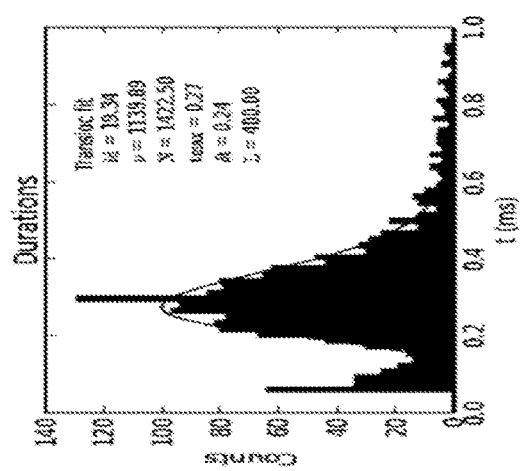
Figure 10F:
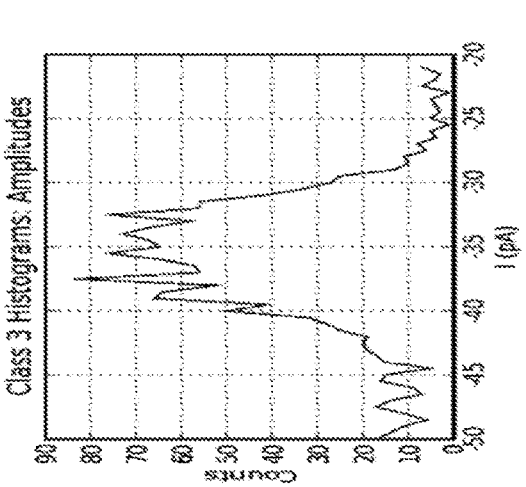
Figure 11A:
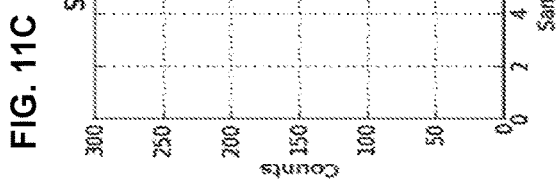
FIGS. 11A-F show histograms of translocations statistics for polyA100 translocating through alpha hemolysin polypeptide 4S N3T L1351 T125N D127K (e.g., without the at least one native amino acid substituted with the non-native amino acid) (FIGS. 11A-11C; 2D density translocation statistics: Tmax=163 μsec and open channel=−232/+278 pA) and a modified alpha hemolysin polypeptide YY-4S N3T L1351 T125N D127K (FIGS. 11D-11F; 2D density translocation statistics: Tmax=686 μsec and open channel=−240/+278 pA).
Figure 11B:
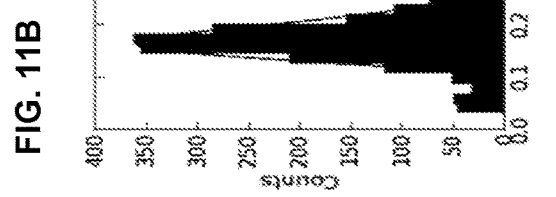
Figure 11C:
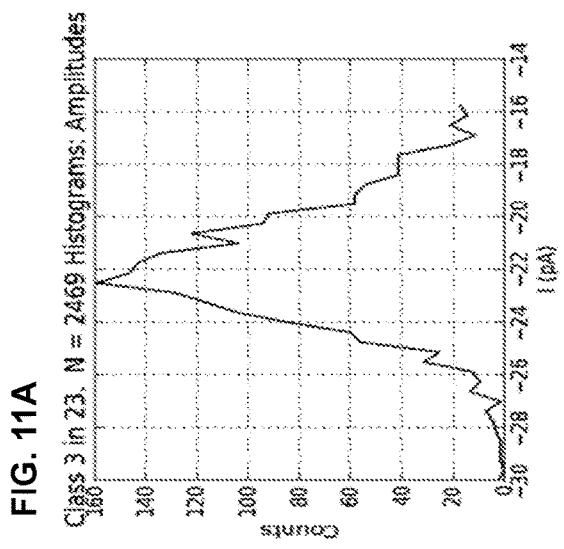
Figure 11D:
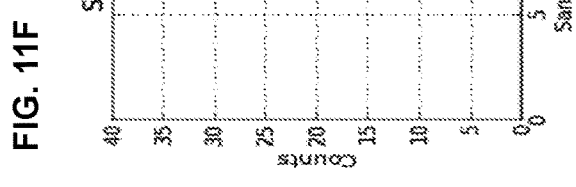
Figure 11E:
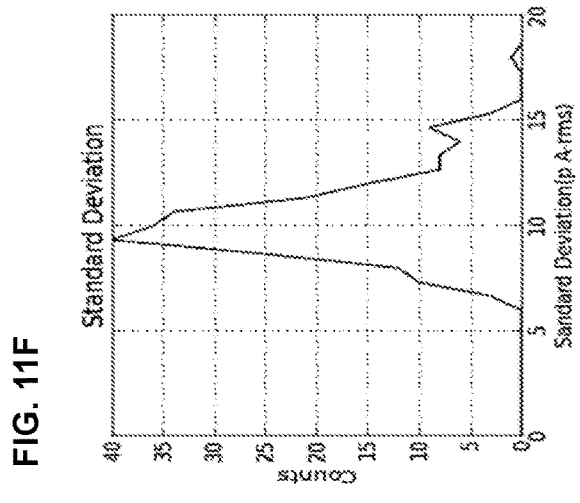
Figure 11F:
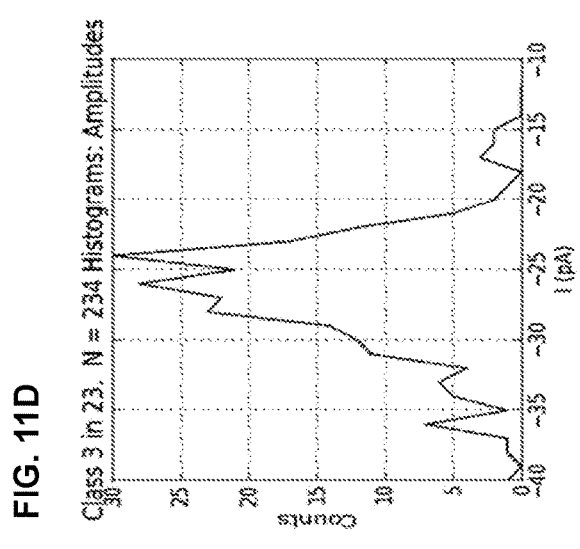
Figure 12A:
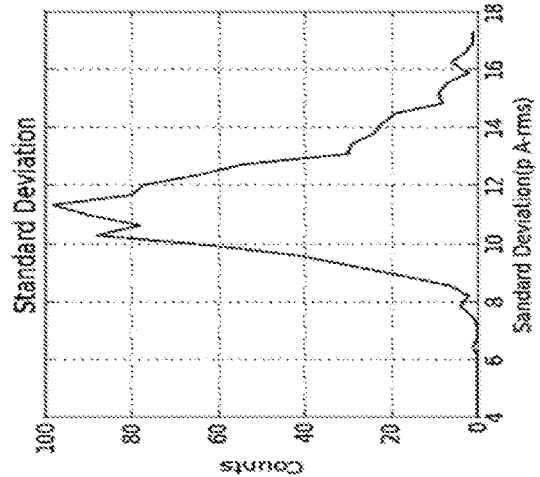
FIGS. 12A-F show histograms of translocations statistics for polyA100 translocating through alpha hemolysin polypeptide E111D M113S N2S L1351 D127K (e.g., without the at least one native amino acid substituted with the non-native amino acid) (FIGS. 12A-12C; 2D density translocation statistics: Tmax=169 μsec and open channel=−230/+247 pA) and a modified alpha hemolysin polypeptide YY-E111D M113S N2S L1351 D127K (FIGS. 12D-12F; 2D density translocation statistics: Tmax=400 μsec and open channel=−217/+238 pA).
Figure 12B:
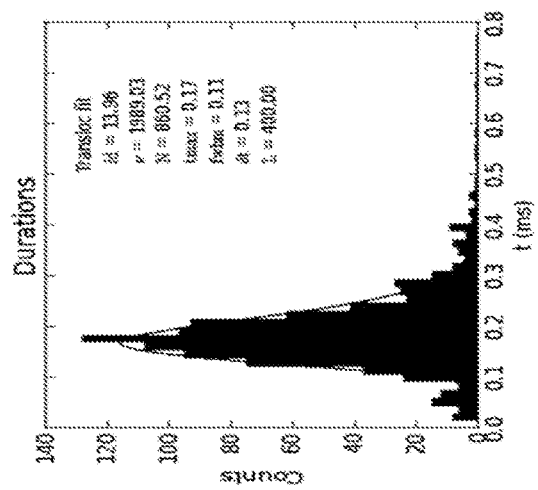
Figure 12C:
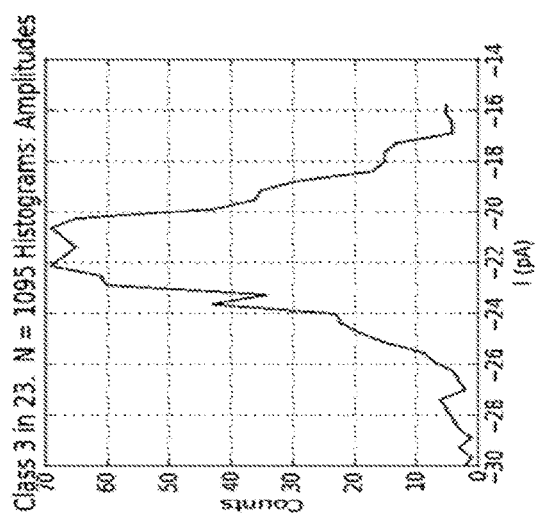
Figure 12D:
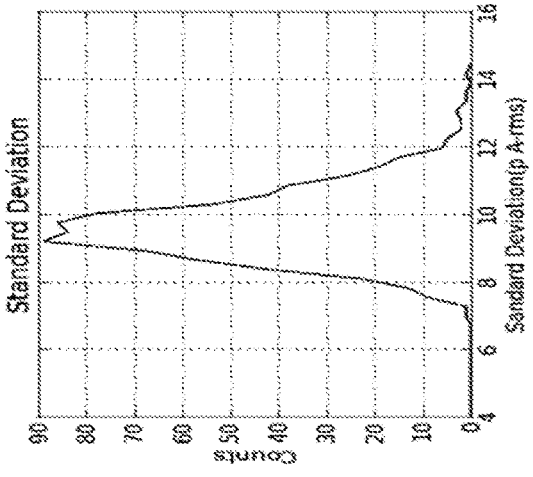
Figure 12E:
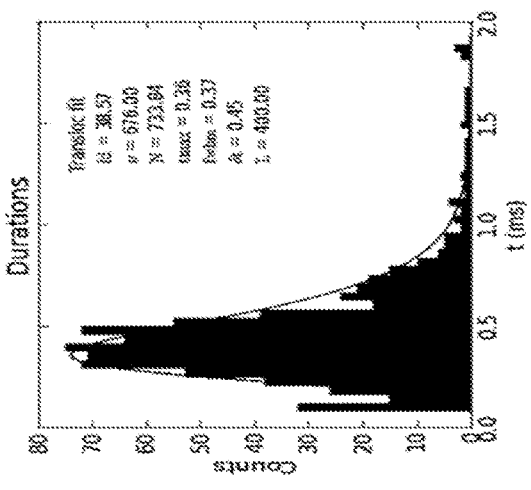
Figure 12F:
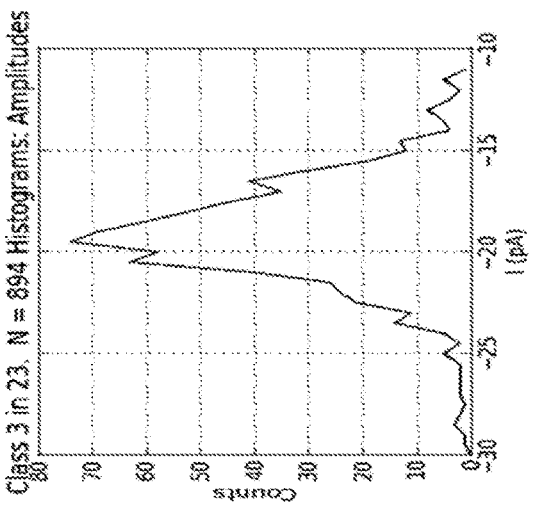
Figure 13A:
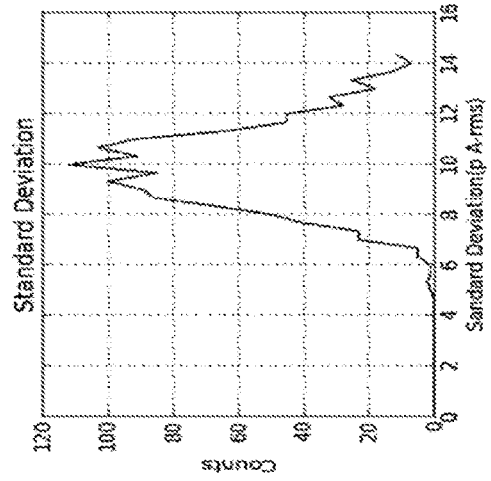
FIGS. 13A-F show histograms of translocations statistics for polyC100 translocating through alpha hemolysin polypeptide E111D M113S N2S L1351 D127K (e.g., without the at least one native amino acid substituted with the non-native amino acid) (FIGS. 13A-13C; 2D density translocation statistics: Tmax polyC100-3'=79 μsec and open channel=−240/+255 pA) and a modified alpha hemolysin polypeptide YY-E111D M113S N2S L1351 D127K (FIGS. 13D-13F; 2D density translocation statistics: Tmax polyC100-3'=314 μsec and open channel=−218/+242 pA).
Figure 13B:
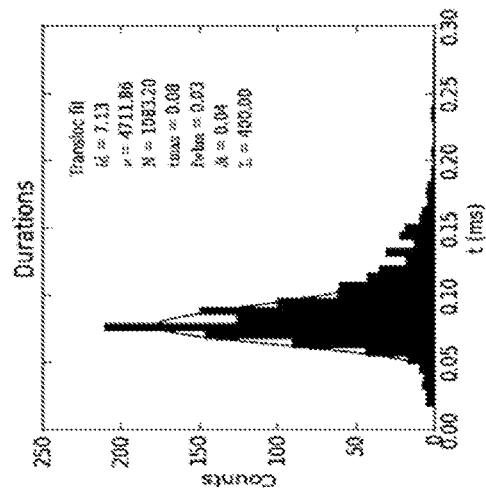
Figure 13C:
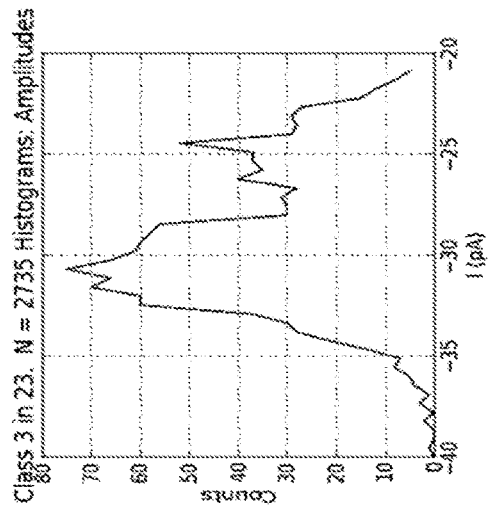
Figure 13D:
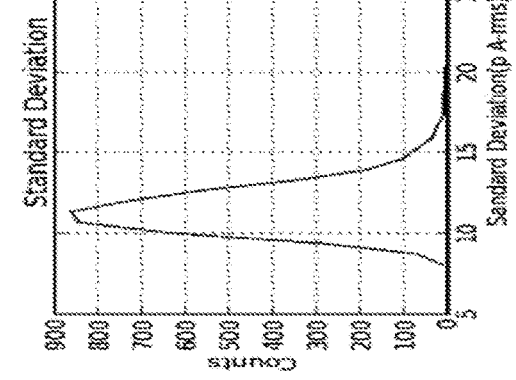
Figure 13E:
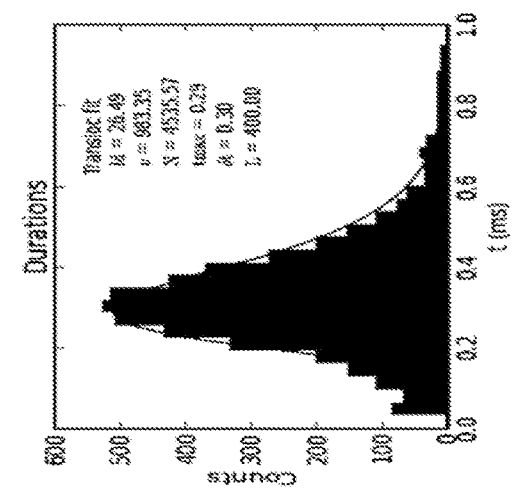
Figure 13F:
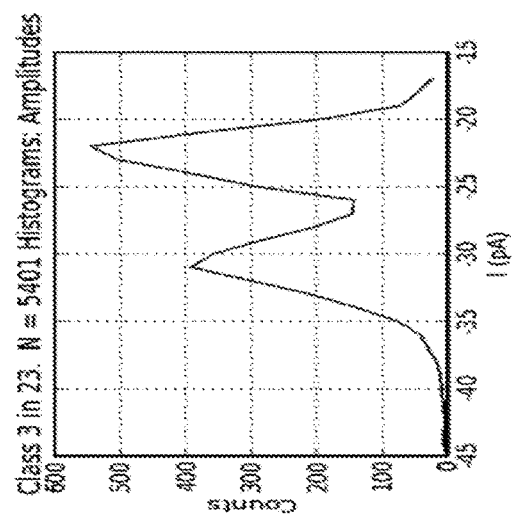

Hemolysins are exotoxins produced by bacteria that cause lysis of red blood cells in vitro or in vivo. Visualization of hemolysis of red blood cells in agar plates facilitates the categorization of some pathogenic bacteria such as Streptococcus and *Staphylococcus*. Although the lytic activity of some hemolysins on red blood cells may be important for nutrient acquisition or for causing certain conditions such as anemia, many hemolysin-producing pathogens do not cause significant lysis of red blood cells during infection. Although hemolysins are able to lyse red blood cells in vivo, the ability of hemolysins to target other cells, including white blood cells, often accounts for the effects of hemolysins in the host. Many hemolysins are pore forming proteins.

A non-limiting example of a hemolysin porin protein useful for insertion into lipid bilayers is alpha hemolysin, sometimes also referred to as alpha toxin. Alpha hemolysin forms a heptameric beta-barrel in biological membranes. Alpha hemolysin is secreted as a monomer that binds to the outer membrane of susceptible cells. Upon binding, the monomers oligomerize to form a water-filled transmembrane channel that facilitates uncontrolled permeation of water, ions, and small organic molecules. Rapid discharge of vital molecules, such as ATP, dissipation of the membrane potential and ionic gradients, and irreversible osmotic swelling leading to rupture or lysis of the cell wall, frequently causing death of the host cell. This pore-forming property has been identified as a major mechanism by which protein toxins cause damage to cells.

However, the ability to use wild-type hemolysin polypeptides for analysis of polymers (e.g., for polymer sequencing) presents certain technological challenges. For example, certain polymers translocate too quickly through a wild-type alpha hemolysin pore to be accurately analyzed or sequenced. Presented herein are modified alpha hemolysin polypeptides that demonstrate reduced rates of polymer translocation that can, for example, provide for more efficient and accurate analysis of translocating polymers.

An amino acid sequence of any suitable pore forming hemolysin protein, homologous protein, or pore forming portion thereof can be modified by methods described herein to generate a modified alpha hemolysin amino acid sequence. Non-limiting examples of pore forming hemolysins include listeriolysin O (e.g., from *Listeria monocytogenes*), alpha toxin or alpha hemolysin (e.g., from *Staphylococcus aureus*), PVL cytotoxin (e.g., from *Staphylococcus aureus*), cytolysin A (e.g., from *E. coli*), substantially homologous proteins thereof, pore forming portions thereof, the like and combinations thereof (e.g., chimeric variants thereof and/or heteromers thereof).

Polypeptides Comprising a Modified Alpha Hemolysin Amino Acid Sequence

In certain embodiments, a polypeptide comprises a modified alpha hemolysin amino acid sequence. In some embodiments, a polypeptide comprising a modified alpha hemolysin amino acid sequence is modified relative to a reference alpha hemolysin polypeptide. In some embodiments, a polypeptide comprising a modified alpha hemolysin amino acid sequence is modified relative to a wild type alpha hemolysin polypeptide. In some embodiments a modified alpha hemolysin amino acid sequence comprises an amino acid sequence of a wild-type alpha hemolysin protein or of a wild-type alpha hemolysin protein that has been modified. For example a modified alpha hemolysin protein may comprise one or more amino acid substitutions, deletions or insertions prior to being modified as described herein. A wild-type hemolysin protein can be any alpha hemolysin protein found in nature. In some embodiments a wild-type alpha hemolysin protein comprises an amino acid sequence with at least 70%, 75%, 80%, 85%, 90%, 95%, 96%, 97%, 98%, 99% sequence identity to the amino acid sequence of SEQ ID NO: 1. In some embodiments a wild-type alpha hemolysin protein comprises an amino acid sequence with at least 70%, 75%, 80%, 85%, 90%, 95%, 96%, 97%, 98%, 99% sequence homology to the amino acid sequence of SEQ ID NO: 1. In some embodiments a wild-type alpha hemolysin protein consists of an amino acid sequence of SEQ ID NO: 1.

In some embodiments a "modified alpha hemolysin amino acid sequence" refers to a modification of an amino acid sequence of an alpha hemolysin protein comprising one or more amino substitutions in a beta barrel region. The terms "modified alpha hemolysin polypeptide," "modified alpha hemolysin protein" and "modified alpha hemolysin protein pore" have the same meaning herein, are used interchangeably herein and refer herein to a protein (e.g., a polypeptide) comprising a modified alpha hemolysin amino acid sequence. A modified alpha hemolysin amino acid sequence can comprise any suitable modification of an amino acid sequence, non-limiting examples of which include one or more amino acid substitutions, amino acid modifications (e.g., substitution of an amino acid with a modified or non-standard amino acid), deletions of one or more amino acids, insertions of one or more amino acids, the like or combinations thereof. Standard amino acids include Alanine, Cysteine, Aspartic acid, Glutamic acid, Phenylalanine, Glycine, Histidine, Isoleucine, Lysine, Leucine, Methionine, Asparagine, Proline, Glutamine, Arginine, Serine, Threonine, Valine, Tryptophan and Tyrosine which can be represented herein by their standard IUPAC single letter or three letter abbreviations. Non-limiting examples of non-standard amino acids include α-Amino-n-butyric acid, Norvaline, Norleucine, Alloisoleucine, t-leucine, α-Amino-n-heptanoic acid, Pipecolic acid, α,β-diaminopropionic acid, α,γ-diaminobutyric acid, Ornithine, Allothreonine, Homocysteine, Homoserine, β-Alanine, β-Amino-n-butyric acid, β-Aminoisobutyric acid, γ-Aminobutyric acid, α-Aminoisobutyric acid, isovaline, Sarcosine, N-ethyl glycine, N-propyl glycine, N-isopropyl glycine, N-methyl alanine, N-ethyl alanine, N-methyl β-alanine, N-ethyl β-alanine, isoserine, α-hydroxy-γ-aminobutyric acid, Selenocysteine, Pyrrolysine and the like.

Methods of modifying an amino acid sequence are well known and described herein. Any suitable method can be used to modify an amino acid sequence of a polypeptide. In some embodiments a nucleotide sequence is modified, which modified nucleic acid is subsequently used to express a modified protein. Non-limiting examples of methods that can be used to modify a nucleic acid sequence included PCR based site directed mutagenesis techniques (e.g., overlap extension PCR, round the horn, site directed mutagenesis, the like and combinations thereof), chemical DNA synthesis, and methods described in Maniatis, T., E. F. Fritsch and J. Sambrook (1982) *Molecular Cloning: a Laboratory Manual*; Cold Spring Harbor Laboratory, Cold Spring Harbor, N.Y. Non-limiting examples of commercial kits that can be used to modify a nucleic acid sequence and/or amino acid sequence include QuickChange kit (Stratagene, San Diego, Calif., USA), Erase-a-base and pAlter-Max Vector (Promega, Sunnyvale, Calif., USA), In-Fusion® HD Plus Complete Cloning System (Clontech Laboratories, Inc., A Takara Bio Company, Mountain View, Calif., USA), GeneMorph® II EZClone Domain Mutagenesis Kit (Agilent Technologies, Santa Clara, Calif., USA), and Phusion Site-Directed Mutagenesis Kit (Thermo Scientific, Waltham, Mass. USA). A modified nucleic acid can be used to express a modified polypeptide comprising a modified amino acid sequence by any suitable method. Non-limiting examples of methods that can be used to generate a modified polypeptide comprising a modified amino acid sequence included Buculovirus expression systems, adenovirus expression systems, prokaryotic expression systems, phage expression systems, mammalian cell expression systems (e.g., 293 cell expression systems), yeast expression systems, in vitro translation systems, coupled in vitro transcription/translation systems, the like and combinations thereof. Non-limiting examples of commercial protein expression systems that can be used to express a modified polypeptide comprising a modified polypeptide amino acid sequence include Gateway Nova, pET expression systems and Bac Magic expression systems (EMD Millipore, Temecula, Calif. USA), VariFlex expression systems (Agilent Technologies, Santa Clara, Calif., USA) and Bac-to-Bac Baculovirus Expression System, ViraPower Adenoviral Gateway Expression Kit, Expressway Maxi Cell-Free *E. coli* Expression System, and Retic Lysate IVT Kit (Life Technologies, Carlsbad, Calif. USA).

In some embodiments, a modified alpha hemolysin amino acid sequence is modified in reference to the 293 amino acid sequence of an unmodified alpha hemolysin, provided herein as SEQ ID NO: 1. In some embodiments, a modified alpha hemolysin amino acid sequence is modified in reference to the positions, or aligned positions, of the 293 amino acids of alpha hemolysin of SEQ ID NO: 1. An amino acid in a modified amino acid sequence generally "corresponds to" an aligned amino acid when the modified amino acid sequence is aligned to the amino acid sequence of SEQ ID NO: 1. For example, a modification may comprise substitution of amino acid 109 of SEQ ID NO: 1 where any amino acid pre-existing at position 109 is substituted. In certain embodiments, modified amino acids are noted by their positions corresponding to the sequence in SEQ ID NO:1. For example, a native amino acid threonine at position 109 in SEQ ID NO:1 can be referred to as T109. In the foregoing example, native amino acid T109 can be substituted with the non-native amino acid tyrosine (Y), and this substitution is noted as T109Y. In certain embodiments, a portion of the alpha hemolysin polypeptide may be truncated. For example, the first 50 amino acids could be removed in an altered version of the protein pore, thus the protein pore would only have 243 amino acids and positions rather than the normal 293. In this case, the modifications are still made in reference to the original SEQ ID NO:1. For example, in the truncated example, amino acid 59 would correspond to 109 in the original SEQ ID NO: 1. Thus, if native amino acid 59 of the truncated protein pore was substituted with a non-native amino acid, it would still correspond to 109 of the original sequence and be covered by this patent application. A native amino acid can be an amino acid found at a specific position within a sequence of a wild type hemolysin protein (e.g., the protein of SEQ ID NO: 1). The term "native amino acid substitution" as used herein, and/or any reference herein to substitution of a "native amino acid" refers to substitution or replacement of a native amino acid with another amino acid that is different than the native amino acid. A non-native amino acid can be a standard or non-standard amino acid that is different than a native amino acid found at a specific position within a sequence of a wild type hemolysin protein (e.g., the protein of SEQ ID NO: 1).

As used herein, the terms "aligned", "alignment", or "aligning" refer to two or more nucleic acid sequences that can be identified as a match (e.g., 100% identity) or partial match. Alignments can be done manually or by a computer algorithm, examples including the Efficient Local Alignment of Nucleotide Data (ELAND) computer program distributed as part of the Illumina Genomics Analysis pipeline. The alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In some cases a nucleic acid sequence is aligned with the reverse complement of another nucleic acid sequence.

An alignment often is used to determine sequence identity or homology. Sequence identity (e.g., percent sequence identity) and/or homology (e.g., percent homology) can be determined by any suitable alignment program or algorithm. Percent sequence identity often refers to the amount of amino acids that match divided by the total amount of amino acids aligned for two polypeptide sequences. Percent sequence homology is often determined to compare two polypeptide sequences that may comprises gap and/or inserts and often algorithms used for a homology determination weight amino acid alignments, in part, according to conservative and/or non-conservative substitutions.

Exemplary computer programs which can be used to determine identity between two sequences include, but are not limited to, the suite of BLAST programs, e.g., BLASTX and BLASTP, publicly available on the Internet at the NCBI website. Sequence searches are typically carried out using the BLASTP program when evaluating a given amino acid sequence relative to amino acid sequences in the GenBank Protein Sequences and other public databases. Both BLASTP and BLASTX can run using default parameters of an open gap penalty of 11.0, and an extended gap penalty of 1.0, and utilize a BLOSUM-62 matrix, for example.

In certain embodiments, the modified alpha hemolysin amino acid sequence comprises one or more native amino acid substitutions at one or more positions corresponding to positions 1-109 and 149-293 of SEQ ID NO: 1. In certain embodiments, the modified alpha hemolysin amino acid sequence comprises one or more native amino acid substitutions at one or more positions corresponding to positions 1, 2, 3, 4, 5, 6, 7, 8, 9, 10, 11, 12, 13, 14, 15, 16, 97, 99, 101, 103, 105, 107, 109, 149, 151, 153, 155, 157, 159, 161, 163, 165, 167, 169, 225, 227, 229, 231 or 233 of SEQ ID NO: 1. In certain embodiments, the modified alpha hemolysin amino acid sequence comprises one or more native amino acid substitutions at one or more positions corresponding to positions 105, 107, 109, 149, 151 or 153 of SEQ ID NO: 1. In certain embodiments, the modified alpha hemolysin amino acid sequence comprises one or more native amino acid substitutions at one or more of positions corresponding to positions 107, 109, 149, or 151 of SEQ ID NO: 1. In certain embodiments, the modified alpha hemolysin amino acid sequence comprises one or more native amino acid substitutions at one or more positions corresponding to positions 109 or 149 of SEQ ID NO: 1.

In some embodiments herein, a polypeptide (e.g., a modified alpha hemolysin protein) is an isolated polypeptide. An isolated polypeptide can be isolated by a suitable isolation process known in the art. A polypeptide or isolated polypeptide sometimes is provided as a purified polypeptide, a partially purified polypeptide, an enriched polypeptide, an expressed polypeptide (e.g., an over-expressed polypeptide), a synthetic polypeptide (e.g., made by a chemical process, made by an in vitro process) or the like. An expressed polypeptide can be expressed by any suitable method. An expressed polypeptide can be expressed in vitro (e.g., by an in vitro transcription and/or translation system), in situ and/or in vivo by any suitable method. For example an expressed polypeptide can be expressed using a suitable cell expression method or system. An isolated protein can be in the form of a lysate (cell, phage or bacterial lysate or virus lysate), cell or nuclear extract and/or a secretion product (e.g., in the form of conditioned media or spent broth).

The term "isolated" as used herein refers to polypeptide (e.g., a protein, or portion thereof) removed from its original environment (e.g., the natural environment if it is naturally occurring, or a host cell if expressed exogenously), and thus is altered by human intervention (e.g., "by the hand of man") from its original environment. An isolated polypeptide can be a polypeptide removed from a subject (e.g., a human subject). An isolated polypeptide can be provided with fewer non-polypeptide components (e.g., nucleic acids, lipids, carbohydrates) than the amount of components present in a source sample. An isolated polypeptide can be provided with fewer contaminating polypeptide components (e.g., where contaminating polypeptides are different polypeptides than the polypeptide intended to be isolated, e.g., different than the isolated polypeptide) than the amount of contaminating components present in a source sample. A composition comprising an isolated polypeptide can be about 50% to greater than 99% free of non-polypeptide components and/or contaminating polypeptide components. A composition comprising an isolated polypeptide can be about 90%, 91%, 92%, 93%, 94%, 95%, 96%, 97%, 98%, 99% or greater than 99% free of non-polypeptide components and/or contaminating polypeptide components. A composition comprising an isolated polypeptide can contains fewer polypeptide species than in the sample source from which the polypeptide is derived. A composition comprising an isolated polypeptide may be about 90%, 91%, 92%, 93%, 94%, 95%, 96%, 97%, 98%, 99% or greater than 99% free of other polypeptide species. An isolated polypeptide can be provided in a mixture of polypeptides species (e.g., an expression extract) where the isolated polypeptide comprises greater than 5%, 10%, 20%, 30%, 40%, 50% of the total protein content of the mixture. For example, an isolated protein can be generated in an in vitro translation expression system and can be used in a nanopore device with or without further purification.

The term "purified" as used herein can refer to a polypeptide provided that contains fewer non-polypeptide components and/or contaminating polypeptide components (e.g., where contaminating polypeptides are different polypeptides than the polypeptide intended to be purified, e.g., different than the purified polypeptide) than the amount of non-polypeptide components and/or contaminating polypeptide components present prior to subjecting the polypeptide to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of non-polypeptide components and/or contaminating polypeptide components. The term "purified" as used herein can refer to a polypeptide provided that contains fewer polypeptide species than in the sample source from which the polypeptide is derived. A composition comprising purified polypeptide may be about 90%, 91%, 92%, 93%, 94%, 95%, 96%, 97%, 98%, 99% or greater than 99% free of other polypeptide species. For example, an exogenously expressed protein can be purified from a mixture comprising endogenously expressed portions.

Types of Non-Native Amino Acid Substitutions

In some embodiments, the at least one native amino acid substituted with a non-native amino acid is substituted with a non-native amino acid that is hydrophobic. In some embodiments, the at least one native amino acid substituted with a non-native amino acid is substituted with a non-native amino acid that is aromatic. In some embodiments, the at least one native amino acid substituted with a non-native amino acid is substituted with a non-native amino acid that is hydrophobic and aromatic. In some embodiments, the at least one native amino acid substituted with a non-native amino acid is substituted with a non-native amino acid that is larger than the native amino acid.

In certain embodiments, the non-native amino acid is naturally occurring. A naturally occurring amino acid can be any suitable standard amino acid or non-standard amino acid that is found in nature and can be found in a naturally occurring polymer (e.g., a naturally occurring polypeptide or polynucleotide). In certain embodiments, a non-native amino acid is synthetic. In certain embodiments, the non-native amino acid is hydrophobic and is methionine (M). In certain embodiments, the non-native amino acid is hydrophobic and aromatic and is phenylalanine (F), tryptophan (W) or tyrosine (Y).

In certain embodiments, at least two native amino acids are substituted with non-native amino acids that are independently selected as hydrophobic, aromatic or hydrophobic and aromatic. For example, the native amino acid threonine at position 109 (T109) is substituted with the hydrophobic and aromatic non-native amino acid tyrosine (Y), thus T109Y while the native amino acid valine (V) at position 149 (V149) is substituted with the hydrophobic amino acid methionine (M), thus V149M. In certain embodiments, at least three native amino acids are substituted with non-native amino acids that are independently selected as hydrophobic, aromatic or hydrophobic and aromatic. In certain embodiments, at least four native amino acids are substituted with non-native amino acids that are independently selected as hydrophobic, aromatic or hydrophobic and aromatic. In certain embodiments, at least five native amino acids are substituted with non-native amino acids that are independently selected as hydrophobic, aromatic or hydrophobic and aromatic. In certain embodiments, at least one of the native amino acids are substituted with non-native amino acids that are independently selected as hydrophobic, aromatic or hydrophobic and aromatic. In some embodiments, at least one of the native amino acids is substituted with a non-native amino acid that is not hydrophobic, aromatic or hydrophobic and aromatic as long as at least one of the native amino acids is substituted with a non-native amino acid that is hydrophobic, aromatic or hydrophobic and aromatic.

In certain embodiments, the at least two native amino acids substituted with non-native amino acids are substituted with the same non-native amino acid. For example, native amino acids T109 and V149 are both substituted with the non-native amino acid Y. In certain embodiments, the at least two native amino acids substituted with non-native amino acids are substituted with non-native amino acids that are not the same. For example, native amino acid isoleucine (I) at position 107 (I107) is substituted with the non-native amino acid tryptophan (W) while the native amino acid V149 is substituted with the non-native amino acid Y, thus noted as I107W and V149Y.

In certain embodiments, the at least three native amino acids substituted with non-native amino acids are substituted with non-native amino acids that are not the same. For example, native amino acids I107, T109 and V149 are substituted with the non-native amino acids, M, W and Y respectively. In certain embodiments, at least two of the at least three native amino acids substituted with non-native amino acids are substituted with the same non-native amino acid. For example, native amino acids I107, T109 and V149 are substituted with the non-native amino acids, W, W and Y respectively.

In some embodiments a substitution is a conservative substitution. Conservative amino acid substitutions are known in the art. A conservative substitution often comprises substitution of a first amino acid with a different second amino acid where the first and second amino acids comprise similar physical properties (e.g., charge, size, hydrophobicity, the like). Non-limiting examples of conservative substitutions include replacing a hydrophobic amino acid (e.g., leucine) with different hydrophobic amino acid (e.g., valine), replacing a basic amino (e.g., lysine) with a different basic amino acid (e.g., arginine), and replacing a small flexible amino acid (e.g., glycine) with another small flexible amino acid (e.g., serine) or the like. In some embodiments a substitution is a non-conservative substitution where a first amino acid is substituted with another second amino acid where the first and second amino acids comprise substantially different physical properties.

Beta Barrel Amino Acids

In certain embodiments, a modified alpha hemolysin amino acid sequence comprises one or more amino substitutions located in a beta barrel (e.g., in a beta barrel region). In certain embodiments, a substitution in a beta barrel is chosen from one or more of positions 111, 113, 115, 117, 119, 121, 123, 125, 127, 129, 131, 133, 135, 137, 139, 141, 143, 145 and 147 of SEQ ID NO: 1. An amino acid located in a beta barrel is often referred to herein as a beta barrel amino acid. In certain embodiments, at least two, at least three, at least four, at least five, at least six, at least seven or at least eight beta barrel amino acids of a modified alpha hemolysin polypeptide are substituted (e.g., replaced) with different amino acids. In some embodiments a modified alpha hemolysin protein comprises 1, 2, 3, 4, 5, 6, 7, 8, 9, 10, 11, 12, 13, 14, 15, 16, 17, 18 or 19 amino acid substitutions located in a beta barrel. For example, the native amino acid T109 of wild type alpha hemolysin is sometimes substituted with a non-native amino acid Y and the beta barrel amino acid glutamic acid (E) at position 111 is replaced with the different amino acid serine (S), thus termed T109Y E111S. In certain embodiments, the different amino acid is a naturally occurring amino acid. In certain embodiments, the different amino acid is a synthetic amino acid.

In certain embodiments, a polypeptide comprising a modified alpha hemolysin amino acid sequence comprises the native amino acids T109 and V149 substituted with the non-native amino acid tyrosine (T109Y and V149Y) and the beta barrel amino acids E111, M113, D127, L135, T145 and K147 replaced with the different amino acids serine, serine, lysine, isoleucine, serine and serine respectively (E111S, M113S, D127K, L135I, T145S, and K147S), SEQ ID NO: 2.

In certain embodiments, a polypeptide comprising a modified alpha hemolysin amino acid sequence comprises the native amino acids T109 and V149 substituted with the non-native amino acids tyrosine and tryptophan (W) respectively (T109Y and V149W) and the beta barrel amino acids E111, M113, D127, L135, T145 and K147 replaced with the different amino acids serine, serine, lysine, isoleucine, serine and serine respectively (E111S, M113S, D127K, L135I, T145S, and K147S).

In some embodiments, a polypeptide comprising a modified alpha hemolysin amino acid sequence comprises the native amino acids T109 and V149 substituted with the non-native amino acid tyrosine (T109Y and V149Y) and the beta barrel amino acids E111, M113, L135, T145 and K147 replaced with the different amino acids serine, serine, isoleucine, serine and serine respectively (E111S, M113S, L135I, T145S, and K147S), SEQ ID NO: 3.

In certain embodiments, a polypeptide comprising a modified alpha hemolysin amino acid sequence comprises the native amino acids T109 and V149 substituted with the non-native amino acids tyrosine and tryptophan (W) respectively (T109Y and V149W) and the beta barrel amino acids E111, M113, D127, L135, T145 and K147 replaced with the different amino acids serine, serine, isoleucine, serine and serine respectively (E111S, M113S, L135I, T145S, and K147S).

Polymer

A polymer, as referred to herein, can be any molecular polymer. Some common molecular polymers are polynucleotides and polypeptides. A polymer can be a nucleic acid polymer, a protein polymer or a peptide polymer. A polymer can be a single stranded or double stranded nucleic acid. A polymer can be a single stranded or double stranded DNA or RNA. A polymer can be a protein or peptide. Non-limiting examples of a polymer include a single stranded DNA, a double stranded DNA, a single stranded RNA, a double stranded RNA, a protein and a peptide. In certain embodiments, the polymer is single stranded DNA. In certain embodiments, the polymer is double stranded DNA. A polymer can include one or more sections and a polymer section can include at least a portion of a monomer.

A monomer, as referred to herein, can be any molecule that can be linked chemically to another molecule to form a polymer. A monomer can be a nucleic acid or amino acid, for example. A monomer can be naturally occurring, modified or synthetic. A synthetic monomer is often a monomer that is not found in a naturally occurring polymer. A naturally occurring polymer is often generated in nature, in vivo, by an un-altered or un-modified organism. In some embodiments a synthetic monomer is a synthetic amino acid or synthetic nucleotide. A nucleic acid monomer can be phosphorylated, oxidized, acetylated, methylated or sulfonated. A nucleic acid monomer can be a monophosphate nucleotide, modified nucleotide, methylated nucleotide, acetylated nucleotide or oxidized nucleotide. Non-limiting examples of a monomer include nucleotides, monophosphate nucleotides, modified nucleotides, methylated nucleotides and oxidized nucleotides. Non-limiting examples of a nucleic acid monomer include adenine (A), cytosine (C), thymine (T), guanine (G), uracil (U), modified cytosine, 7-methylguanine, xanthine, hypoxanthine, 5,6-dihydrouracil, 5-methylcytosine, N4-methylcytosine, hydroxymethylcytosine, or N6-methyladenine.

A single stranded polynucleotide consisting of a certain nucleotide monomer (N) is referred to herein as polyN, polyNi or polyNiNi where i indicates the number of monomers in a polynucleotide. For example, a single stranded polynucleotide consisting of adenine monomers can be referred to herein as a polyA, a polynucleotide of cytosine monomers can be referred to herein as polyC, a polynucleotide of thymine monomers can be referred to herein as polyT, and a polynucleotide of guanine monomers can be referred to as polyG. For example, a polymer that is single stranded DNA consisting of 100 cytosine (C) bases is referred to herein as polyC100. A polymer that is single stranded DNA consisting of 50 cytosine bases followed by 50 adenine (A) bases is referred to herein as polyC50A50, for example.

Polymer Slowing

In certain embodiments, a polypeptide comprising a modified alpha hemolysin amino acid sequence that comprises at least one amino acid substituted with a non-native amino acid forms a modified alpha hemolysin polypeptide. In certain embodiments, a modified alpha hemolysin polypeptide enables a polymer to at least partially translocate through the modified alpha hemolysin polypeptide. In certain embodiments, the translocation time of a polymer through a modified alpha hemolysin polypeptide is increased relative to the translocation time of the same polymer through a reference alpha hemolysin polypeptide.

A reference alpha hemolysin polypeptide sometimes is modified relative to a wild type counterpart of the pore, and often the reference alpha hemolysin polypeptide is an unmodified wild type protein pore. A reference alpha hemolysin polypeptide can be an unmodified or modified wild type alpha hemolysin polypeptide. In some embodiments a reference alpha hemolysin polypeptide comprises an amino acid sequence comprising at least 75%, 80%, 85%, 90%, 95%, 96%, 97%, 98%, or at least 99% identity to SEQ ID NO: 1. In some embodiments a reference alpha hemolysin polypeptide consists of the amino acid sequence of SEQ ID NO: 1. In some embodiments a reference alpha hemolysin polypeptide comprises an amino acid sequence comprising at least 75%, 80%, 85%, 90%, 95%, 96%, 97%, 98%, 99% or 100% homology to SEQ ID NO: 1. In some embodiments a reference alpha hemolysin polypeptide comprises 1, 2, 3, 4, 5, 6, 7, 8, 9, 10, 11, 12, 13, 14,15, 16, 17, 18, 19 or 20 or more amino acid substitutions relative to SEQ ID NO: 1. In some embodiments a reference alpha hemolysin protein comprises an alpha hemolysin amino acid sequence comprising one or more amino acid modifications in addition to one or more native amino acid substitutions described herein for a modified alpha hemolysin polypeptide. In certain embodiments, a reference alpha hemolysin protein comprises one or more amino acid substitutions, deletions or insertions in a beta barrel region of an alpha hemolysin protein. In some embodiments a reference alpha hemolysin polypeptide comprises one or more amino acid substitution at one or more positions corresponding to positions 111, 113, 115, 117, 119, 121, 123, 125, 127, 129, 131, 133, 135, 137, 139, 141, 143, 145 or 147 of SEQ ID NO: 1. In some embodiments a reference alpha hemolysin polypeptide does not comprise an amino acid substitution at one or more positions corresponding to positions 1, 2, 3, 4, 5, 6, 7, 8, 9, 10, 11, 12, 13, 14, 15, 16, 97, 99, 101, 103, 105, 107, 109, 149, 151, 153, 155, 157, 159, 161, 163, 165, 167, 169, 225, 227, 229, 231 or 233 of SEQ ID NO: 1. In some embodiments a reference alpha hemolysin polypeptide does not comprise an amino acid substitution at one or more positions corresponding to positions 105, 107, 109, 149, 151 or 153 of SEQ ID NO: 1. In some embodiments a reference alpha hemolysin polypeptide does not comprise an amino acid substitution at one or more positions corresponding to positions 1, 2, 3, 4, 5, 6, 7, 8, 9, 10, 11, 12, 13, 14, 15, 16, 97, 99, 101, 103, 105, 107, 109, 149, 151, 153, 155, 157, 159, 161, 163, 165, 167, 169, 225, 227, 229, 231 or 233 of SEQ ID NO: 1, where the amino acid substitution independently is to a non-native hydrophobic amino acid or non-native aromatic amino acid, or non-native aromatic and hydrophobic amino acid.

A translocation time of a polymer (e.g., a polynucleotide, a polypeptide) through a modified alpha hemolysin polypeptide can be determined (e.g., measured) and compared to a translocation time of the same polymer through another alpha hemolysin polypeptide (e.g., a wild type alpha hemolysin polypeptide, a reference alpha hemolysin polypeptide). For example, a translocation time for a wild type alpha hemolysin polypeptide, such as an alpha hemolysin polypeptide having the amino acid sequence of SEQ ID NO: 1, is compared to the translocation time of a modified alpha hemolysin polypeptide counterpart (e.g., a modified alpha hemolysin polypeptide described herein. In some embodiments a polymer translocates through a modified alpha hemolysin polypeptide at a slower rate than the same polymer translocates through a wild type alpha hemolysin polypeptide. The time required for a polymer to translocate through an alpha hemolysin polypeptide is referred to herein as a translocation time. A polymer that translocates through a first pore at a slower rate than a second pore often comprises a longer translocation time through the first pore when compared to the second pore. In some embodiments a polymer translocates through a modified alpha hemolysin polypeptide with a longer translocation time when compared to a translocation time of the same polymer through a reference pore (e.g., a wild type alpha hemolysin polypeptide).

In certain embodiments, a modified alpha hemolysin polypeptide comprising one or more amino acid substitutions outside of a beta barrel region enables slowing (e.g., increases the translocation time) of a polymer compared to a reference pore. In certain embodiments a modified alpha hemolysin polypeptide and a reference pore to which it is compared both comprise one or more amino acid substitutions within a beta barrel region. For example, a reference pore used for comparison sometimes does not have amino acid substitutions outside of a barrel region, but does comprise one or more beta barrel amino acid substitutions. For example, as described herein, the translocation time of the polymer polyC100 is increased in the modified alpha hemolysin polypeptide T109Y E111S M113S L135S T145S K147S V149Y compared to the alpha hemolysin polypeptide E111S M113S L135S T145S K147S that, as described herein, does not have a an amino acid substitution outside of a barrel region, but does comprise beta barrel amino acid substitutions.

The presence or absence of a change (e.g., a relative change; an increase) in the translocation time for the modified alpha hemolysin polypeptide, relative to the translocation time of the same polymer through a reference alpha hemolysin polypeptide, often is determined (e.g., measured) and/or quantified. A translocation time can be determined using a polyC100 or polyA100 polymer for the modified protein and the reference protein. A testing procedure that can be used for assessing translocation time includes determining the translocation time of a polyC100 or polyA100 polymer for the modified protein and the reference protein, where the reference protein is an alpha hemolysin polypeptide having the amino acid sequence of SEQ ID NO: 1. Detailed methods for determining (e.g., measuring) the translocation time of a polymer (e.g., a polynucleotide, a polypeptide) through an alpha hemolysin polypeptide are described herein. In certain embodiments, an increase in a translocation time of a polymer through a modified alpha hemolysin polypeptide is at least about 20 percent (e.g. at least about 30, 40, 50, 60, 70, 80, 90, 100, 150, 200, 250, 300, 350, 400, 450, 500, 1000 or 2000 percent) compared to the translocation time of the same polymer through an alpha hemolysin polypeptide without at least one native amino acid substituted with the non-native amino acid (e.g., a wild type alpha hemolysin polypeptide).

Improvements as a Result of Polymer Slowing

In certain embodiments, the modified alpha hemolysin polypeptide can be used for sequencing a polymer. In certain embodiments, the slowing of a polymer enabled by the modified alpha hemolysin polypeptide can improve the accuracy of sequencing the polymer. For example, if a polymer has an increased translocation time through a protein pore, then a lower measurement bandwidth can be used. The lower measurement bandwidth results in lower measurement noise, thus increasing the signal to noise ratio. In the case of sequencing, the signal to noise ratio can be termed contrast signal to noise ratio (CNR) to demonstrate the difference between two bases (e.g. the signal difference between adenine and cytosine) compared to the noise. This concept and protein pores with high CNR values are described in patent application nos. PCT/US2012/043859 and PCT/US2012/043864, both herein incorporated by reference.

In certain embodiments, the modified alpha hemolysin polypeptide permits a measurement of a first level and a second level within a residual current of the modified alpha hemolysin polypeptide, as the polymer translocates through the modified alpha hemolysin polypeptide, with a contrast signal to noise ratio (CNR) computed at a predetermined filter frequency. In certain embodiments, the polymer comprises two or more sections, each of which sections comprises at least a portion of a monomer. The CNR is calculated as a contrast signal divided by a noise value where the contrast signal is calculated as the difference between the first level and the second level and each level used for calculating the CNR correlates to a composition of a section of the polymer. Furthermore, the first level and the second level are measurably distinct. The noise value is computed at the predetermined filter frequency. In certain embodiments, the increase in translocation time of the polymer enables a lower predetermined filter frequency to be used in the computation of the CNR. In certain embodiments, the lower predetermined frequency is at least 5 percent lower (e.g. at least 5, 10, 20, 30, 40, 50, 60, 70, 80, 90, 95 percent lower). In some embodiments, the lower predetermined filter frequency results in a lower noise value. In certain embodiments, the lower noise value is at least 5 percent lower (e.g. at least 5, 10, 20, 30, 40, 50, 60, 70, 80, 90, 95 percent lower). In some embodiments, the lower noise value results in a higher CNR. In certain embodiments, the higher CNR is at least 5 percent higher (e.g. at least 5, 10, 20, 30, 40, 50, 60, 70, 80, 90, 100, 200, 500, 1000 percent higher). In some embodiments, a higher CNR enables sequencing of the polymer. In certain embodiments, a higher CNR enables more accurate sequencing of the polymer.

In some embodiments, the CNR of the modified alpha hemolysin protein pore is lower than the CNR for the protein pore without the at least one native amino acid substituted with the non-native amino acid at the same predetermined filter frequency. In certain embodiments, the lower predetermined filter frequency that can be used as a result of the increase in translocation time results in a lower noise value. In certain embodiments, the lower noise value results in a higher CNR at the lower predetermined filter frequency for the modified alpha hemolysin protein pore than the CNR for the protein pore without the at least one native amino acid substituted with the non-native amino acid at the higher predetermined filter frequency. In certain embodiments, the higher CNR enables sequencing of the polymer. In certain embodiments, the higher CNR enables more accurate sequencing of the polymer. In certain embodiments, the noise associated with the polymer in the modified alpha hemolysin protein pore and/or the protein pore without the at least one native amino acid substituted with the non-native amino acid is white noise (i.e. has a relatively flat power spectral density) in the bandwidth of interest (e.g. 100 to 20,000 Hz). In certain embodiments, the higher CNR at the lower predetermined filter frequency can be estimated when the noise associated with the polymer in the modified alpha hemolysin protein pore and/or the protein pore without the at least one native amino acid substituted with the non-native amino acid is white noise. In some embodiments, when the noise is white noise, the noise at the lower predetermined filter frequency (PDL) is equal to the noise at the higher predetermined filter frequency (PDH) multiplied by the square root of the PDL divided by the PDH. For example, the noise at the PDL of 1000 Hz is equal to the noise at the PDH of 4000 Hz multiplied by the square root of 1000/4000. In certain embodiments, when the noise is white noise, if the tmax is increased, then the predetermined filter frequency can be reduced by the same amount the tmax is increased. For example, if the tmax is increased by a factor of 2, then the predetermined filter frequency can be reduced by a factor of 2. In certain embodiments, a Weighted CNR, due to the described relationship between tmax and the bandwidth, can be estimated by multiplying the CNR at the predetermined filter frequency by the square root of the tmax. In some embodiments, a ratio of the Weighted CNR of the modified alpha hemolysin protein pore to the Weighted CNR of the protein pore without the at least one native amino acid substituted with the non-native amino acid factor is computed. In certain embodiments, the ratio of Weighted CNRs is computed by dividing the Weighted CNR of the modified alpha hemolysin protein pore by the Weighted CNR of the protein pore without the at least one native amino acid substituted with the non-native amino acid. In certain embodiments, if the ratio is greater than 1, then the modified alpha hemolysin protein pore has a higher Weighted CNR than the protein pore without the at least one native amino acid substituted with the non-native amino acid. In some embodiments, a higher Weighted CNR enables sequencing of the polymer. In certain embodiments, a higher Weighted CNR enables more accurate sequencing of the polymer.

Nanopore Devices

In some embodiments, provided is a device or apparatus, termed nanopore device, that includes a modified alpha hemolysin polypeptide described herein. Any suitable device capable of supporting a modified alpha hemolysin polypeptide and allowing for sensing of an analyte can be utilized. Nanopore devices are often comprised of a substrate that includes an aperture and one or more proteins or polypeptides inserted in the aperture. In certain embodiments, the protein is inserted in a lipid monolayer and/or bilayer that traverses the aperture. In some embodiments, the protein is retained within the aperture without a lipid monolayer and/or bilayer. In some embodiments, a substrate includes a well and one or more proteins inserted in the well opening within a lipid monolayer and/or bilayer that traverses the well opening. In certain embodiments, a substrate includes a well and one or more proteins inserted in the well opening without a lipid monolayer and/or bilayer that traverses the well opening.

In certain embodiments, an apparatus or device comprising a hemolysin polypeptide comprises a direct current (DC) measurement system. In some embodiments, an apparatus or device comprising a hemolysin polypeptide comprises an alternating current (AC) measurement system. In certain embodiments, an apparatus or device comprises an AC/DC measurement system. Conditions in which a polymer translocates through a protein pore (e.g., a hemolysin polypeptide, an apparatus or device comprising a hemolysin pore) often include an applied voltage bias. In some embodiments, for measuring DC potential in a nanopore system comprising a hemolysin pore protein (e.g., for DC measurement systems), a voltage bias is applied across a pore to produce a measurable current. A voltage bias is often held constant for a measurement of a CNR. A voltage bias used in a nanopore residual current measurements can have an effect on a measured CNR. In general, as a bias is increased, the contrast between polymer sections increases and the average duration per polymer section will decrease. Non-limiting examples of bias ranges that can be used to measure a CNR include 20 millivolts (mV) to 300 mV or greater (e.g., 20 mV, 30 mV, 40 mV, 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 210 mV, 220 mV, 230 mV, 240 mV, 250 mV, 260 mV, 270 mV, 280 mV, 290 mV, 300 mV or greater). In some embodiments, for an AC measurement system, a source signal that is periodic (e.g. sinusoidal or a square wave) is applied and is defined by an applied bias (e.g. an AC bias) and frequency. Conditions in which a polymer translocates through a protein pore (e.g., a hemolysin polypeptide) often include an applied AC bias. Non-limiting examples of an applied AC bias include 50 mV to 1000 mV (e.g. 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 300 mV, 400 mV, 500 mV, 600 mV, 700 mV, 800 mV, 900 mV, or 1000 mV). Non-limiting examples of the frequency include 10 kHz to 300 kHz or greater (e.g. 10 kHz, 20 kHz, 30 kHz, 40 kHz, 50 kHz, 60 kHz, 70 kHz, 80 kHz, 90 kHz, 100 kHz, 150 kHz, 200 kHz, 250 kHz, 300 kHz or greater).

In some embodiments, the substrate comprises glass, Si, $SiO_2$, $Si_3N_4$, alumina, nitrides, diamond, quartz, sapphire metals, ceramics, alumino-silicate, polymers (e.g., Teflon, polycarbonate), the like or combinations thereof. Non-limiting examples of glass types suitable for a substrate include fused silica glass, ninety-six percent silica glass, soda-lime silica glass, borosilicate glass, aluminosilicate glass, lead glass, doped glass comprising desired additives, functionalized glass comprising desired reactive groups, the like and combinations thereof. Non-limiting examples of minerals (e.g., quartz) suitable for a substrate include quartz, tridymite, cristobalite, coesite, lechatelierite, stishovite, the like and combinations thereof. The substrate can be manufactured from a pure substance or can be manufactured from a composite material.

The thickness of a substrate typically ranges from about 100 nanometer (nm) to 5 millimeters (mm) in thickness (e.g., about 100 nm, about 150 nm, about 200 nm, about 250 nm, about 300 nm, about 350 nm, about 400 nm, about 500 nm, about 600 nm, about 700 nm, about 800 nm, about 900 nm, about 1000 nm (e.g., about 1 µm), about 2 µm, about 3 µm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm, 100 µm, about 110 µm, about 120 µm, about 130 µm, about 140 µm, about 150 µm, about 175 µm, about 200 µm, about 225 µm, about 250 µm, about 300 µm, about 350 µm, about 400 µm, about 450 µm, about 500 µm, about 600 µm, about 700 µm, about 800 µm, about 900 µm, 1000 µm (e.g. 1 mm), about 2 mm, about 3 mm, about, about 4 mm, or about 5 mm).

In certain embodiments, a substrate contains an aperture that separates two fluid reservoirs. In some embodiments, the aperture is a micron scale aperture, and sometimes the aperture is a nanoscale aperture. In some embodiments, the aperture is in a glass or quartz substrate. In certain embodiments, the aperture has a diameter of about 0.25 nanometer to about 100 µm (e.g., about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 2 µm, about 3 µm, about 4 µm, about 5 µm, about 10 µm, about 15 µm, about 20 µm, about 25 µm, about 30 µm, about 35 µm, about 40 µm, about 45 µm, or about 50 µm).

In certain embodiments, a substrate comprises a well. In some embodiments, the well has an aperture formed by the well opening with a diameter of about 100 nanometers to about 100 µm (e.g., about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 2 µm, about 3 µm, about 4 µm, about 5 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm or about 100 µm).

The channel formed by the aperture in a substrate is of any suitable geometry, and sometimes has a substantially circular, oval, square, rectangular, rhomboid, parallelogram, or other like cross-section. The channel in the substrate is of any suitable profile, and sometimes has a substantially cylindrical or conical (e.g., tapering or expanding conical) profile.

A substrate sometimes comprises a coating that modifies the surface of an aperture or well structure. In some embodiments, a substrate comprises a surface that includes a hydrophobic substance. In certain embodiments, a substrate comprises a surface that includes a hydrophilic substance. In some embodiments, a substrate comprises a surface that includes hydrophobic and hydrophilic substances.

Thus, one or more portions of, or the entire, substrate can be treated or coated to adopt certain desirable characteristics, in some embodiments. In certain embodiments, the treatment or coating enhances formation of lipid structures across the aperture of the substrate. Physical and/or chemical modification of the surface properties of a substrate include, but are not limited to, modification of the electrical charge density, changes to the hydrophobicity, changes to the hydrophilicity, the like and combinations thereof. Any suitable substance can be utilized to modify one or more interior and/or exterior surfaces of the substrate. Non-limiting examples of suitable materials for modification of one or more substrate surfaces include silanes, silanes terminating in a cyano group, silanes terminating in a methyl group, thiols, the like, or combinations thereof. In some embodiments, an exterior surface of a substrate may be modified by a first entity. In certain embodiments, an interior surface of a substrate may be modified by a second entity. In some embodiments, the first and the second entity may be the same entities, and in certain embodiments, the first and the second entity may be different entities. In some embodiments utilizing a glass substrate, the first or second entities that can be used to modify the interior or exterior surfaces of a substrate include a variety of glass-reactive species, e.g., 3-cyano-propyldimethylchlorosilane, that react with the silanol groups of the glass surface.

In some embodiments, a device comprises a lipid composition (e.g., monolayer, bilayer, combination thereof) over, across or spanning an aperture of a substrate. A lipid composition sometimes comprises a lipid monolayer, sometimes comprises a lipid bilayer, and in some embodiments comprises a lipid layer that partially is a monolayer and partially is a bilayer. In some devices comprising both monolayer and bilayer lipid structures, solvent may be trapped at a location (e.g., an annulus) between the substrate and the lipid layer at or near the monolayer and bilayer interface, which is addressed in greater detail hereafter.

The lipid composition of a device often is relatively stable to mechanical disturbances, and can have a lifetime in excess of two weeks. Additionally, a device can be made with a lipid composition that is readily formed over or in an aperture and has a relatively small surface area, which can give rise to favorable electrical characteristics.

Nanopore membrane devices can comprise a channel or nanopore embedded in a suitable material. The diameter of an aperture of a channel in a membrane, across which an amphiphilic composition forms in a nanopore membrane system, often ranges in diameter from about 0.25 nanometers to about 50 µm (e.g., about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 1.5 µm, about 2 µm, about 2.5 µm, about 3 µm, about 3.5 µm, about 4 µm, about 5 µm, about 10 µm, about 15 µm, about 20 µm, about 25 µm, about 30 µm, about 35 µm, about 40 µm, about 45 µm, or about 50 µm). The channel formed in the membrane is of any suitable geometry, and sometimes has a substantially circular, oval, square, rectangular, rhomboid, parallelogram, or other like cross-section. The channel formed in the membrane is of any suitable profile, and sometimes has a substantially cylindrical or conical (e.g., tapering or expanding conical) profile.

Nanopore membrane devices often are composed of a single conical-shaped channel or nanopore embedded in a suitable material. Membranes can be formed as known in the art and as described herein.

While a device often comprises a lipid composition traversing a substrate aperture, the composition traversing the substrate aperture may comprise any suitable amphiphilic molecule(s) or material(s) that can stably traverse an aperture and into which a protein can be incorporated. An amphiphilic molecule generally is composed of a hydrophobic portion and a polar portion. The terms "amphiphilic material" or "amphiphilic materials" refer to materials made of molecules having a polar, water-soluble group attached to a nonpolar, water-insoluble hydrocarbon chain. Amphiphilic materials sometimes can be polymers. Amphiphilic materials may be a pure substance or a mixture of different amphiphilic materials. The polymeric materials may be a polymer with a uniform molecular weight distribution, or a polymer with a non-uniform molecular weight distribution, or a mixture of polymers which comprise different monomers. Non-limiting examples of amphiphilic materials include lipids, detergents, surfactants, proteins, polysaccharides, and other chemical or biochemical materials that can be rendered amphiphilic.

The terms "detergent" or "detergents" as used herein refer to a surfactant or a mixture of surfactants. In some embodiments, "surfactant" or "surfactants" refer to any compound that (i) lowers the surface tension of a liquid, allowing easier spreading, and/or (ii) lowers the interfacial tension between two liquids, or between a liquid and a solid. Surfactants may act as: detergents, wetting agents, emulsifiers, foaming agents, and dispersants. Surfactants often are categorized as ionic (anionic or cationic), zwitterionic or amphoteric, or non-ionic. Non-limiting examples of surfactants include ammonium lauryl sulfate, sodium lauryl sulfate (SDS), sodium laureth sulfate (e.g., also known as sodium lauryl ether sulfate (SLES)), sodium myreth sulfate, dioctyl sodium sulfosuccinate, perfluorooctanesulfonate (PFOS), perfluorobutanesulfonate, alkyl benzene sulfonates, alkyl aryl ether phosphate, alkyl ether phosphate, fatty acid salts (e.g., soaps), sodium stearate, sodium lauroyl sarcosinate, perfluorononanoate, perfluorooctanoate, octenidine dihydrochloride, cetyl trimethylammonium bromide (CTAB), cetyl trimethylammonium chloride (CTAC), Cetylpyridinium chloride (CPC), polyethoxylated tallow amine (POEA), benzalkonium chloride (BAC), benzethonium chloride (BZT); 5-Bromo-5-nitro-1,3-dioxane, dimethyldioctadecylammonium chloride, dioctadecyldimethylammonium bromide, 3-[(3-Cholamidopropyl)dimethylammonio]-1-propanesulfonate (e.g., CHAPS), cocamidopropyl hydroxysultaine, amino acids, imino acids, cocamidopropyl betaine, lecithin, fatty alcohols (e.g., cetyl alcohol, stearyl alcohol, and the like), the like and combinations thereof.

A lipid molecule typically comprises at least one hydrophobic chain and at least one polar head. When exposed to an aqueous environment, lipids often will self-assemble into structures that minimize the surface area exposed to a polar (e.g., aqueous) medium. Lipids sometimes assemble into structures having a single or monolayer of lipid enclosing a non-aqueous environment, and lipids sometimes assemble into structures comprising a bilayer enclosing an aqueous environment. In a monolayer structure, the polar portion of lipids (e.g., the head of the molecule in the case of phospholipids and other lipids commonly found in cell substrates) often is oriented towards the polar, aqueous environment, allowing the non-polar portion of the lipid to contact the non-polar environment.

A lipid bilayer typically comprises a sheet of lipids, generally two molecules thick, arranged so the hydrophilic phosphate heads point towards a hydrophilic aqueous environment on either side of the bilayer and the hydrophobic tails point towards the hydrophobic core of the bilayer. This arrangement results in two "leaflets" that are each a single molecular layer. Lipids self-assemble into a bilayer structure due to the hydrophobic effect and are held together entirely by non-covalent forces that do not involve formation of chemical bonds between individual molecules. Lipid bilayers generally also are impermeable to ions, which allow cells to regulate various processes that involve salt concentrations or gradients and intracellular pH by pumping ions across cell substrates using ion transport mechanisms.

In some embodiments, lipid bilayers are natural, and in certain embodiments lipid bilayers are artificially generated. Natural bilayers often are made mostly of phospholipids, which have a hydrophilic head and two hydrophobic tails (e.g., lipid tails), and form a two-layered sheet as noted above, when exposed to water or an aqueous environment. The center of this bilayer contains almost no water and also excludes molecules like sugars or salts that dissolve in water, but not in oil. Lipid tails also can affect lipid composition properties, by determining the phase of the bilayers, for example. A bilayer sometimes adopts a solid gel phase state at lower temperatures and undergoes a phase transition to a fluid state at higher temperatures. The packing of lipids within a bilayer also affects its mechanical properties, including its resistance to stretching and bending.

Artificial bilayers (e.g., sometimes also referred to as "model lipid bilayers") are any bilayers assembled through artificial means, as opposed to bilayers that occur naturally (e.g., cell walls, lipid bilayers that cover various sub-cellular structures). An artificial bilayer can be made with synthetic and/or natural lipids, thus the process, not the material, defines an artificial or model system. Properties, such as stretching, bending or temperature induced phase transitions, have been studied with artificial model bilayers. The simplest model systems contain only a single pure synthetic lipid. The artificial bilayer also may contain a hydrophobic solvent, such as decane, hexadecane, pentane or other solvents and combinations thereof, that is used to disperse the lipid during bilayer formation and stabilize the formation of lipid bilayers across apertures in hydrophobic materials. The simplicity of a single lipid system is advantageous when determining physical or mechanical properties of bilayers. Model bilayers with greater physiological relevance can be generated utilizing mixtures of several synthetic lipids or, as mentioned, with natural lipids extracted from biological samples.

The presence of certain lipids or proteins sometimes can alter the surface chemistry of bilayers (e.g., viscosity or fluidity of lipid bilayers). Phospholipids with certain head groups can alter the surface chemistry of a bilayer. Non-limiting examples of bilayer constituents that can alter the surface chemistry of bilayers include fats, lecithin, cholesterol, proteins, phospholipids (e.g., phosphatidic acid (phosphatidate), phosphatidylethanolamine (e.g., cephalin), phosphatidylcholine (e.g., lecithin), phosphatidylserine, and phosphoinositides such as phosphatidylinositol (PI), phosphatidylinositol phosphate (PIP), phosphatidylinositol bisphosphate (PIP2) and phosphatidylinositol triphosphate (PIP3), phosphatidylglycerol, ceramide phosphorylcholine, ceramide phosphorylethanolamine, ceramide phosphorylglycerol), surfactants, the like and combinations thereof.

A device may include one or more types of molecules other than phospholipids. For example, cholesterol, which helps strengthen bilayers and decreases bilayer permeability can be included. Cholesterol also helps regulate the activity of certain integral substrate proteins. Different types or forms of lipid compositions (e.g., monolayers and/or bilayers) can be found naturally or generated artificially. Non-limiting examples of lipid compositions include monolayers (e.g., micelles) and bilayers including "black PLBs", vesicles (e.g., sometimes referred to as "liposomes"), supported lipid bilayers, linear lipid bilayers and the like.

A nanopore membrane device often comprises a lipid composition (e.g., monolayer, bilayer, combination thereof) over, across or spanning an aperture of a substrate. A lipid composition can comprise one or more types of lipids having various chain lengths and/or various structures of polar heads. A lipid composition of a nanopore membrane device often is relatively stable to mechanical disturbances, and can have a lifetime in excess of two weeks. A lipid composition sometimes comprises a lipid monolayer, sometimes comprises a lipid bilayer, and in some embodiments comprises a lipid layer that partially is a monolayer and partially is a bilayer. A portion of a lipid composition in a device can interact with one or more exterior and/or interior surfaces of a substrate. In some devices comprising both monolayer and bilayer lipid structures, solvent may be trapped at a location (i.e., annulus) between the substrate and the lipid layer at or near the monolayer and bilayer interface, which is addressed in greater detail hereafter. In certain embodiments, a lipid composition that spans across the substrate aperture is a combination of a lipid bilayer and monolayer. In various embodiments, a lipid monolayer deposited on the exterior surface of a substrate and a lipid monolayer deposited on the interior surface of the channel or nanopore that join together at about the edge of the channel or nanopore opening can form a lipid bilayer spanning or suspended across the aperture. The bilayer formed across an aperture sometimes is referred to as a "spanning lipid bilayer" herein.

In a spanning bilayer structure, a bilayer often is present across the substrate aperture and a monolayer is present on substrate surfaces (e.g., chemically modified surfaces and/or hydrophobic). In some embodiments, a chemically modified device corrals a single protein pore in the lipid bilayer region that spans across the aperture. An inserted protein (e.g., protein pore, alpha hemolysin, modified alpha hemolysin polypeptide) often is able to diffuse in the bilayer across the aperture but often cannot leave this area to enter the lipid monolayer. Insertion of a sensing entity (e.g., protein pore) often occurs only in the bilayer region. A thin layer (e.g., about 1 to about 10 nm thick) containing solvent and ions sometimes is formed between a spanning lipid bilayer and one or more surfaces of the substrate. The thickness of this layer is defined as the distance between the exterior surface and the lipid bilayer and often plays a role in determining the resistance of the bilayer seal and the stability and fluidity of the bilayer. A spanning bilayer also sometimes includes an annulus formed between monolayers and a channel or nanopore surface, which can contain solvent (e.g., FIG. 15 of U.S. Pat. No. 7,777,505).

A protein often is inserted into a structure (e.g., monolayer and/or bilayer) formed by the lipid or amphiphilic material composition. A protein that is inserted into the structure can be water soluble, detergent-solubilized or incorporated into a lipid bilayer (e.g., vesicle, liposome) or a lipid monolayer (e.g., micelle) prior to insertion into a PLB, in some embodiments. Membrane proteins sometimes cannot be incorporated directly into the PLB during formation because immersion in an organic solvent sometimes can denature the protein. Exceptions include alpha hemolysin, MspA, and gramicidin. A membrane protein sometimes is solubilized with a detergent and added to the aqueous solution after the bilayer is formed. The dilution of the detergent stabilizing the protein forces the proteins to spontaneously insert into the bilayer over a period of minutes or hours, and often at a low frequency of success.

A vesicle is a lipid bilayer configured as a spherical shell enclosing a small amount of water or aqueous solution and separating it from the water or aqueous solution outside the vesicle. Because of the fundamental similarity to a cell wall, vesicles have been used to study the properties of lipid bilayers. Vesicles also are readily manufactured. A sample of dehydrated lipid spontaneously forms vesicles, when exposed to water. Spontaneously formed vesicles can be unilamelar (single-walled) or multilamellar (e.g., many-walled) and are of a wide range of sizes from tens of nanometers to several micrometers. A liposome is an artificially prepared vesicle, and also comprises a lipid bilayer and also can be made of naturally occurring or synthetic lipids, including phospholipids. There are four types of liposomes: MLV (multilamellar vesicles), SUV (Small Unilamellar Vesicles), LUV (Large Unilamellar Vesicles) and GUV (Giant Unilamellar Vesicles). Liposomes may be used to form PLBs on a surface or across apertures.

Unlike a vesicle or a cell substrate in which the lipid bilayer forms an enclosed shell, a supported bilayer (e.g., SLB) is a planar structure in contact with a substrate. One advantage of the supported bilayer is its stability. SLBs often remain largely intact even when subject to high flow rates or vibration, and the presence of holes will not destroy the entire bilayer. Due to the stability of SLB's, experiments lasting weeks and even months can be conducted with supported bilayers, while BLM experiments sometimes are limited to hours. Another advantage of the supported bilayer is the greater number of methods and tools usable for characterization. In certain embodiments, a substrate may comprise a hydrophilic material, such as untreated glass, or it may be modified in a manner that renders one or more surfaces of the substrate (e.g., pore interior, pore exterior) hydrophilic (e.g. mildly hydrophilic, substantially hydrophilic). In certain embodiments, the bilayer is then formed over the hydrophilic surface and covers across the substrate aperture.

In certain embodiments, a substrate may include a hydrophobic material, such as Teflon, or it may be modified in a manner that renders one or more surfaces of the substrate (e.g., substrate channel interior, substrate channel exterior) hydrophobic (e.g. mildly hydrophobic, substantially hydrophobic). In some embodiments one or more surfaces of a substrate are coated with a hydrophobic substance, including without limitation an alkyl silane substance (e.g., 3-cyanopropyldimethylchlorosilane). Any suitable silane substance can be selected to render a substrate surface more hydrophobic and support interaction with lipids for formation of a lipid structure that spans the substrate aperture. In some embodiments, a spanning lipid structure contains a monolayer that interacts with an exterior surface of a substrate and a monolayer that interacts with an interior surface of the substrate, where the monolayers join together at about the edge of the opening of the aperture and form a lipid bilayer spanning the substrate aperture (e.g., U.S. Pat. No. 7,777, 505, entitled "Nanopore platforms for ion channel recordings and single molecule detection and analysis," naming White et al. as inventors).

In certain embodiments, a nanopore apparatus comprises a Nanopore Membrane System as described in U.S. patent application Ser. No. 13/414,636 filed on Mar. 7, 2012, entitled "METHODS FOR VOLTAGE-INDUCED PROTEIN INCORPORATION INTO PLANAR LIPID BILAYERS," naming Ryan Dunnam, Geoffrey Barrall and Melissa Poquette as inventors, the entirety of which herein is incorporated by reference, including all text, tables and drawings.

Conditions in which a polymer translocates through a protein pore (e.g., a hemolysin polypeptide, a modified alpha hemolysin polypeptide, a device comprising a hemolysin polypeptide) often include a suitable electrolyte solution Any suitable electrolyte solution generally known can be used to translocate a polymer or to measure a CNR. Non-limiting examples of electrolyte solutions include solutions comprising a suitable salt such as sodium chloride, potassium chloride, lithium chloride, the like, or combinations thereof with concentrations ranging from 0.1 to 6 Molar (M) (e.g. 0.1 M, 0.2 M, 0.3 M, 0.4 M, 0.5 M, 1 M, 2 M, 3 M, 4 M, 5 M, or 6 M). In certain embodiments, a buffer is included in an electrolyte solution to stabilize the pH. Any suitable buffer can be used. In certain embodiments, a buffer comprises Tris at a concentration of at least 300 mM, at least 200 mM, at least 100 mM, at least 50 mM, at least 10 mM Tris or at least 1 mM. In some embodiments an electrolyte solution comprises a suitable chelator such as EDTA at a concentration of at least 0.1 mM, at least 0.5 mM or at least 1 mM. In certain embodiments, a pH of an electrolyte solution ranges from 5 to 9 (e.g. 5, 5.5, 6, 6.5, 7, 7.5, 8.0, 8.5, or 9.0). In certain embodiments, a pH of an electrolyte solution can range from about 7 to 7.5 (e.g. 7.0, 7.1, 7.2, 7.3, 7.4, 7.5).

EXAMPLES

The examples set forth below illustrate certain embodiments and do not limit the technology.

Example 1

Unmodified Alpha Hemolysin Amino Acid Sequence

The amino acid sequence for a wild type (WT) alpha hemolysin polypeptide, which contains 293 amino acids as presented, is provided herein as SEQ ID NO: 1 for reference:

```
                                            SEQ ID NO: 1
MADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQIS
DYYPRNSIDTKEYMSTLTYGFNGNVTGDDTGKIGGLIGANVSIGHTLKYV
QPDFKTILESPTDKKVGWKVIFNNMVNQNWGPYDRDSWNPVYGNQLFMKT
RNGSMKAADNFLDPNKASSLLSSGFSPDFATVITMDRKASKQQTNIDVIY
ERVRDDYQLHWTSTNWKGTNTKDKWTDRSSERYKIDWEKEEMTN (YY-4S L135I D127K)
                                            SEQ ID NO: 2
MADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQIS
DYYPRNSIDYKSYSSTLTYGFNGNVTGKDTGKIGGIIGANVSIGHSLSYY
QPDFKTILESPTDKKVGWKVIFNNMVNQNWGPYDRDSWNPVYGNQLFMKT
RNGSMKAADNFLDPNKASSLLSSGFSPDFATVITMDRKASKQQTNIDVIY
ERVRDDYQLHWTSTNWKGTNTKDKWTDRSSERYKIDWEKEEMTN (YY-4S L135I)
                                            SEQ ID NO: 3
MADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQIS
DYYPRNSIDYKSYSSTLTYGFNGNVTGDDTGKIGGIIGANVSIGHSLSYY
QPDFKTILESPTDKKVGWKVIFNNMVNQNWGPYDRDSWNPVYGNQLFMKT
RNGSMKAADNFLDPNKASSLLSSGFSPDFATVITMDRKASKQQTNIDVIY
ERVRDDYQLHWTSTNWKGTNTKDKWTDRSSERYKIDWEKEEMTN
```

Example 2

Below is a table of example polypeptides comprising a modified alpha hemolysin amino acid sequence (Table 1). This list should in no way be considered limiting to the modifications that can be made to a reference alpha hemolysin reference amino acid sequence for the production of a modified alpha hemolysin amino acid sequence. The position numbers are in reference to SEQ ID NO: 1 provided in Example 1. The format is such that the term T109Y indicates that the native amino acid T109 (threonine at position 109) has been substituted with the non-native amino acid Y (tyrosine). In addition, L135I indicates that the beta barrel amino acid L135 (leucine at position 135) has been replaced with the different amino acid I (isoleucine). The abbreviated names for some of the modified alpha hemolysin polypeptides are provided for reference to the data presented in this application.

TABLE 1

| Modified Alpha Hemolysin Protein pore | ABBREVIATED NAME |
| --- | --- |
| T109Y/E111S/M113S/N121D/N123M/L135S/G137K/N139S/T145S/K147S/V149Y | YY-4S SDKMS |
| I107Y/T109Y/E111S/M113S/N121D/N123M/L135S/G137K/N139S/T145S/K147S/V149Y | 3Y-4S SDKMS |
| I107Y/T109Y/E111S/M113S/N121D/N123M/L135S/G137K/N139S/T145S/K147S/V149Y/P151Y | 4Y-4S SDKMS |
| E111S/M113S/N121D/N123M/L135S/G147K/N139S/T145S/K147S/V149W | V149W 4S SDKMS |
| T109Y/E111S/M113S/N121D/N123M/L135S/G137K/N139S/T145S/K147S/V149W | YW-4S SDKMS |
| T109W/E111S/M113S/N121D/N123M/L135S/G137K/N139S/T145S/K147S/V149Y | WY-4S SDKMS |
| T109W/E111S/M113S/N121D/N123M/L135S/G137K/N139S/T145S/K147S/V149W | WW-4S SDKMS |
| I107W/T109W/E111S/M113S/N121D/N123M/L135S/G137K/N139S/T145S/K147S | I107W T109W-4S SDKMS |
| T109W/E111S/M113S/N121D/N123M/L135S/G137K/N139S/T145S/K147S | T109W-4S SDKMS |
| T109F/E111S/M113S/N121D/N123M/L135S/G137K/N139S/T145S/K147S/V149F | FF-4S SDKMS |
| T109Y/E111S/M113S/L135I/T145S/K147S/V149Y | YY-4S L135I |
| T109Y/E111S/M113S/D127K/L135I/T145S/K147S/V149Y | YY-4S L135I D127K |
| I107Y/T109Y/E111S/M113S/D127K/L135I/T145S/K147S/V149Y | 3Y-4S L135I D127K |

TABLE 1-continued

| Modified Alpha Hemolysin Protein pore | ABBREVIATED NAME |
|---|---|
| T109Y/E111S/M113S/D127K/L135I/T145S/K147S | Y109-4S L135I D127K |
| E111S/M113S/D127K/L135I/T14S/K147S/V149Y | Y149-4S L135I D127K |
| T109Y/E111S/M113S/T125Q/D127K/L135I/T145S/K147S/V149Y | YY-4S L135I T125Q D127K |
| T109Y/E111S/M113S/T125F/D127K/L135I/T145S/K147S/V149Y | YY-4S T135I T125F D127K |
| T109Y/E111S/M113S/T125S/D127K/L135I/T145S/K147S/V149Y | YY-4S L135I T125S D127K |
| T109Y/E111S/M113S/N121T/N123T/T125N/D127K/L135I/N139T/T145S/K147S/V149Y | YY-4S N3T L135I T125N D127K |
| T109Y/E111D/M113S/N121S/D127K/L135I/N139S/V149Y | YY-E111D M113S N2S L135I D127K |
| T109Y/E111D/M113I/N121S/N123S/L135G/N139S/V149Y | |
| T109Y/E111D/M113I/N121S/N123S/T125S/D127K/L135G/N139S/V149Y | |
| T109Y/E111D/M113I/N121S/N123S/D127K/L135G/N139S/T145F/V149Y | |
| T109Y/E111D/M113I/N121S/N123S/D127K/L135G/N139S/T145Q/V149Y | |
| T109Y/E111D/M113I/N121S/N123S/D127K/L135G/N139S/T145S/V149Y | |
| T109Y/E111S/M113S/N121D/N123M/T125S/L135S/G137K/N139S/T145S/K147S/V149Y | |
| T109Y/E111S/M113S/N121D/N123M/T125S/L135F/G137K/N139S/T145S/K147S/V149Y | |
| T109Y/E111S/M113S/N121D/N123M/T125S/L135O/G137K/N139S/T145S/K147S/V149Y | |
| T109Y/E111S/M113S/N121S/N139S/T145S/K147S/V149Y | YY-4S N25 |
| T109Y/V149Y | YY-WT |

Example 3

Provided in this Example 3 are descriptions of materials and procedures utilized to generate results reported in Example 4 and Example 5. Example 4 and Example 5 describe results of experiments performed to demonstrate the translocation of a polymer through a modified alpha hemolysin polypeptide and in some cases demonstrate slowing of the polymer through the modified alpha hemolysin polypeptide compared to the alpha hemolysin polypeptide without the at least one native amino acid substituted with the non-native amino acid. The slowing of the polymer through the modified alpha hemolysin polypeptide could be beneficial to reducing the measurement bandwidth used to record the polymer translocating through the protein pore, thus improving the contrast signal to noise ratio (CNR) of a protein pore, and enabling sequencing of polymers through the modified alpha hemolysin polypeptide.

Apparatus

Glass or quartz nanopore membranes (GNMs) were fabricated, the interior of the GNM was filled with an electrolyte solution (e.g., 3 M NaCl (Sigma), 10 mM Tris, 2 mM EDTA and pH 7.2) and inserted horizontally through the wall of a polycarbonate cell into a fluid reservoir. An Ag/AgCl electrode produced by treating a 0.25 mm Ag wire with household bleach was placed interior to the GNM. A holder provided a secure mounting for the GNM, Ag/AgCl electrode interior to the GNM and provided a means of maintaining a constant back pressure on the GNM. The test cell had a reservoir of 250 µL and ports connected to syringes to allow for raising and lowering the fluid level in the reservoir. A second Ag/AgCl electrode was placed in the test cell reservoir. The GNM electrode and reference electrode were connected to a custom resistive feedback headstage that allows for applying a voltage bias between the electrodes and provides a low noise readout of the current between the two electrodes. All voltages were referenced with respect to the electrode in the GNM. For example, a negative bias indicates that the test cell reservoir electrode is at a negative potential with respect to the electrode interior to the GNM. Data was acquired with a PCI-6251 (National Instruments) DAQ card in a personal computer (Dell). A custom LabView application handled voltage control, data acquisition, and simple signal processing such as filtering.

Bilayer Formation 1,2-diphytanoyl-sn-glycero-3-phosphocholine (DPhPC) (Avanti) was diluted in decane (Sigma) to a concentration of 5 mg/ml. A test cell reservoir was filled to a level just above the face of the GNM with the electrolyte solution described herein. A small drop (e.g., less than about 0.5 µL) of the lipid/decane mixture was added to the surface of electrolyte. The fluid level in the test cell reservoir was then lowered below the face of the GNM and then raised above the face of the GNM. This action typically resulted in a bilayer although in some cases additional lipid was added and the raising and lowering repeated.

Protein Pore Preparation

Modified alpha hemolysin protein monomers were generated through coupled in vitro transcription and translation (IVTT) using a bacterial extract kit (Promega) and then assembled into homo-heptamers on rabbit red blood cell membranes (rRBCM) based on established protocols (B. Walker, and H. Bayley, "Key Residues for Membrane Binding, Oligomerization, and Pore Forming Activity of Staphylococcal alpha hemolysin Identified by Cysteine Scanning Mutagenesis and Targeted Chemical Modification," *J. Biol. Chem.*, vol. 270, no. 39, pp. 23065-23071, Sep. 29, 1995, 1995). Plasmid DNA (>95% supercoiled) of wild type and mutant alpha hemolysin were made by GenScript. For most IVTT reactions, 4 micrograms of the DNA (Genscript) were mixed with contents of the kit according to the manufacturer's recommendation and supplemented with a mixture of a complete set of amino acids and 4 microCi of $S^{35}$-Methionine (American Radiolabeled Chemicals). The mixture was incubated at 37° C. for one hour, then mixed with rRBCM and further incubated for three hours. At the end of the incubation period, membranes were washed twice with MOPS buffer followed by solubilization with SDS loading buffer. The latter was loaded onto a 5% polyacrylamide gel and proteins separated by applying a 60 V voltage overnight at room temperature. Gels were dried under vacuum at 60° C. for 3-4 hours and exposed to X-ray film (Kodak) overnight at −80° C. Gels were developed manually using Kodak Development and Wash solutions. Bands corresponding to alpha hemolysin were observed on the developed film due to the incorporation of the radioactive methionine. The film was used as a template to cut out portion of the dried gel containing the αHL protein. Proteins were recovered from this portion by overnight electro-elution using an Elutrap Electroelution system (GE Healthcare) and concentrated down to a volume of 10-20 microliters using microfuge concentrators (Millipore). Proteins were stored at −80° C. until use.

Alpha hemolysin incorporation in the bilayer was achieved by applying a back pressure (10-200 mmHg) to the interior of the GNM relative to the test cell reservoir. The precise pressure applied was determined by measuring the pressure at which the bilayer fails and using a pressure about 10 mmHg lower. After a single alpha hemolysin polypeptide was incorporated as determined by a large jump in conducted current, the pressure was reduced to maintain a single protein insertion. This holding pressure was determined by measuring the pressure at which alpha hemolysin was forced out of the bilayer. In some cases, the protein concentration was too low to allow for incorporation by applying a back pressure alone. In this case a high bias (>200 mV) was applied across the bilayer to promote protein insertion, as described in a recently filed U.S. patent application by EBS, U.S. Ser. No. 13/414,636.

Polymers

For the experiments presented, single stranded DNA was obtained from GeneLink at 100 micromolar concentration in 10 mM Tris, 1 mM EDTA pH 8.5. The strands obtained included polyC100 and polyA100. After obtaining a protein insertion, the DNA was added to the fluid reservoir of the test cell to allow the DNA to translocate the alpha hemolysin polypeptides. Typically 1 to 20 microliters of DNA was added to the test cell reservoir for a final DNA concentration between 0.4 to 8.0 micromolar.

Example 4

The examples shown below demonstrate the increase in translocation time that results from a modified alpha hemolysin polypeptide compared to the protein pore without the at least one native amino acid substituted with the non-native amino acid (e.g., a wild type alpha hemolysin protein).

Results

Below is a table showing the translocation times for the modified alpha hemolysin polypeptide and the corresponding alpha hemolysin polypeptide without the at least one native amino acid substituted with the non-native amino acid along with the polymer type (polyA100 or polyC100) and the percent increase in the translocation time between the two protein pores.

(TABLE 2 discloses "polyC100" and "polyA100" as SEQ ID NOS 4-5, respectively) All data was obtained using a direct current (DC) measurement system. The data was collected with a 100 kHz bandwidth at −120 mV.

Example 5

The results below demonstrate that the modified alpha hemolysin polypeptide can affect the computed CNR. These computations assume white noise, which is an accepted assumption for these measurements.

The CNR was computed in a manner consistent with the methods described in patent applications PCT/US2012/04859 and PCT/US2012/04864. The CNR was computed between homopolymers polyA100 and polyC100. The DNA was added to the test cell and allowed to translocate through the protein pore under a −120 mV DC bias and the data was recorded with a 100 kHz low pass filter. The data was processed and filtered to the original predetermined filter frequency of 10 kHz. The contrast was computed as the difference between the average polyA100 level and the average polyC100 level. The noise was then computed as the average RMS noise for polyA100 at 10 kHz and the average RMS noise for polyC100 at 10 kHz. A total noise value was computed by taking the square root of the sum of the squares of the RMS noise values for polyA100 and polyC100. In addition, a tmax (average duration) value was obtained for polyA100 and separately polyC100 events. The CNR was then computed by dividing the contrast by the total noise values. The CNR values for the modified alpha hemolysin polypeptide compared to the protein pore without the at least one native amino acid substituted with the non-native amino acid are shown in Table 3.

TABLE 2

| Modified Alpha Hemolysin Protein Pore | Translocation Time (micro seconds) | Alpha Hemolysin Protein Pore without the at least One Native Amino Acid Substituted with the Non-Native Amino Acid | Translocation Time (micro seconds) | % Increase in Translocation Time | Polymer |
|---|---|---|---|---|---|
| YY-4S SDKMS | 362 | 4S SDKMS | 102 | 354.9% | polyC100 |
| 4Y-4S SDKMS | 398 | 4S SDKMS | 102 | 390.2% | polyC100 |
| V149W 4S SDKMS | 271 | 4S SDKMS | 102 | 265.7% | polyC100 |
| YW-4S SDKMS | 1135 | 4S SDKMS | 102 | 1112.7% | polyC100 |
| WY-4S SDKMS | 919 | 4S SDKMS | 102 | 901.0% | polyC100 |
| I107W T109W-4S SDKMS | 249 | 4S SDKMS | 102 | 244.1% | polyC100 |
| YY-4S L135I D127K | 420 | 4S L135I D127K | 100 | 420.0% | polyC100 |
| YYY-4S L135I D127K | 2100 | 4S L135I D127K | 291 | 721.6% | polyA100 |
| YY-4S L135I T125Q D127K | 589 | 4S L135I T125Q D127K | 278 | 211.9% | polyA100 |
| YY-4S L135I T125S D127K | 1170 | 4S L135I T125S D127K | 156 | 750.0% | polyA100 |
| YY-4S L135I T125S D127K | 275 | 4S L135I T125S D127K | 58 | 474.1% | polyC100 |
| YY-4S N3T L135I T125N D127K | 686 | 4S N3T L135I T125N D127K | 163 | 420.9% | polyA100 |
| YY-E111D M113S N2S L135I D127K | 400 | 4S N3T L135I T125N D127K | 169 | 236.7% | polyA100 |
| YY-E111D M113S N2S L135I D127K | 314 | E111D M113S N2S L135I D127K | 79 | 397.5% | polyC100 |
| YY-WT | 3941 | WT | 847 | 465.3% | polyA100 |
| YY-WT | 1520 | WT | 214 | 710.3% | polyC100 |

TABLE 3

| Modified Alpha Hemolysin Protein Pore | Contrast | Total Noise (10 kHz) | CNR | Tmax polyA100 (micro seconds) | Alpha Hemolysin Protein Pore without the at least One Native Amino Acid Substituted with the Non-Native Amino Acid | Contrast | Total Noise (10 kHz) | CNR | Tmax polyA100 (micro seconds) |
|---|---|---|---|---|---|---|---|---|---|
| YY-4S L135I D127K | 13.3 | 4.75 | 2.8 | 1458 | 4S L135I D127K | 10.4 | 2.08 | 5.0 | 279 |
| YY-4S L135I T125S D127K | 7.5 | 5.88 | 1.3 | 1156.0 | 4S L135I T125S D127K | 8.6 | 3.01 | 2.9 | 154 |

The data show that in some cases, the CNR at the same measurements bandwidth between the modified alpha hemolysin polypeptide and the protein pore without the at least one native amino acid substituted with the non-native amino acid decreases. However, the increase in translocation time enables a lower measurement bandwidth (predetermined filter frequency) to be utilized, which will result in lower total noise. Thus, a calculation assuming white noise is done to determine the overall effect on the CNR as a result of this reduced total noise. The calculation is as follows:

Weighted CNR=CNR*sqrt($t$max)

Table 4 below shows the Weighted CNRs taking into account the translocation time, tmax. In addition, a ratio between the Weighted CNR of the modified alpha hemolysin polypeptide to the protein pore without the at least one native amino acid substituted with the non-native amino acid is shown. If this ratio is greater than 1, it indicates that the CNR of the modified protein pore is improved as a result of the increase in translocation time. This is due to the fact that the reduction in bandwidth allowed will decrease the total noise sufficiently to result in an overall increase in CNR. This overall increase in CNR can help enable polymer sequencing and improve sequencing accuracy.

TABLE 4

| Modified Alpha Hemolysin Protein Pore | CNR | Tmax polyA100 (milli seconds) | Weighted CNR | Alpha Hemolysin Protein Pore without the at least One Native Amino Acid Substituted with the Non-Native Amino Acid | Contrast | Tmax polyA100 (milli seconds) | Weighted CNR | Ratio of Modified Pore CNR to Unmodifed Pore CNR |
|---|---|---|---|---|---|---|---|---|
| YY-4S L135I D127K | 2.8 | 1.458 | 3.38 | 4S L135I D127K | 5.0 | 0.279 | 2.64 | 1.28 |
| YY-4S L135I T125S D127K | 1.3 | 1.2 | 1.40 | 4S L135I T125S D127K | 2.9 | 0.154 | 1.14 | 1.23 |

Example 6

Examples of Embodiments

Provided hereafter are non-limiting examples of certain embodiments of the technology.

A1. A polypeptide comprising a modified alpha hemolysin amino acid sequence, wherein:
the modified alpha hemolysin amino acid sequence comprises one or more native amino acid substitutions at one or more positions corresponding to positions 1-109 and 149-293 of SEQ ID NO: 1; and
at least one of the one or more native amino acid substitutions independently is to a non-native hydrophobic amino acid or non-native aromatic amino acid, or non-native aromatic and hydrophobic amino acid.

A2. A polypeptide comprising a modified alpha hemolysin amino acid sequence, wherein:
the modified alpha hemolysin amino acid sequence comprises one or more native amino acid substitutions at one or more positions corresponding to positions 1, 2, 3, 4, 5, 6, 7, 8, 9, 10, 11, 12, 13, 14, 15, 16, 97, 99, 101, 103, 105, 107, 109, 149, 151, 153, 155, 157, 159, 161, 163, 165, 167, 169, 225, 227, 229, 231 or 233 of SEQ ID NO: 1; and
at least one of the one or more native amino acid substitutions independently is to a non-native hydrophobic amino acid or non-native aromatic amino acid, or non-native aromatic and hydrophobic amino acid.

A3. A polypeptide comprising a modified alpha hemolysin amino acid sequence, wherein:
the modified alpha hemolysin amino acid sequence comprises one or more native amino acid substitutions at one or more positions corresponding to positions 105, 107, 109, 149, 151 or 153 of SEQ ID NO: 1; and
at least one of the one or more native amino acid substitutions independently is to a non-native hydrophobic amino acid or non-native aromatic amino acid, or non-native aromatic and hydrophobic amino acid.

A4. A polypeptide comprising a modified alpha hemolysin amino acid sequence, wherein:
the modified alpha hemolysin amino acid sequence comprises one or more native amino acid substitutions at one or more positions corresponding to positions 107, 109, 149 or 151 of SEQ ID NO: 1; and
at least one of the one or more native amino acid substitutions independently is to a non-native hydrophobic amino acid or non-native aromatic amino acid, or non-native aromatic and hydrophobic amino acid.

A5. A polypeptide comprising a modified alpha hemolysin amino acid sequence, wherein:
the modified alpha hemolysin amino acid sequence comprises one or more native amino acid substitutions at one or more positions corresponding to positions 109 or 149 of SEQ ID NO: 1; and
at least one of the one or more native amino acid substitutions independently is to a non-native hydrophobic amino acid or non-native aromatic amino acid, or non-native aromatic and hydrophobic amino acid.

A5a. The polypeptide of any one of embodiments A1 to A5, wherein the modified alpha hemolysin amino acid sequence is modified relative to an amino acid sequence of a reference alpha hemolysin polypeptide.

A5a.1. The polypeptide of any one of embodiments A1 to A5, wherein the amino acid sequence of the reference alpha hemolysin polypeptide comprises at least 90% identity to SEQ ID NO: 1.

A5a.2. The polypeptide of any one of embodiments A1 to A5, wherein the amino acid sequence of the reference alpha hemolysin polypeptide comprises at least 95% identity to SEQ ID NO: 1.

A5a.3. The polypeptide of any one of embodiments A1 to A5, wherein the amino acid sequence of the reference alpha hemolysin polypeptide consists of the amino acid sequence of SEQ ID NO: 1.

A5a.4. The polypeptide of any one of embodiments A1 to A5, wherein the amino acid sequence of the reference alpha hemolysin polypeptide comprises at least 90% homology to SEQ ID NO: 1.

A5a.5. The polypeptide of any one of embodiments A1 to A5, wherein the amino acid sequence of the reference alpha hemolysin polypeptide comprises at least 95% homology to SEQ ID NO: 1.

A5.1. The polypeptide comprising a modified alpha hemolysin amino acid sequence of any one of embodiments A1 to A5a wherein the non-native amino acid is hydrophobic.

A5.2. The polypeptide comprising a modified alpha hemolysin amino acid sequence of any one of embodiments A1 to A5a wherein the non-native amino acid is aromatic.

A5.3. The polypeptide comprising a modified alpha hemolysin amino acid sequence of any one of embodiments A1 to A5.2 wherein the non-native amino acid is hydrophobic and aromatic.

A5.4. The polypeptide comprising a modified alpha hemolysin amino acid sequence of any one of embodiments A1 to A5.3 wherein the non-native amino acid is larger than the native amino acid.

A5.5. The polypeptide comprising a modified alpha hemolysin amino acid sequence of any one of embodiments A1 to A5.4, wherein the non-native amino acid is naturally occurring.

A5.6. The polypeptide comprising a modified alpha hemolysin amino acid sequence of any one of embodiments A1 to A5.4, wherein the non-native amino acid is synthetic.

A6. The polypeptide comprising a modified alpha hemolysin amino acid sequence of any one of embodiments A1 to A5.1, 5.4 or 5.5, wherein the non-native amino acid is methionine (M).

A7. The polypeptide comprising a modified alpha hemolysin amino acid sequence of any one of embodiments A1 to A5.1, A5.3, 5.4 and 5.5, wherein the non-native amino acid is selected from the group consisting of phenylalanine (F), tryptophan (W) and tyrosine (Y).

A8. The polypeptide comprising a modified alpha hemolysin amino acid sequence of embodiment A7, wherein the non-native amino acid is phenylalanine (F).

A9. The polypeptide comprising a modified alpha hemolysin amino acid sequence of embodiment A7, wherein the non-native amino acid is tryptophan (W).

A10. The polypeptide comprising a modified alpha hemolysin amino acid sequence of embodiment A7, wherein the non-native amino acid is tyrosine (Y).

A11. The polypeptide comprising a modified alpha hemolysin amino acid sequence of any preceding embodiment wherein at least two native amino acids are substituted with non-native amino acids.

A12. The polypeptide comprising a modified alpha hemolysin amino acid sequence of any preceding embodiment, wherein at least three native amino acids are substituted with non-native amino acids.

A13. The polypeptide comprising a modified alpha hemolysin amino acid sequence of any preceding embodiment, wherein at least four native amino acids are substituted with non-native amino acids.

A13.1. The polypeptide comprising a modified alpha hemolysin amino acid sequence of any one of embodiments A11 to A13, wherein the non-native amino acids are the same.

A13.2. The polypeptide comprising a modified alpha hemolysin amino acid sequence of any one of embodiments A11 to A13, wherein the non-native amino acids are not the same.

A13.3. The polypeptide comprising a modified alpha hemolysin amino acid sequence of any one of embodiments A12 to A13, wherein at least two of the non-native amino acids are the same.

A14. The polypeptide comprising a modified alpha hemolysin amino acid sequence of any preceding embodiment, wherein at least one beta barrel amino acid at any beta barrel amino acid position 111, 113, 115, 117, 119, 121, 123, 125, 127, 129, 131, 133, 135, 137, 139, 141, 143, 145 or 147 is replaced with a different amino acid.

A15. The polypeptide comprising a modified alpha hemolysin amino acid sequence of any preceding embodiment, wherein at least two beta barrel amino acids at any beta barrel amino acid position 111, 113, 115, 117, 119, 121, 123, 125, 127, 129, 131, 133, 135, 137, 139, 141, 143, 145 or 147 are replaced with a different amino acid.

A16. The polypeptide comprising a modified alpha hemolysin amino acid sequence of any preceding embodiment, wherein at least three beta barrel amino acids at any beta barrel amino acid position 111, 113, 115, 117, 119, 121, 123, 125, 127, 129, 131, 133, 135, 137, 139, 141, 143, 145 or 147 are replaced with a different amino acid.

A17. The polypeptide comprising a modified alpha hemolysin amino acid sequence of any preceding embodiment, wherein at least four beta barrel amino acids at any beta barrel amino acid position 111, 113, 115, 117, 119, 121, 123, 125, 127, 129, 131, 133, 135, 137, 139, 141, 143, 145 or 147 are replaced with a different amino acid.

A18. The polypeptide comprising a modified alpha hemolysin amino acid sequence of any preceding embodiment, wherein at least five beta barrel amino acids at any beta barrel amino acid position 111, 113, 115, 117, 119, 121, 123, 125, 127, 129, 131, 133, 135, 137, 139, 141, 143, 145 or 147 are replaced with a different amino acid.

A18.1. The polypeptide comprising a modified alpha hemolysin amino acid sequence of any one of embodiments A14 to A18, wherein the different amino acid is a naturally occurring amino acid.

A18.2. The polypeptide comprising a modified alpha hemolysin amino acid sequence of any one of embodiments A14 to A18, wherein the different amino acid is a synthetic amino acid.

A19. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 20 percent compared to the translocation time of the polymer through an alpha hemolysin polypeptide without the at least one native amino acid substituted with the non-native amino acid.

A20. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 50 percent compared to the translocation time of the polymer through an alpha hemolysin polypeptide without the at least one native amino acid substituted with the non-native amino acid.

A21. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 100 percent compared to the translocation time of the polymer through an alpha hemolysin polypeptide without the at least one native amino acid substituted with the non-native amino acid.

A22. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 200 percent compared to the translocation time of the polymer through an alpha hemolysin polypeptide without the at least one native amino acid substituted with the non-native amino acid.

A23. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 300 percent compared to the translocation time of the polymer through an alpha hemolysin polypeptide without the at least one native amino acid substituted with the non-native amino acid.

A24. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 400 percent compared to the translocation time of the polymer through an alpha hemolysin polypeptide without the at least one native amino acid substituted with the non-native amino acid.

A24. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 500 percent compared to the translocation time of the polymer through an alpha hemolysin polypeptide without the at least one native amino acid substituted with the non-native amino acid.

A25. The polypeptide comprising a modified alpha hemolysin amino acid sequence of any preceding embodiment, wherein the at least one native amino acid substituted with the non-native amino acid enables an increase in a translocation time of a polymer through the polypeptide comprising a modified alpha hemolysin amino acid sequence by at least 1000 percent compared to the translocation time of the polymer through an alpha hemolysin polypeptide without the at least one native amino acid substituted with the non-native amino acid.

A26. The polypeptide comprising a modified alpha hemolysin amino acid sequence of any one of embodiments A19 to A25 that permits a measurement of a first level and a second level within a residual current of the polypeptide comprising a modified alpha hemolysin amino acid sequence, as the polymer translocates through the polypeptide comprising a modified alpha hemolysin amino acid sequence, with a contrast signal to noise ratio (CNR) computed at a predetermined filter frequency;
  which polymer comprises two or more sections, each of which sections comprises at least a portion of a monomer;
  which CNR is calculated as a contrast signal divided by a noise value;
  which contrast signal is calculated as the difference between the first level and the second level, wherein:
  each level used for calculating the CNR correlates to a composition of a section of the polymer,
  the first level and the second level are measurably distinct; and
  which noise value is computed at the predetermined filter frequency.

A27. The polypeptide comprising a modified alpha hemolysin amino acid sequence of embodiment A26, wherein the increase in the translocation time enables a lower predetermined filter frequency to be used in the computation of the CNR.

A28. The polypeptide comprising a modified alpha hemolysin amino acid sequence of embodiment A27, wherein the lower predetermined filter frequency results in a lower noise value.

A29. The polypeptide comprising a modified alpha hemolysin amino acid sequence of embodiment A28, wherein the lower noise value results in a higher CNR.

A29.1 The polypeptide comprising a modified alpha hemolysin amino acid sequence of embodiment A27, wherein the lower predetermined filter frequency results in a higher Weighted CNR.

A30. The polypeptide comprising a modified alpha hemolysin amino acid sequence of any preceding embodiment, wherein the native amino acid T109 is substituted with the non-native amino acid tyrosine (T109Y).

A31. The polypeptide comprising a modified alpha hemolysin amino acid sequence of any preceding embodiment, wherein the native amino acid V149 is substituted with the non-native amino acid tyrosine (V149Y).

A32. The polypeptide comprising a modified alpha hemolysin amino acid sequence of any preceding embodiment, wherein the native amino acids T109 and V149 are substituted with the non-native amino acid tyrosine (T109Y and V149Y).

A33. The polypeptide comprising a modified alpha hemolysin amino acid sequence of any one of embodiments A1 to A32 wherein the native amino acids T109 and V149 are substituted with the non-native amino acids tyrosine and tryptophan respectively (T109Y and V149W).

A34. The polypeptide comprising a modified alpha hemolysin amino acid sequence of any one of embodiments A14 to A33, wherein the native amino acids T109 and V149 are substituted with the non-native amino acid tyrosine (T109Y and V149Y) and wherein the beta barrel amino acids E111, M113, D127, L135, T145 and K147 are substituted with the different amino acids serine, serine, lysine, isoleucine, serine and serine respectively (E111S, M113S, D127K, L135I, T145S, and K147S).

A35. The polypeptide comprising a modified alpha hemolysin amino acid sequence of any one of embodiments A14 to A33, wherein the native amino acids T109 and V149 are substituted with the non-native amino acid tyrosine (T109Y and V149Y) and wherein the beta barrel amino acids E111, M113, L135, T145 and K147 are substituted with the different amino acids serine, serine, isoleucine, serine and serine respectively (E111S, M113S, L135I, T145S, and K147S).

A36. The polypeptide of any preceding embodiment, wherein the modified alpha hemolysin sequence comprises the SEQ ID NO: 1 except for the one or more native amino acids substitutions and the one or more different amino acid replacements.

A37. The polypeptide of any one of embodiments A1 to A36, wherein the polypeptide is an isolated polypeptide.

A38. The polypeptide of embodiment A1, comprising the modified alpha hemolysin amino acid sequence of SEQ ID NO: 2.

A39. The polypeptide of embodiment A1, comprising the modified alpha hemolysin amino acid sequence of SEQ ID NO: 3.

A40. The polypeptide of any one of embodiments A1 to A37, comprising an amino acid sequence with 90% identity to SEQ ID NO: 2.

A41. The polypeptide of any one of embodiments A1 to A37, comprising an amino acid sequence with 90% identity to SEQ ID NO: 3.

B1. The method of using the polypeptide comprising a modified alpha hemolysin amino acid sequence of any one of embodiments A1 to A39 to sequence a polymer.

C1. The method of increasing the translocation time of a polymer using a polypeptide comprising a modified alpha hemolysin amino acid sequence of any one of embodiments A1 to A40, relative to a translocation time of the polymer through a reference alpha hemolysin polypeptide.

D1. The method of translocating a polymer through a polypeptide comprising a modified alpha hemolysin amino acid sequence of any one of embodiments A1 to A37.

E1. A modified alpha hemolysin polypeptide comprising a modified alpha hemolysin amino acid sequence, wherein:
 the modified alpha hemolysin amino acid sequence comprises one or more amino acid substitutions at one or more positions corresponding to positions 1-109 and 149-293 of SEQ ID NO: 1; and
 at least one of the one or more amino acid substitutions independently is to a non-native amino acid, wherein the non-native amino acid is hydrophobic or aromatic, or hydrophobic and aromatic.

E2. The polypeptide of embodiment E1, wherein the modified alpha hemolysin amino acid sequence comprises one or more substitutions located within a beta barrel.

E3. The polypeptide of embodiment E2, wherein the beta barrel comprises positions 111, 113, 115, 117, 119, 121, 123, 125, 127, 129, 131, 133, 135, 137, 139, 141, 143, 145 and 147 of SEQ ID NO: 1.

E4. The polypeptide of embodiment E2 or E3, wherein the modified alpha hemolysin amino acid sequence comprises at least two amino acid substitutions located in the beta barrel.

E5. The polypeptide of any one of embodiments E2 to E4, wherein the modified alpha hemolysin amino acid sequence comprises at least three amino acid substitutions located in the beta barrel.

E6. The polypeptide of any one of embodiments E2 to E5, wherein the modified alpha hemolysin amino acid sequence comprises at least four amino acid substitutions located in the beta barrel.

E7. The polypeptide of any one of embodiments E2 to E6, wherein the modified alpha hemolysin amino acid sequence comprises at least five amino acid substitutions located in the beta barrel.

E8. The polypeptide of embodiment E1, wherein the one or more positions correspond to positions 1, 2, 3, 4, 5, 6, 7, 8, 9, 10, 11, 12, 13, 14, 15, 16, 97, 99, 101, 103, 105, 107, 109, 149, 151, 153, 155, 157, 159, 161, 163, 165, 167, 169, 225, 227, 229, 231 or 233 of SEQ ID NO: 1.

E9. The polypeptide of embodiment E1, wherein the one or more positions correspond to positions 105, 107, 109, 149, 151 or 153 of SEQ ID NO: 1.

E10. The polypeptide of embodiment E1, wherein the one or more positions correspond to positions 107, 109, 149 or 151 of SEQ ID NO: 1.

E11. The polypeptide of embodiment E1, wherein the one or more positions correspond to positions 109 or 149 of SEQ ID NO: 1.

E12. The polypeptide of any one of embodiments E1 to E11, wherein the non-native amino acid is hydrophobic.

E13. The polypeptide of any one of embodiments E1 to E12, wherein the non-native amino acid is aromatic.

E14. The polypeptide of any one of embodiments E1 to E13, wherein the non-native amino acid is hydrophobic and aromatic.

E15. The polypeptide of any one of embodiments E1 to E14, wherein the one or more amino acid substitutions independently is to one or more larger amino acids.

E16. The polypeptide of any one of embodiments E1 to E15, wherein the one or more amino acid substitutions independently is to one or more naturally occurring amino acids.

E17. The polypeptide of any one of embodiments E1 to E16, wherein the one or more amino acid substitutions independently is to one or more synthetic amino acids.

E18. The polypeptide of any one of embodiments E1 to E7, E10 and E11, wherein the one or more amino acid substitutions independently is to one or more methionines.

E19. The polypeptide of any one of embodiments E1 to E13, E15 and E16, wherein the non-native amino acid is selected from the group consisting of phenylalanine (F), tryptophan (W) and tyrosine (Y).

E20. The polypeptide of embodiment E19, wherein the non-native amino acid is phenylalanine (F).

E21. The polypeptide of embodiment E19, wherein the non-native amino acid is tryptophan (W).

E22. The polypeptide of embodiment E19, wherein the non-native amino acid is tyrosine (Y).

E23. The polypeptide of any one of embodiments E1 to E22, wherein the modified alpha hemolysin amino acid sequence comprises at least two amino acid substitutions.

E24. The polypeptide of any one of embodiments E1 to E22, wherein the modified alpha hemolysin amino acid sequence comprises at least three amino acid substitutions E25. The polypeptide of any one of embodiments E1 to E22, wherein the modified alpha hemolysin amino acid sequence comprises at least four amino acid substitutions.

E26. The polypeptide of embodiment E23, wherein the at least two amino acid substitutions are to non-native amino acids that are the same.

E27. The polypeptide of embodiment E23, wherein the at least two amino acid substitutions are to non-native amino acids that are not the same.

E28. The polypeptide of embodiment E23, wherein the at least two amino acid substitutions are to at least two non-native amino acids that are not the same.

E29. The polypeptide of any one of embodiments E1 to E28, comprising a first translocation time determined for a polymer translocating through the polypeptide, wherein the first translocation time is at least 20% longer than a second translocation time for the polymer as determined for a reference alpha hemolysin protein.

E29.1. The polypeptide of any one of embodiments E1 to E28, comprising a first translocation time determined for a polymer translocating through the polypeptide, wherein the first translocation time is at least 20% longer than a second translocation time for the polymer as determined for a reference alpha hemolysin protein comprising one or more amino acid substitutions located in a beta barrel.

E30. The polypeptide of embodiment E29 or E29.1, wherein the first translocation time is at least 50% longer than the second translocation time.

E31. The polypeptide of embodiment E29 or E29.1, wherein the first translocation time is at least 100% longer than the second translocation time.

E32. The polypeptide of embodiment E29 or E29.1, wherein the first translocation time is at least 200% longer than the second translocation time.

E33. The polypeptide of embodiment E29 or E29.1, wherein the first translocation time is at least 300% longer than the second translocation time.

E34. The polypeptide of embodiment E29 or E29.1, wherein the first translocation time is at least 400% longer than the second translocation time.

E35. The polypeptide of embodiment E29 or E29.1, wherein the first translocation time is at least 500% longer than the second translocation time.

E36. The polypeptide of embodiment E29 or E29.1, wherein the first translocation time is at least 1000% longer than the second translocation time.

E37. The polypeptide of any one of embodiments E29 to E36, wherein the polymer is a polynucleotide.

E38. The polypeptide of embodiment E37, wherein the polynucleotide consists of polyA, polyC, polyT, polyU or polyG.

E39. The polypeptide of any one of embodiments E29 to E36, wherein the polymer is a polypeptide.

E40. The polypeptide of any one of embodiments E29 to E39, wherein the reference alpha hemolysin protein comprises the sequence of SEQ ID NO: 1.

E41. The polypeptide of any one of embodiments E29 to E40 that permits a measurement of a first level and a second level within a residual current of the polypeptide, as the polymer translocates through the polypeptide with a contrast signal to noise ratio (CNR) computed at a predetermined filter frequency;
 which polymer comprises two or more sections, each of which sections comprises at least a portion of a monomer;
 which CNR is calculated as a contrast signal divided by a noise value;
 which contrast signal is calculated as the difference between the first level and the second level, wherein:
 each level used for calculating the CNR correlates to a composition of a section of the polymer,
 the first level and the second level are measurably distinct; and
 which noise value is computed at the predetermined filter frequency.

E42. The polypeptide of embodiment E41, wherein the increase in the translocation time enables a lower predetermined filter frequency to be used in the computation of the CNR.

E43. The polypeptide of embodiment E42, wherein the lower predetermined filter frequency results in a lower noise value.

E44. The polypeptide of embodiment E43, wherein the lower noise value results in a higher CNR.

E45. The polypeptide of any one of embodiments E1 to E44, wherein threonine at position 109 is substituted with tyrosine.

E46. The polypeptide of any one of embodiments E1 to E46, wherein valine at position 149 is substituted with tyrosine.

E47. The polypeptide of any one of embodiments E1 to E46, wherein threonine at position 109 is substituted with tyrosine and valine at position 149 is substituted with tyrosine.

E48. The polypeptide of any one of embodiments E1 to E45, wherein threonine at position 109 is substituted with tyrosine and valine at position 149 is substituted with tryptophan.

E49. The polypeptide of embodiment E47, wherein glutamate, methionine, aspartic acid, leucine, threonine and lysine at positions 111, 113, 127, 135, 145 and 147, respectively, are substituted with serine, serine, lysine, isoleucine, serine and serine respectively.

E50. The polypeptide of embodiment E47, wherein glutamate, methionine, leucine, threonine and lysine at positions 111, 113, 135, 145 and 147, respectively, are substituted with serine, serine, isoleucine, serine and serine respectively.

E51. The polypeptide of any one of embodiments E1 to E50, wherein the modified alpha hemolysin sequence comprises the sequence of SEQ ID NO: 1 except for the one or more amino acid substitutions.

E52. The polypeptide of any one of embodiments E1 to E51, wherein the polypeptide is an isolated polypeptide.

E53. The polypeptide of any one of embodiments E1 to E52, wherein the modified alpha hemolysin amino acid sequence is modified relative to an amino acid sequence of a reference alpha hemolysin polypeptide.

E54. The polypeptide of any one of embodiments E1 to E52, wherein the amino acid sequence of the reference alpha hemolysin polypeptide comprises at least 90% identity to SEQ ID NO: 1.

E55. The polypeptide of any one of embodiments E1 to E52, wherein the amino acid sequence of the reference alpha hemolysin polypeptide comprises at least 95% identity to SEQ ID NO: 1.

E56. The polypeptide of any one of embodiments E1 to E52, wherein the amino acid sequence of the reference alpha hemolysin polypeptide consists of the amino acid sequence of SEQ ID NO: 1.

E57. The polypeptide of any one of embodiments E1 to E52, wherein the amino acid sequence of the reference alpha hemolysin polypeptide comprises at least 90% homology to SEQ ID NO: 1.

E58. The polypeptide of any one of embodiments E1 to E52, wherein the amino acid sequence of the reference alpha hemolysin polypeptide comprises at least 95% homology to SEQ ID NO: 1.

E59. The polypeptide of embodiment E1, comprising the modified alpha hemolysin amino acid sequence of SEQ ID NO: 2.

E60. The polypeptide of embodiment E1, comprising the modified alpha hemolysin amino acid sequence of SEQ ID NO: 3.

E61. The polypeptide of any one of embodiments E1 to E58, comprising an amino acid sequence with 90% identity to SEQ ID NO: 2.

E62. The polypeptide of any one of embodiments E1 to E58, comprising an amino acid sequence with 90% identity to SEQ ID NO: 3.

F1. A method of sequencing a polymer with a modified alpha hemolysin polypeptide comprising:
(a) contacting a polymer with a modified alpha hemolysin polypeptide, wherein the modified alpha hemolysin polypeptide comprises one or more amino acid substitutions relative to an amino acid sequence of a reference alpha hemolysin protein, and
(b) determining the sequence of the polymer according to one or more electrical changes across or through the modified alpha hemolysis protein pore.

F2. The method of embodiment F1, wherein the reference alpha hemolysis protein comprises the sequence of SEQ ID NO:1.

F3. The method of embodiment F1 or F2, wherein the modified alpha hemolysin polypeptide comprises one or more amino acid substitutions selected from one or more positions corresponding to amino acids 1-109 and 149-293 of SEQ ID NO: 1., wherein the one or more amino acids are substituted with a non-native hydrophobic amino acid, non-native aromatic amino acid, or non-native aromatic and hydrophobic amino acid.

F4. The method of embodiment F3, wherein the one or more amino acid substitutions are selected from one or more positions of 1 to 16, 97, 99, 101, 103, 105, 107, 109, 149, 151, 153, 155, 157, 159, 161, 163, 165, 167, 169, 225, 227, 229, 231 or 233 of SEQ ID NO: 1.

F5. The method of embodiment F3, wherein one or more amino acids substitutions are selected from one or more positions of 105, 107, 109, 149, 151 or 153 of SEQ ID NO: 1.

F6. The method of embodiment F3, wherein one or more amino acids substitutions are selected from one or more positions of 107, 109, 149 or 151 of SEQ ID NO: 1.

F7. The method of embodiment F2, wherein one or more amino acids substitutions are selected from one or more positions of 109 or 149 of SEQ ID NO: 1.

F8. The method of any one of embodiments F1 to F7, wherein the reference alpha hemolysin protein comprises one or more amino acid substitutions located in a beta barrel.

F9. The method of any one of embodiments F1 to F8, wherein the modified alpha hemolysin polypeptide is a modified alpha hemolysin polypeptide of any one of embodiments E1 to E61.

G1. A method for translocating a polymer through a modified alpha hemolysin polypeptide comprising: contacting a polymer with a modified alpha hemolysin polypeptide under conditions in which the polymer translocates through the modified alpha hemolysin polypeptide,
wherein the modified alpha hemolysin polypeptide comprises an amino acid sequence of a reference alpha hemolysin protein comprising one or more amino acid substitutions, and
determining a translocation time of the polymer through the modified alpha hemolysin polypeptide.

G1.2. The method of embodiment G1, wherein the translocation time of the polymer through the modified alpha hemolysin polypeptide is at least 20% longer than a translocation time of the polymer through the reference alpha hemolysin protein.

G2. The method of embodiment G1 or G1.2, wherein the reference alpha hemolysis protein comprises the sequence of SEQ ID NO:1.

G3. The method of embodiment G2, wherein, for the modified alpha hemolysin polypeptide, one or more amino acids selected from one or more positions of 1-109 and 149-293 of SEQ ID NO: 1 are substituted with a non-native hydrophobic amino acid, non-native aromatic amino acid, or non-native aromatic and hydrophobic amino acid.

G4. The method of embodiment G2, wherein, for the modified alpha hemolysin polypeptide, one or more amino acids selected from one or more positions of 1 to 16, 97, 99, 101, 103, 105, 107, 109, 149, 151, 153, 155, 157, 159, 161, 163, 165, 167, 169, 225, 227, 229, 231 or 233 of SEQ ID NO: 1 are substituted with a non-native hydrophobic amino acid, non-native aromatic amino acid, or non-native aromatic and hydrophobic amino acid.

G5. The method of embodiment G2, wherein, for the modified alpha hemolysin polypeptide, one or more amino acids selected from one or more positions of 105, 107, 109, 149, 151 or 153 of SEQ ID NO: 1 are substituted with a non-native hydrophobic amino acid or non-native aromatic amino acid, or non-native aromatic and hydrophobic amino acid.

G6. The method of embodiment G2, wherein, for the modified alpha hemolysin polypeptide, one or more amino acids selected from one or more positions of 107, 109, 149 or 151 of SEQ ID NO: 1 are substituted with a non-native hydrophobic amino acid or non-native aromatic amino acid, or non-native aromatic and hydrophobic amino acid.

G7. The method of embodiment G2, wherein, for the modified alpha hemolysin polypeptide, one or more amino acids selected from one or more positions of 109 or 149 of SEQ ID NO: 1 are substituted with a non-native hydrophobic amino acid, non-native aromatic amino acid, or non-native aromatic and hydrophobic amino acid.

G8. The method of any one of embodiments G1 to G7, wherein the reference alpha hemolysin protein comprises one or more amino acid substitutions located in a beta barrel.

G9. The method of any one of embodiments G1 to G8, wherein the modified alpha hemolysin polypeptide is a modified alpha hemolysin polypeptide of any one of embodiments E1 to E52.

H1. A method of increasing the translocation time of a polymer through a modified alpha hemolysin polypeptide comprising:
(a) substituting one or more amino acids of a reference alpha hemolysin polypeptide, wherein a modified alpha hemolysin polypeptide is generated, and
(b) contacting the modified alpha hemolysin polypeptide with a polymer under conditions in which the polymer translocates through the modified alpha hemolysin polypeptide.

H1.1. The method of embodiment H1, wherein the translocation time of the polymer through the modified alpha hemolysin polypeptide is at least 20% longer than a translocation time of the polymer through the reference alpha hemolysin protein.

H2. The method of embodiment H1 or H1.1, wherein the reference alpha hemolysis protein comprises the sequence of SEQ ID NO:1.

H3. The method of embodiment H2, wherein, for the modified alpha hemolysin polypeptide, one or more amino acids selected from one or more positions of 1-109 and 149-293 of SEQ ID NO: 1 are substituted with a non-native hydrophobic amino acid, non-native aromatic amino acid, or non-native aromatic and hydrophobic amino acid.

H4. The method of embodiment H2, wherein, for the modified alpha hemolysin polypeptide, one or more amino acids selected from one or more positions of 1 to 16, 97, 99, 101, 103, 105, 107, 109, 149, 151, 153, 155, 157, 159, 161, 163, 165, 167, 169, 225, 227, 229, 231 or 233 of SEQ ID NO: 1 are substituted with a non-native hydrophobic amino acid, non-native aromatic amino acid, or non-native aromatic and hydrophobic amino acid.

H5. The method of embodiment H2, wherein, for the modified alpha hemolysin polypeptide, one or more amino acids selected from one or more positions of 105, 107, 109, 149, 151 or 153 of SEQ ID NO: 1 are substituted with a non-native hydrophobic amino acid or non-native aromatic amino acid, or non-native aromatic and hydrophobic amino acid.

H6. The method of embodiment H2, wherein, for the modified alpha hemolysin polypeptide, one or more amino acids selected from one or more positions of 107, 109, 149 or 151 of SEQ ID NO: 1 are substituted with a non-native hydrophobic amino acid or non-native aromatic amino acid, or non-native aromatic and hydrophobic amino acid.

H7. The method of embodiment H2, wherein, for the modified alpha hemolysin polypeptide, one or more amino acids selected from one or more positions of 109 or 149 of SEQ ID NO: 1 are substituted with a non-native hydrophobic amino acid, non-native aromatic amino acid, or non-native aromatic and hydrophobic amino acid.

H8. The method of any one of embodiments H1 to H7, wherein the reference alpha hemolysin protein comprises one or more amino acid substitutions located in a beta barrel.

H9. The method of any one of embodiments H1 to H8, wherein the modified alpha hemolysin polypeptide is a modified alpha hemolysin polypeptide of any one of embodiments E1 to E52.

I1. A nanopore device comprising a modified alpha hemolysin protein of any one of embodiments E1 to E52.

I2. The nanopore device of embodiment I1, wherein the modified alpha hemolysin protein comprises an amino acid sequence of a reference alpha hemolysis protein with one or more amino acid substitutions.

I3. The nanopore device of embodiment I2, wherein the reference alpha hemolysin protein comprises an amino acid sequence of SEQ ID NO: 1.

I4. The nanopore device of embodiment I3, wherein, for the modified alpha hemolysin polypeptide, one or more amino acids selected from one or more positions of 1-109 and 149-293 of SEQ ID NO: 1 are substituted with a non-native hydrophobic amino acid, non-native aromatic amino acid, or non-native aromatic and hydrophobic amino acid.

I5. The nanopore device of embodiment I3, wherein, for the modified alpha hemolysin polypeptide, one or more amino acids selected from one or more positions of 1 to 16, 97, 99, 101, 103, 105, 107, 109, 149, 151, 153, 155, 157, 159, 161, 163, 165, 167, 169, 225, 227, 229, 231 or 233 of SEQ ID NO: 1 are substituted with a non-native hydrophobic amino acid, non-native aromatic amino acid, or non-native aromatic and hydrophobic amino acid.

I6. The nanopore device of embodiment I3, wherein, for the modified alpha hemolysin polypeptide, one or more amino acids selected from one or more positions of 105, 107, 109, 149, 151 or 153 of SEQ ID NO: 1 are substituted with a non-native hydrophobic amino acid or non-native aromatic amino acid, or non-native aromatic and hydrophobic amino acid.

I7. The nanopore device of embodiment I3, wherein, for the modified alpha hemolysin polypeptide, one or more amino acids selected from one or more positions of 107, 109, 149 or 151 of SEQ ID NO: 1 are substituted with a non-native hydrophobic amino acid or non-native aromatic amino acid, or non-native aromatic and hydrophobic amino acid.

I8. The nanopore device of embodiment I3, wherein, for the modified alpha hemolysin polypeptide, one or more amino acids selected from one or more positions of 109 or 149 of SEQ ID NO: 1 are substituted with a non-native hydrophobic amino acid, non-native aromatic amino acid, or non-native aromatic and hydrophobic amino acid.

I9. The nanopore device of any one of embodiments I1 to I8, wherein the reference alpha hemolysin protein comprises one or more amino acid substitutions located in a beta barrel.

I10. The nanopore device of any one of embodiments I1 to I9, wherein the modified alpha hemolysin polypeptide is a modified alpha hemolysin polypeptide of any one of embodiments E1 to E52.

I11. The nanopore device of any one of embodiments I1 to I10, comprising a lipid bilayer in which the modified alpha hemolysin polypeptide resides.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method of translocating a polynucleotide through a modified alpha hemolysin polypeptide comprising:

contacting a polynucleotide with a modified alpha hemolysin polypeptide, wherein the modified alpha hemolysin polypeptide comprises an amino acid substitution of a non-native amino acid for a native amino acid at a position outside a beta-barrel region corresponding to position 109 of a wild-type Staphylococcus aureus alpha hemolysin polypeptide of 293 amino acids and an amino acid substitution of a non-native amino acid for a native amino acid at a position corresponding to position 149 of a wild-type Staphylococcus aureus alpha hemolysin polypeptide of 293 amino acids, wherein the amino acid residues of the wild-type Staphylococcus aureus alpha hemolysin polypeptide align with the C-terminal 293 amino acid residues of the Staphylococcus aureus alpha hemolysin polypeptide of SEQ ID NO. 1, and the non-native amino acids are naturally occurring or synthetic aromatic amino acids and/or naturally occurring or synthetic hydrophobic amino acids;

translocating the polynucleotide through the modified alpha hemolysin polypeptide under conditions in which the polynucleotide translocates through the modified alpha hemolysin polypeptide slower than translocation through the polypeptide without the amino acid substitutions and the translocation time of the polynucleotide through the modified polypeptide is at least 200% longer than a translocation time of the polynucleotide through the polypeptide without the amino acid substitutions; and detecting one or more electrical changes across or through the modified alpha hemolysin polypeptide associated with translocation of the polynucleotide.

2. The method of claim 1, wherein the increase in the translocation time enables a lower predetermined filter frequency to be used to examine current associated with translocation of the polynucleotide through the modified alpha hemolysin polypeptide, than the predetermined filter frequency used for the polypeptide without the substitutions.

3. The method of claim 2, wherein the lower predetermined filter frequency results in a lower noise level for the examination of current associated with translocation of the polynucleotide.

4. The method of claim 3, wherein the lower noise level, results in a higher signal to noise ratio for the polynucleotide translocation.

5. The method of claim 1, further comprising determining the identity of the polynucleotide, as it translocates through the modified alpha hemolysin polypeptide, according to one or more electrical changes across or through the modified alpha hemolysin polypeptide.

6. The method of claim 1, further comprising determining the sequence of the polynucleotide, as it translocates through the modified alpha hemolysin polypeptide, according to one or more electrical changes across or through the modified alpha hemolysin polypeptide.

7. The method of claim 1 further comprising one or more amino acid substitutions of a non-native amino acid for a native amino acid at one or more positions outside a beta-barrel region corresponding to positions 107, 151 or 153 of a wild-type Staphylococcus aureus alpha hemolysin polypeptide of 293 amino acids, wherein the amino acid residues of the wild-type Staphylococcus aureus alpha hemolysin polypeptide align with the C-terminal 293 amino acid residues of the Staphylococcus aureus alpha hemolysin polypeptide of SEQ ID NO. 1, and the non-native amino acids are naturally occurring or synthetic aromatic amino acids and/or naturally occurring or synthetic hydrophobic amino acids.

8. The method of claim 1, wherein at least one of the non-native amino acids is tryptophan (W).

9. The method of claim 1, wherein at least one of the non-native amino acids is tyrosine (Y).

10. The method of claim 1, further comprising one or more substitutions at positions that are part of the sequence of a beta barrel region, corresponding to positions 111, 113, 115, 117, 119, 121, 123, 125, 127,129, 131, 133, 135, 137, 139, 141, 143, 145 or 147 of a wild-type Staphylococcus aureus alpha hemolysin polypeptide of 293 amino acids, wherein the amino acid residues of the wild-type Staphylococcus aureus alpha hemolysin polypeptide align with the C-terminal 293 amino acid residues of the Staphylococcus aureus alpha hemolysin polypeptide of SEQ ID NO. 1.

11. The method of claim 7, further comprising one or more substitutions at positions that are part of the sequence of a beta barrel region corresponding to positions 111, 113, 115, 117, 119, 121, 123, 125, 127,129, 131, 133, 135, 137, 139, 141, 143, 145 or 147 of a wild-type Staphylococcus aureus alpha hemolysin polypeptide of 293 amino acids, wherein the amino acid residues of the wild-type Staphylococcus aureus alpha hemolysin polypeptide align with the C-terminal 293 amino acid residues of the Staphylococcus aureus alpha hemolysin polypeptide of SEQ ID NO. 1.

12. The method of claim 7, wherein the increase in the translocation time enables a lower predetermined filter frequency to be used to examine current associated with translocation of the polynucleotide through the modified alpha hemolysin polypeptide, than the predetermined filter frequency used for the polypeptide without the substitutions.

13. The method of claim 12, wherein the lower predetermined filter frequency results in a lower noise level for the examination of current associated with translocation of the polynucleotide.

14. The method of claim 13, wherein the lower noise level, results in a higher signal to noise ratio for the polynucleotide translocation.

15. The method of claim 7, further comprising determining the identity of the polynucleotide as it translocates through the modified alpha hemolysin polypeptide, according to one or more electrical changes across or through the modified alpha hemolysin polypeptide.

16. The method of claim 7, further comprising determining the sequence of the polynucleotide as it translocates through the modified alpha hemolysin polypeptide, according to one or more electrical changes across or through the modified alpha hemolysin polypeptide.

17. The method of claim 7, wherein at least one of the non-native amino acids is tryptophan (W).

18. The method of claim 7, wherein at least one of the non-native amino acids is tyrosine (Y).

* * * * *

SEQUENCE LISTING

<160> NUMBER OF SEQ ID NOS: 6

<210> SEQ ID NO 1
<211> LENGTH: 294
<212> TYPE: PRT
<213> ORGANISM: Staphylococcus aureus

<400> SEQUENCE: 1

```
Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn
    290
```

<210> SEQ ID NO 2
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Asp Ser Asp Ile Asn Ile Lys Thr Gly Thr Thr Asp Ile Gly

```
            1               5                  10                 15
Ser Asn Thr Thr Val Lys Thr Gly Asp Leu Val Thr Tyr Asp Lys Glu
                20                 25                 30

Asn Gly Met His Lys Lys Val Phe Tyr Ser Phe Ile Asp Asp Lys Asn
                35                 40                 45

His Asn Lys Lys Leu Leu Val Ile Arg Thr Lys Gly Thr Ile Ala Gly
    50                  55                 60

Gln Tyr Arg Val Tyr Ser Glu Glu Gly Ala Asn Lys Ser Gly Leu Ala
65                  70                 75                  80

Trp Pro Ser Ala Phe Lys Val Gln Leu Gln Leu Pro Asp Asn Glu Val
                85                 90                 95

Ala Gln Ile Ser Asp Tyr Tyr Pro Arg Asn Ser Ile Asp Tyr Lys Ser
                100                105                110

Tyr Ser Ser Thr Leu Thr Tyr Gly Phe Asn Gly Asn Val Thr Gly Lys
                115                120                125

Asp Thr Gly Lys Ile Gly Gly Ile Ile Gly Ala Asn Val Ser Ile Gly
    130                 135                140

His Ser Leu Ser Tyr Tyr Gln Pro Asp Phe Lys Thr Ile Leu Glu Ser
145                 150                155                 160

Pro Thr Asp Lys Lys Val Gly Trp Lys Val Ile Phe Asn Asn Met Val
                165                170                175

Asn Gln Asn Trp Gly Pro Tyr Asp Arg Asp Ser Trp Asn Pro Val Tyr
                180                185                190

Gly Asn Gln Leu Phe Met Lys Thr Arg Asn Gly Ser Met Lys Ala Ala
                195                200                205

Asp Asn Phe Leu Asp Pro Asn Lys Ala Ser Ser Leu Leu Ser Ser Gly
    210                 215                220

Phe Ser Pro Asp Phe Ala Thr Val Ile Thr Met Asp Arg Lys Ala Ser
225                 230                235                 240

Lys Gln Gln Thr Asn Ile Asp Val Ile Tyr Glu Arg Val Arg Asp Asp
                245                250                255

Tyr Gln Leu His Trp Thr Ser Thr Asn Trp Lys Gly Thr Asn Thr Lys
                260                265                270

Asp Lys Trp Thr Asp Arg Ser Ser Glu Arg Tyr Lys Ile Asp Trp Glu
                275                280                285

Lys Glu Glu Met Thr Asn
                290

<210> SEQ ID NO 3
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Asp Ser Asp Ile Asn Ile Lys Thr Gly Thr Thr Asp Ile Gly
1               5                  10                 15

Ser Asn Thr Thr Val Lys Thr Gly Asp Leu Val Thr Tyr Asp Lys Glu
                20                 25                 30

Asn Gly Met His Lys Lys Val Phe Tyr Ser Phe Ile Asp Asp Lys Asn
                35                 40                 45

His Asn Lys Lys Leu Leu Val Ile Arg Thr Lys Gly Thr Ile Ala Gly
    50                  55                 60
```

```
Gln Tyr Arg Val Tyr Ser Glu Glu Gly Ala Asn Lys Ser Gly Leu Ala
 65                  70                  75                  80

Trp Pro Ser Ala Phe Lys Val Gln Leu Gln Leu Pro Asp Asn Glu Val
                 85                  90                  95

Ala Gln Ile Ser Asp Tyr Tyr Pro Arg Asn Ser Ile Asp Tyr Lys Ser
            100                 105                 110

Tyr Ser Ser Thr Leu Thr Tyr Gly Phe Asn Gly Asn Val Thr Gly Asp
        115                 120                 125

Asp Thr Gly Lys Ile Gly Gly Ile Ile Gly Ala Asn Val Ser Ile Gly
    130                 135                 140

His Ser Leu Ser Tyr Tyr Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn
    290

<210> SEQ ID NO 4
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cccccccccc cccccccccc cccccccccc cccccccccc cccccccccc cccccccccc      60
cccccccccc cccccccccc cccccccccc cccccccccc                            100

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                            100

<210> SEQ ID NO 6
<211> LENGTH: 100
<212> TYPE: DNA
```

-continued

```
<213> ORGANISM: Artificial Sequence
<220> FEATURE:
<223> OTHER INFORMATION: Description of Artificial Sequence: Synthetic
      polynucleotide

<400> SEQUENCE: 6
cccccccccc cccccccccc cccccccccc cccccccccc cccccccccc aaaaaaaaaa      60
aaaaaaaaaa aaaaaaaaaa aaaaaaaaaa aaaaaaaaaa                           100
```